(12) United States Patent
Mihara et al.

(10) Patent No.: US 8,980,937 B2
(45) Date of Patent: Mar. 17, 2015

(54) INSECTICIDAL ARYL PYRROLIDINES

(75) Inventors: Jun Mihara, Tochigi (JP); Tetsuya Murata, Tochigi (JP); Daiei Yamazaki, Tochigi (JP); Yasushi Yoneta, Saitama (JP); Katsuhiko Shibuya, Tochigi (JP); Eiichi Shimojo, Tochigi (JP); Ulrich Görgens, Ratingen (DE)

(73) Assignee: Bayer CropScience AG, Monheim (DE)

( * ) Notice: Subject to any disclaimer, the term of this patent is extended or adjusted under 35 U.S.C. 154(b) by 400 days.

(21) Appl. No.: 13/472,020

(22) Filed: May 15, 2012

(65) Prior Publication Data

US 2012/0232278 A1   Sep. 13, 2012

Related U.S. Application Data

(63) Continuation of application No. 12/597,015, filed as application No. PCT/EP2008/003105 on Apr. 14, 2008, now Pat. No. 8,188,122.

(30) Foreign Application Priority Data

Apr. 23, 2007   (JP) ................................ 2007-112855

(51) Int. Cl.
| | | |
|---|---|---|
| A01N 43/36 | (2006.01) | |
| A01N 43/40 | (2006.01) | |
| C07D 401/04 | (2006.01) | |
| C07D 207/04 | (2006.01) | |
| C07D 401/12 | (2006.01) | |
| C07D 401/14 | (2006.01) | |
| C07D 403/10 | (2006.01) | |
| C07D 207/06 | (2006.01) | |
| C07C 205/11 | (2006.01) | |

(52) U.S. Cl.
CPC .............. *C07C 205/11* (2013.01); *A01N 43/36* (2013.01); *A01N 43/40* (2013.01); *C07D 207/04* (2013.01); *C07D 207/06* (2013.01); *C07D 401/04* (2013.01); *C07D 401/12* (2013.01); *C07D 401/14* (2013.01); *C07D 403/10* (2013.01)
USPC ......... 514/429; 546/276.4; 548/577; 568/936

(58) Field of Classification Search
None
See application file for complete search history.

(56) References Cited

U.S. PATENT DOCUMENTS

| | | | |
|---|---|---|---|
| 3,931,162 | A | 1/1976 | Caldwell et al. |
| 5,171,355 | A | 12/1992 | Negele et al. |
| 7,915,282 | B2 | 3/2011 | Ruther et al. |
| 2002/0026052 | A1 | 2/2002 | Boschelli et al. |
| 2007/0043121 | A1 | 2/2007 | Brown et al. |
| 2007/0066617 | A1 | 3/2007 | Mita et al. |

FOREIGN PATENT DOCUMENTS

| | | |
|---|---|---|
| CA | 1339688 C | 2/1998 |
| EP | 1 731 512 A1 | 12/2006 |
| JP | 2008-110971 A | 5/2008 |
| WO | WO 98/06694 A1 | 2/1998 |
| WO | WO 03/067986 A1 | 8/2003 |
| WO | WO 2003/067986 A1 | 8/2003 |
| WO | WO 2005/085216 A1 | 9/2005 |
| WO | WO 2006/101828 A1 | 9/2006 |
| WO | WO 2008/128711 A1 | 10/2008 |

OTHER PUBLICATIONS

Bégué, J.-P., et al., "Enhancement of Alkene Reactivity by a Trifluoromethyl group: Synthesis of Pyrrolidines via 1,3-Dipolar Cycloaddition," *Tet. Letters* 34(20):3279-3282, Pergamon Press Ltd., England (1993).

Berger, D., et al., "Substituted 4-Anilino-7-phenyl-3-quinolinecarbonitriles as Src Kinase Inhibitors," *Bioorg. Med. Chem. Letters* 12:2989-2992, Elsevier Ltd, England (2002).

Camps, P., et al., "(R)- and (S)-3-Hydroxy-4,4-dimethyl-1-phenyl-2-pyrrolidinone as chiral auxiliaries in the enantioselective preparation of α-aryloxypropranoic herbicides α-chlorocarboxylic acids," *Tet. Assym.* 9(12):2065-2079, Elsevier Science Ltd., England (1998).

Cavalla, J.F., et al., "Analgetics Based on the Pyrrolidine Ring. III.," *J. Med. Chem.* 7:412-415, American Chemical Society, United States (1964).

Crane, L.J., et al., "Reactions of some *ortho* and *para* halogenated aromatic nitriles with ethylenediamine: selective synthesis of imidazolines," *Tetrahedron* 60:5325-5330, Elsevier Ltd., England (2004).

Hosomi, A., et al., "N-(Trimethylsilylmethyl)aminomethyl Ethers as Azomethine Ylide Synthons. A New and Convenient Access to Pyrrolidine Derivatives," *Chem. Letters* 13:1117-11120, The Chemical Society of Japan, Japan (1984).

Jiang, B. and Xu, Y., "Trifluoroisopropenylzinc Reagent as a Useful A-(Trifluoromethyl)ethenyl Carbanion Synthetic Equivalent. Preparation and Palladium-Catalyzed Coupling with Aryl Halides," *J. Org. Chem.* 56:7336-7340, American Chemical Society, United States (1991).

Lahm, G.P., et al., "Insecticidal anthranilic diamides: A new class of potent ryanodine receptor activators," *Bioorg. Med. Chem. Letters* 154898-4906, Elsevier Ltd, England (2005).

Lee, S.-W., et al., "Metabolic resistance mechanisms of the housefly (*Musca domestica*) resistant to pyraclofos," *Pest. Biochem. Physiol.* 85:76-83, Elsevier Inc., United States (2006).

(Continued)

*Primary Examiner* — Kortney L Klinkel
(74) *Attorney, Agent, or Firm* — Sterne, Kessler, Goldstein & Fox P.L.L.C.

(57) ABSTRACT

The present invention provides novel aryl pyrrolidines having an excellent insecticidal action as insecticides. Aryl pyrrolidines represented by the formula (I) and use thereof as insecticide.

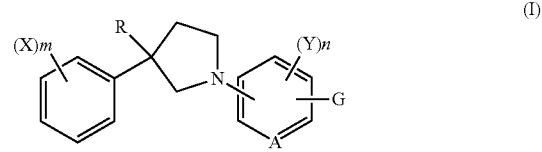

8 Claims, No Drawings

(56) References Cited

OTHER PUBLICATIONS

Mahalingam A.K., et al., "Convenient removal of *N-tert*-butyl from amides with scandium triflate," *Tet. Letters 47*:3051-3053, Elsevier Ltd, England (2006).

Nader, B. S., et al., "A Novel Fluoride Ion Mediated Olefination of Electron-Deficient Aryl Ketones by Alkanesulfonyl Halides," *J. Org. Chem. 59*:2898-2901, American Chemical Society, United States (1994).

Olofson, R.A. et al., "A New Reagent for the Selective, High-Yield N-Dealkylation of Tertiary Amines: Improved Synthesis of Naltrexone and Nalbuphine," *J. Org. Chem. 49*:2081-2082, American Chemical Society, United States (1984).

Otani, Y. et al., "An Evaluation of Amide Group Planarity in 7-Azabicyclo[2.2.1]heptane Amides. Low Amide Bond Rotation Barrier in Solution," *J. Am. Chem. Soc. 125*:15191-15199, American Chemical Society, United States (2003).

Ramana, D.V. and Viswanadham, S.K., "Unexpected Mass Spectral Skeletal Rearrangements in Aromatic Thioamides," *Organic Mass Spectroscopy 17*(9):409-415, Wiley-Heyden Ltd., England (1982).

Rui-Qi, P., et al., "A novel and convenient synthetic method for producing α-(trifluoromethyl)styrenes (3)," *J. Fluor. Chem. 95*:167-170, Elsevier Science S.A., Netherlands (1999).

Sayed Alam, M., et al., "Synthesis and Structure-Activity Relationships of 1-Phenyl-1*H*-1,2,3-tirazoles as Selective Insect GABA Receptor Antagonists," *J. Agric. Food Chem. 54*:1361-1372, American Chemical Society, United States (2006).

Sengupta, A., et al., "Ni(0)-Catalyzed Coupling of Aryl *O*-Carbamates and Aryl Triflates with Gringard Reagents. Directed Ortho Metalation Aligned Synthetic Methods for Polysubstituted Aromatics via a 1,2-Dipole Equivalent," *J. Org. Chem. 52*:4066-4068, American Chemical Society, United States (1992).

International Search Report with Written Opinion for International Applicant No. PCT/EP2008/003105, European Patent Office, Netherlands, mailed Aug. 12, 2008.

Unverified English language Translation of WIPO Patent Publication No. WO 03/067986 A1, published Aug. 21, 2003.

Amatore, M., et al., "Cobalt-Catalyzed Vinylation of Functionalized Aryl Halides with Vinyl Acetates," *Eur. J. Org. Chem. 6*:989-992, Wiley-VCH Verlag, Germany (2005).

Flynn, D.L., et al., "Chemical Library Purification Strategies Based on Principles of Complementary Molecular Reactivity and Molecular Recognition," *J. Am. Chem. Soc. 119*:4874-4881, American Chemical Society, United States (1997).

Jiang, B., and Xu, Y., "Trifluoroisopropenylzinc Reagent as a Useful α-(Trifluoromethyl)ethenyl carbanion Synthetic Equivalent. Preparation and Palladium-Catalyzed Coupling with Aryl Halides," *J. Org. Chem. 56*:7336-7340, American Chemical Society, United States (1991).

Katritzky, A.R., et al., "*N*-Acylbenzotriazoles: Neutral Acylating Reagents for the Preparation of Primary, Secondary, and Tertiary Amides," *J. Org. Chem. 65*:8210-8213, American Chemical Society, United States (2000).

Katritzky, A.R., et al., "Synthesis of 3,4-Dihydro-2*H*-1,3,5-thiadiazines," *J. Org. Chem. 67*:4960-4962, American Chemical Society (2002).

Katritzky, A.R., et al., "Efficient Microwave Access to Polysubstituted Amidines from Imidoylbenzotriazoles," *J.Org. Chem. 71*:3375-3380, American Chemical Society (2006).

Mori, T., and Ichikawa, J., "4-Difluoromethylated Quinoline Synthesis via Intramolecular $S_N 2'$ Reaction of α-Trifluoromethylstyrenes Bearing Imine Moieties," *Chemistry Letters 33*(9):1206-1207, Chemical Society of Japan, Japan (2004).

Nishide, K., et al., "A novel tandem [4$^+$+2] cycloaddition-elimination reaction of 4,4-dimethyl-2-styryl-1,3-oxathianes with olefins," *Tetrahedron Letters 41*:371-375, Elsevier Science Ltd., England (2000).

Pan, R-Q., et al., "A novel and convenient synthetic method for producing α-(trifluoromethyl)styrenes (3)," *Journal of Fluorine Chemistry 95*:167-170, Elsevier Science S.A., France (1999).

Snyder, J.K., and Stock, L.M., "Conformational Preferences in Alkylnitrosoureas," *J. Org. Chem. 45*:886-891, American Chemical Society, United States (1980).

Tiecco, M., et al., "Selective Mono-Arylation and -Alkylation of Bis(Alkylthio)Benzenes: The Importance of Steric Effects in the Nickel-Catalyzed Cross-Coupling of Aryl Alkyl Sulphides with Grignard Reagents," *Tetrahedron 39*(13):2289-2294, Pergamon Press Ltd., England (1983).

Tkachenko, S.E., et al., "Cyclization of N-Allylthiourea Derivatives by the Action of ∝-Chloronitrosoalkanes," *Chemistry of Heterocyclic Compounds 34*(3):347-350, Plenum Publishing, United States (1998).

Akira Hosomi et al., "N-(trimethylsilylmethyl)aminomethyl ethers as azomethine ylide synthons: a new and convenient access to pyrrolidine derivatives," *Chemistry Letters 7*:1117-1120 (1984), Chemical Society of Japan, Tokyo, Japan.

Bassam S. Nader et al., "A Novel Fluoride Ion Mediated Olefination of Electron-Deficient Aryl Ketones by Alkanesulfonyl Halides," *Journal of Organic Chemistry 59*(10):2898-2901(1994), American Chemical Society Washington, DC, USA.

Biao Jiang and Yuanyao Xu, Trifluoroisopropenylzinc reagent as a useful α-(tifluoromethyl(ethenyl carbanion synthetic equivalent. Preparation and palladium-catalyzed coupling with aryl halides, *Journal of Organic Chemistry 56*(26):7336-7340 (1991), American Chemical Society, Washington, DC, USA.

International Search Report for International Application No. PCT/EP2008/003105, European Patent Office, Netherlands, mailed on Aug. 12, 2008 (3 pages).

Jean-Pierre Bégué et al., "Enhancement of alkene reactivity by a trifluoromethyl group: Synthesis of pyrrolidines via 1,3-dipolar cycloaddition," *Tetrahedron Letters 34*(20):3279-3282 (1993), Elsevier, Oxford, UK.

Pelayo Camps et al., "(R)-and (S)-3-Hydroxy-4,4-dimethyl-1-phenyl-2-pyrrolidinone as chiral auxiliaries in the enantioselective preparation of α-aryloxypropanoic acid herbicides and α-chlorocarboxylic acids," *Tetrahedron: Asymmetry 9*(12):2065-2079 (1998), Elsevier Science, Oxford, UK.

R. A. Olofson, "A New Reagent for the Selective, High-Yield N-Dealkylation of Tertiary Amines: Improved Syntheses of Naltrexone and Nalbuphine," *Journal of Organic Chemistry 49*(11):2081-2082 (1984), American Chemical Society, Washington, DC, USA.

Rui-qi Pan et al., "A novel and convenient synthetic method for producing α-(tri-fluoromethyl)styrenes (3)," *Journal of Fluorine Chemistry 95*:167-170 (1999), Elsevier Sequoia, Lausanne, Switzerland.

(Uncertified) English language translation of International Application No. WO 2006/101828 A1 (167 pages).

Esp@cenet Database, English language abstract for JP-2008-110971-A (listed on accompanying PTO/SB/08A as document FP6).

INSECTICIDAL ARYL PYRROLIDINES

This application is a continuation of application Ser. No. 12/597,015, filed Oct. 22, 2009, currently pending, which is a National Phase Entry of International Application No. PCT/EP2008/003105, filed Apr. 14, 2008, which claims the benefit of Japanese Patent Application No. 2007-112855, filed Apr. 23, 2007.

The present invention relates to novel aryl pyrrolidines and the use thereof as insecticides.

WO2005/085216 describes that isoxazoline substituted benzamide compounds are useful as pest control agents.

The inventors were dedicated to studying to develop novel compounds exhibiting higher effects and a broad spectrum against animal pests, such as insects and acari. As a result, the inventors found novel aryl pyrrolidines showing an excellent, i.e. high activity, having a broad spectrum and are harmless to beneficial insects, such as bees, as well as effective against insect pests. Particularly to such insects which are resistant to insecticides, such as organophosphorus or carbamate agents.

The compounds according to the invention are represented by formula (I)

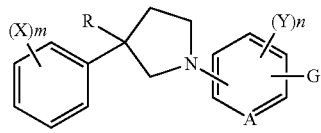

wherein
X which may be same or different, represents halogen, haloalkyl, nitro, alkyl, alkoxy, cyano, haloalkoxy, alkylthio, alkylsulfinyl, alkylsulfonyl, haloalkylthio, haloalkylsulfinyl, haloalkylsulfonyl, hydroxyl, mercapto, amino, alkylcarbonylamino, haloalkylcarbonylamino, benzoylamino, alkoxy-carbonylamino, haloalkoxycarbonylamino, alkylsulfonylamino or haloalkylsulfonylamino;
Y which may be same or different, represents halogen, haloalkyl, nitro, alkyl, alkoxy, cyano, haloalkoxy, alkylthio, alkylsulfinyl, alkylsulfonyl, haloalkylthio, haloalkylsulfinyl, haloalkylsulfonyl, hydroxyl, mercapto, amino, alkylcarbonylamino, haloalkylcarbonylamino, benzoylamino, alkoxy-carbonylamino, haloalkoxycarbonylamino, alkylsulfonylamino or haloalkylsulfonylamino;
R represents alkyl or haloalkyl;
m represents 0, 1, 2, 3, 4 or 5;
n represents 1, 2, 3 or 4;
G is selected from the group consisting of

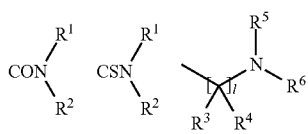

wherein
$R^1$ and $R^2$ each independently represents hydrogen; optionally substituted alkyl, alkenyl, alkynyl, cycloalkyl or alkylsulfonyl; haloalkylsulfonyl or $CH_2$—$R^7$; or when taken together represent $C_{2-4}$ alkylene;
$R^3$ and $R^4$ each independently represents hydrogen; cyano; optionally substituted alkyl, alkenyl, alkynyl, cycloalkyl; or when taken together represent $C_{2-6}$ alkylene;
l represents 1, 2 or 3;
$R^5$ represents hydrogen; alkyl; optionally substituted cycloalkyl; haloalkyl; cyano; alkenyl; alkynyl; alkylcarbonyl or $CH_2$—$R^7$;
$R^6$ represents formyl, cyano, alkylcarbonyl, alkylthiocarbonyl, haloalkylcarbonyl, haloalkylthiocarbonyl, alkylaminocarbonyl, alkylaminothiocarbonyl, dialkylaminocarbonyl, dialkylaminothiocarbonyl, alkoxyaminocarbonyl, alkoxyaminothiocarbonyl, alkoxycarbonyl, alkoxythiocarbonyl, thioalkoxycarbonyl, thioalkoxythiocarbonyl, CO—$R^7$, CS—$R^7$, alkylsulfonyl or haloalkylsulfonyl; or alternatively
$R^5$ and $R^6$ when taken together with the nitrogen to which they are attached to form a 3-6 membered ring which contains at least one N atom and, optionally at least another heteroatom selected from S and O, wherein the ring is optionally substituted with keto or thioketo;
or the group consisting of the heterocycles G1 to G9:

G1

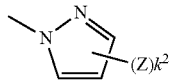
G2

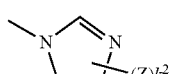
G3

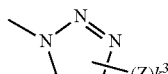
G4

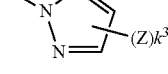
G5

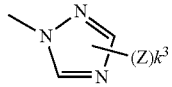
G6

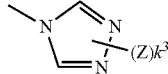
G7

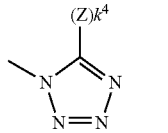
G8

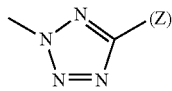
G9

Z which may be same or different, represents halogen, haloalkyl, nitro, alkyl, alkoxy, cyano, haloalkoxy, alkylsulfonyl, haloalkylsulfonyl, hydroxyl or mercapto;
$k^1$ represents 0, 1, 2, 3 or 4;
$k^2$ represents 0, 1, 2 or 3;
$k^2$ represents 0, 1 or 2;
$k^4$ represents 0 or 1;
$R^7$ represents phenyl or heterocyclic ring, which are optionally substituted with at least one substituent selected from halogen and $C_{1-6}$ alkyl; and
A represents C or N.

Among the compounds of formula (I) of the invention, preferred compounds are compounds of formula (Ia)

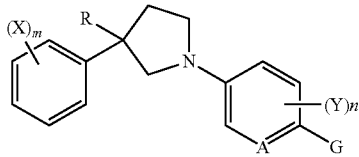

wherein X, Y, R, A, G, Y, n and m are as defined above.

Among the compounds of the formula (I) or formula (Ia) of the invention, further preferred compounds are those wherein X which may be same or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, hydroxyl, mercapto, amino, $C_{1-6}$ alkylcarbonylamino, $C_{1-6}$ haloalkylcarbonylamino, benzoylamino, $C_{1-6}$ alkoxy-carbonylamino, $C_{1-6}$ haloalkoxy-carbonylamino, $C_{1-6}$ alkylsulfonylamino or $C_{1-6}$ haloalkylsulfonylamino;

Y which may be same or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, hydroxyl, mercapto, amino, $C_{1-6}$ alkylcarbonylamino, $C_{1-6}$ haloalkylcarbonylamino, benzoylamino, $C_{1-6}$ alkoxy-carbonylamino, $C_{1-6}$ haloalkoxy-carbonylamino, $C_{1-6}$ alkylsulfonylamino or $C_{1-6}$ haloalkylsulfonylamino;

R represents $C_{1-6}$ alkyl or $C_{1-6}$ haloalkyl;

m represents 0, 1, 2, 3, 4 or 5;

n represents 0, 1, 2, or 4;

G is selected from the group consisting of

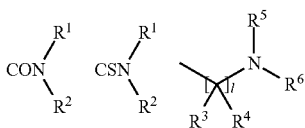

or group consisting of the G1 to G9:

 G1

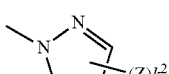 G2

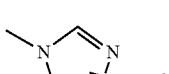 G3

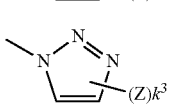 G4

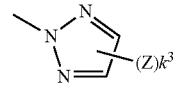 G5

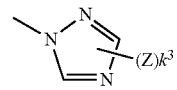 G6

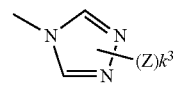 G7

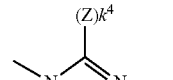 G8

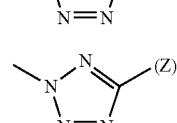 G9 wherein $R^1$ and $R^2$ each independently represents hydrogen; optionally substituted $C_{1-6}$ alkyl, $C_{2-6}$ alkenyl, $C_{2-6}$ alkynyl, $C_{3-7}$ cycloalkyl; $C_{1-6}$ alkylsulfonyl, $C_{1-6}$ haloalkylsulfonyl or $CH_2$—$R^7$; or when taken together represent $C_{2-6}$ alkylene;

$R^3$ and $R^4$ each independently represents hydrogen, cyano; optionally substituted $C_{1-6}$ alkyl, $C_{2-6}$ alkenyl, $C_{2-6}$ alkynyl, $C_{3-7}$ cycloalkyl; or $C_{1-6}$ alkoxycarbonyl; or when taken together represent $C_{2-6}$ alkylene;

l represents 1 or 2 or 3;

$R^5$ represents hydrogen; $C_{1-6}$ alkyl; optionally substituted $C_{3-7}$ cycloalkyl; $C_{1-6}$ haloalkyl; cyano; $C_{2-6}$ alkenyl; $C_{2-6}$ alkynyl; $C_{1-6}$ alkylcarbonyl; or $CH_2$—$R^7$;

$R^6$ represents formyl, cyano, $C_{1-6}$ alkylcarbonyl, $C_{1-6}$ alkylthiocarbonyl, $C_{1-6}$ haloalkylcarbonyl, $C_{1-6}$ haloalkylthiocarbonyl, $C_{1-6}$ alkylaminocarbonyl, $C_{1-6}$ alkylaminothiocarbonyl, dialkylamino-carbonyl having from 2 to 8 carbonatoms, dialkylaminothiocarbonyl having from 2 to 8 carbon atoms, $C_{1-6}$ alkoxyaminocarbonyl, $C_{1-6}$ alkoxyaminothiocarbonyl, $C_{1-6}$ alkoxycarbonyl, $C_{1-6}$ alkoxythiocarbonyl, $C_{1-6}$ thioalkoxycarbonyl, $C_{1-6}$ thioalkoxythiocarbonyl, CO—$R^7$, CS—$R^7$, $C_{1-6}$ alkylsulfonyl or $C_{1-6}$ haloalkylsulfonyl; or $R^5$ and $R^6$ when taken together with the nitrogen to which they are attached to form a 3-6 membered ring which contains at least one N atom and, optionally at least another heteroatom selected from S and O, wherein the ring is optionally substituted with keto or thioketo;

Z which may be same or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylsulfonyl, $C_{1-6}$ haloalkylsulfonyl, hydroxyl or mercapto;

$k^1$ represents 0, 1, 2, 3 or 4;

$k^2$ represents 0, 1, 2 or 3;

$k^3$ represents 0 or 1;

$k^4$ represents 0 or 1;

$R^7$ represents phenyl or a heterocyclic ring, which are optionally substituted with at least one substituent selected from fluorine, chlorine, bromine, iodine and $C_{1-6}$ alkyl; and A represents C or N.

Further preferred compounds of the formula (I) or formula (Ia) of the invention are such compounds wherein X which may be same or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, hydroxyl, mercapto, amino, $C_{1-6}$ alkylcarbonylamino, $C_{1-6}$ haloalkylcarbonylamino, benzoylamino, $C_{1-6}$ alkoxy-carbonylamino, $C_{1-6}$ haloalkoxy-carbonylamino, $C_{1-6}$ alkylsulfonylamino or $C_{1-6}$ haloalkylsulfonylamino;

Y which may be same or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, hydroxyl, mercapto, amino, $C_{1-6}$ alkylcarbonylamino, $C_{1-6}$ haloalkylcarbonylamino, benzoylamino, $C_{1-6}$ alkoxycarbonylamino, $C_{1-6}$ haloalkoxy-carbonylamino, $C_{1-6}$ alkylsulfonylamino or $C_{1-6}$ haloalkylsulfonylamino;

R represents $C_{1-6}$ alkyl or $C_{1-6}$ haloalkyl;

m represents 0, 1, 2 or 3;

n represents 0, 1, 2 or 3;

G is selected from the group consisting of

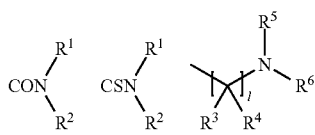

or the group consisting of the heterocycles G1 to G9:

 G1

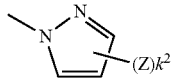 G2

 G3

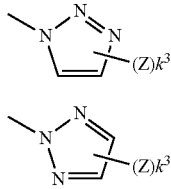 G4

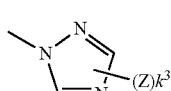 G5

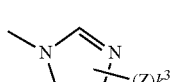 G6

G7

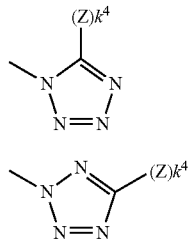 G8

G9

$R^1$ and $R^2$ each independently represents hydrogen, $C_{1-6}$ alkyl which may be substituted, $C_{2-6}$ alkenyl which may be substituted, $C_{2-6}$ alkynyl which may be substituted, $C_{3-7}$ cycloalkyl which may be substituted, $C_{1-6}$ alkylsulfonyl, $C_{1-6}$ haloalkylsulfonyl or $CH_2$—$R^7$; or when taken together represent $C_{3-5}$ alkylene;

$R^3$ and $R^4$ each independently represents hydrogen, cyano, $C_{1-6}$ alkyl which may be substituted, $C_{2-6}$ alkenyl which may be substituted, $C_{2-6}$ alkynyl which may be substituted, $C_{3-7}$ cycloalkyl which may be substituted or $C_{1-6}$ alkoxycarbonyl; or when taken together represent $C_{3-5}$ alkylene;

l represents 1 or 2;

$R^5$ represents hydrogen, $C_{1-6}$ alkyl, $C_{3-7}$ cycloalkyl which may be substituted, $C_{1-6}$ haloalkyl, cyano, $C_{2-6}$ alkenyl, $C_{2-6}$ alkynyl, $C_{1-6}$ alkyl-carbonyl or $CH_2$—$R^7$;

$R^6$ represents formyl, cyano, $C_{1-6}$ alkyl-carbonyl, $C_{1-6}$ alkylthio-carbonyl, $C_{1-6}$ haloalkylcarbonyl, $C_{1-6}$ haloalkylthio-carbonyl, $C_{1-4}$ alkylamino-carbonyl, $C_{1-4}$ alkylaminothio-carbonyl, dialkylamino-carbonyl having from 2 to 8 carbonatoms, dialkylaminothio-carbonyl having from 2 to 8 carbon atoms, $C_{1-6}$ alkoxyamino-carbonyl, $C_{1-6}$ alkoxyaminothio-carbonyl, $C_{1-6}$ alkoxy-carbonyl, $C_{1-6}$ alkoxythio-carbonyl, $C_{1-6}$ thioalkoxy-carbonyl, $C_{1-6}$ thioalkoxythio-carbonyl, CS—$R^7$, $C_{1-6}$ alkylsulfonyl or $C_{1-6}$ haloalkylsulfonyl; or alternatively $R^5$ and $R^6$ when taken together with the nitrogen to which they are attached to form a 3-6 membered ring which contains at least one N atom and, optionally at least another heteroatom selected from S and O, wherein the ring is optionally substituted with keto or thioketo;

Z which may be same or different, represents halogen, $C_{1-6}$ haloalkyl, nitro, $C_{1-6}$ alkyl, $C_{1-6}$ alkoxy, cyano, $C_{1-6}$ haloalkoxy, $C_{1-6}$ alkylsulfonyl, $C_{1-6}$ haloalkylsulfonyl, hydroxyl or mercapto;

$k^1$ represents 0, 1, 2 or 3;

$k^2$ represents 0, 1 or 2;

$k^3$ represents 0 or 1;

$k^4$ epresents 0 or 1;

$R^7$ represents phenyl or a heterocyclic ring, which are optionally substituted with at least one substituent selected from fluorine, chlorine, bromine, and $C_{1-6}$ alkyl; and A represents C or N.

Among those compounds of the formula (I) or formula (Ia), particularly preferable are compounds wherein X which may be same or different, represents halogen, $C_{1-4}$ haloalkyl, nitro, $C_{1-4}$ alkyl, $C_{1-4}$ alkoxy, cyano, $C_{1-4}$ haloalkoxy, $C_{1-4}$ alkylthio, $C_{1-4}$ alkylsulfinyl, $C_{1-4}$ alkylsulfonyl, $C_{1-4}$ haloalkylthio, $C_{1-4}$ haloalkylsulfinyl, $C_{1-4}$ haloalkylsulfonyl, hydroxyl, mercapto, amino, $C_{1-4}$ alkylcarbonylamino, $C_{1-4}$ haloalkylcarbonylamino, benzoylamino, $C_{1-4}$ alkoxycarbonylamino, $C_{1-4}$ haloalkoxy-carbonylamino, $C_{1-4}$ alkylsulfonylamino or $C_{1-4}$ haloalkylsulfonylamino;

Y which may be same or different, represents halogen, $C_{1-4}$ haloalkyl, nitro, $C_{1-4}$ alkyl, $C_{1-4}$ alkoxy, cyano, $C_{1-4}$ haloalkoxy, $C_{1-4}$ alkylthio, $C_{1-4}$ alkylsulfinyl, $C_{1-4}$ alkylsulfonyl, $C_{1-4}$ haloalkylthio, $C_{1-4}$ haloalkylsulfinyl, $C_{1-4}$ haloalkylsulfonyl, hydroxyl, mercapto, amino, $C_{1-4}$ alkyl-carbonylamino, $C_{1-4}$ haloalkylcarbonylamino, benzoylamino, $C_{1-4}$ alkoxy-carbonylamino, $C_{1-4}$ haloalkoxy-carbonylamino, $C_{1-4}$ alkylsulfonylamino or $C_{1-4}$ haloalkylsulfonylamino;

R represents $C_{1-4}$ alkyl or $C_{1-4}$ haloalkyl;

m represents 0, 1, 2 or 3;

n represents 0, 1, 2 or 3;

G is selected from the group consisting of

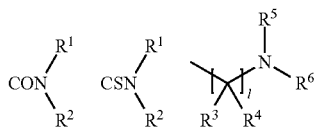

or the group consisting of the heterocycles G1 to G9:

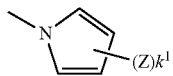 G1

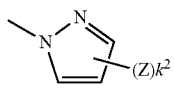 G2

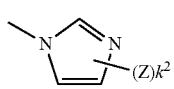 G3

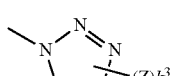 G4

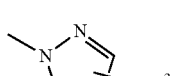 G5

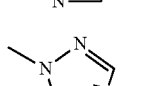 G6

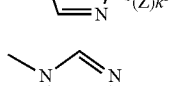 G7

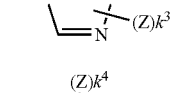 G8

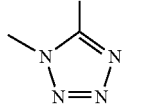 G9

$R^1$ and $R^2$ each independently represents hydrogen, $C_{1-4}$ alkyl which may be substituted, $C_{2-4}$ alkenyl which may be substituted, $C_{2-4}$ alkynyl which may be substituted, $C_{3-6}$ cycloalkyl which may be substituted, $C_{1-4}$ alkylsulfonyl, $C_{1-4}$ haloalkylsulfonyl or $CH_2R^7$; or when taken together represent $C_{3-5}$ alkylene;

$R^3$ and $R^4$ each independently represents hydrogen, cyano, $C_{1-4}$ alkyl which may be substituted, $C_{2-4}$ alkenyl which may be substituted, $C_{2-4}$ alkynyl which may be substituted, $C_{3-6}$ cycloalkyl which may be substituted or $C_{1-4}$ alkoxycarbonyl; or when taken together represent $C_{3-5}$ alkylene;

l represents 1 or 2;

$R^5$ represents hydrogen, $C_{1-4}$ alkyl, $C_{3-6}$ cycloalkyl which may be substituted, $C_{1-4}$ haloalkyl, cyano, $C_{2-4}$ alkenyl, $C_{2-4}$ alkynyl, $C_{1-4}$ alkyl-carbonyl or $CH_2$—$R^7$;

$R^6$ represents formyl, cyano, $C_{1-4}$ alkyl-carbonyl, $C_{1-4}$ alkylthio-carbonyl, $C_{1-4}$ haloalkylcarbonyl, $C_{1-4}$ haloalkylthio-carbonyl, $C_{1-4}$ alkylamino-carbonyl, $C_{1-4}$ alkylaminothio-carbonyl, dialkylamino-carbonyl having from 2 to 8 carbonatoms, dialkylaminothio-carbonyl having from 2 to 8 carbon atoms, $C_{1-4}$ alkoxyamino-carbonyl, $C_{1-4}$ alkoxyaminothio-carbonyl, $C_{1-4}$ alkoxy-carbonyl, $C_{1-4}$ alkoxythio-carbonyl, $C_{1-4}$ thioalkoxy-carbonyl, $C_{1-4}$ thioalkoxythio-carbonyl, CO—$R^7$, CS—$R^7$, $C_{1-4}$ alkylsulfonyl or $C_{1-4}$ haloalkylsulfonyl; or alternatively $R^5$ and $R^6$ when taken together with the nitrogen to which they are attached to form a 3-6 membered ring which contains at least one N atom and, optionally at least another heteroatom selected from S and O, wherein the ring is optionally substituted with keto or thioketo;

Z which may be same or different, represents halogen, $C_{1-4}$ haloalkyl, nitro, $C_{1-4}$ alkyl, $C_{1-4}$ alkoxy, cyano, $C_{1-4}$ haloalkoxy, $C_{1-4}$ alkylsulfonyl, $C_{1-4}$ haloalkylsulfonyl, hydroxyl or mercapto;

$k^1$ represents 0, 1, 2 or 3;

$k^2$ represents 0, 1 or 2;

$k^3$ represents 0 or 1;

$k^4$ represents 0 or 1;

$R^7$ represents phenyl or a heterocyclic ring, which are optionally substituted with at least one substituent selected from fluorine, chlorine, bromine, and $C_{1-4}$ alkyl; and In an embodiment of the invention the compounds of the formula (I) or formula (Ia) are compounds wherein X which may be same or different, represents chlorine, fluorine, bromine, trifluormethyl, difluormethyl, fluormethyl, nitro, methyl, ethyl, propyl, i-propyl, butyl, t-butyl, 2-methyl-propyl, methoxy, ethoxy, propoxy, i-propoxy, n-butoxy, t-butoxy, 2-methyl-propoxy, cyano, trifluormethoxy, difluormethyoxy, fluormethyoxy, thiomethyl, thioethyl, thiopropyl, thio-i-propyl, thiobutyl, thio-t-butyl, 2-methyl-thiopropyl, methylsulfinyl, ethylsulfinyl, propylsulfinyl, i-propylsulfinyl, butylsulfinyl, t-butylsulfinyl, 2-methyl-propylsulfinyl, methylsulfonyl, ethylsulfonyl, propylsulfonyl, i-propylsulfonyl, butylsulfonyl, t-butylsufonyl, 2-methyl-propylsulfonyl, trifluormethylthio, trifluormethylsulfinyl, trifluormethylsulfonyl, hydroxyl, mercapto, amino, methylcarbonylamino, ethylcarbonylamino, propylcarbonylamino, i-propylcarbonylamino, butylcarbonylamino, t-butylcarbonylamino, 2-methyl-propylcarbonylamino, benzoylamino, methoxy-carbonylamino, ethoxy-carbonylamino, propoxy-carbonylamino, i-propoxy-carbonylamino, butyoxy-carbonylamino, t-butyloxy-carbonylamino, 2-methyl-propoxy-carbonylamino, trifluormethoxycarbonylamino, $C_{1-4}$ alkylsulfonylamino or $C_{1-4}$ haloalkylsulfonylamino;

Y which may be same or different, represents chlorine, fluorine, bromine, iodine, trifluormethyl, difluormethyl, fluormethyl, nitro, methyl, ethyl, propyl, i-propyl, butyl, t-butyl, 2-methyl-propyl, methoxy, ethoxy, propoxy, i-propoxy, n-butoxy, t-butoxy, 2-methyl-propoxy, cyano, trifluormethoxy, difluormethyoxy, fluormethyoxy, thiomethyl, thioethyl, thiopropyl, thio-i-propyl, thiobutyl, thio-t-butyl, 2-methyl-thiopropyl, methylsulfinyl, ethylsulfinyl, propylsulfinyl, i-propylsulfinyl, butylsulfinyl, t-butylsulfinyl, 2-methyl-propylsulfinyl, methylsulfonyl, ethylsulfonyl, propylsulfonyl, i-propylsulfonyl, butylsulfonyl, t-butylsulfonyl, 2-methyl-propylsulfonyl, trifluormethylthio, trifluormethylsulfinyl, trifluormethylsulfonyl, hydroxyl, mercapto, amino, trifluormethylcarbonylamino, methylcarbonylamino, ethylcarbonylamino, propylcarbonylamino, i-propylcarbonylamino, butylcarbonylamino, t-butylcarbonylamino, 2-methyl-propylcarbonylamino, 2,2,2-trichlorethylcarbonyl amino, benzoylamino, methoxy-carbonylamino, ethoxy-carbonylamino, propoxy-carbonylamino, i-propoxy-carbonylamino, butyloxy-carbonylamino, t-butyloxy-carbonylamino, 2-methyl-propoxy-carbonylamino, trifluormethoxycarbonylamino, $C_{1-4}$ alkylsulfonylamino or $C_{1-4}$ haloalkylsulfonylamino;

R represents methyl, ethyl, propyl, i-propyl, butyl, t-butyl, 2-methyl-propyl or trifluormethyl, difluormethyl, fluormethyl;

m represents 0, 1, 2 or 3;

n represents 0, 1, 2 or 3;

G represents:

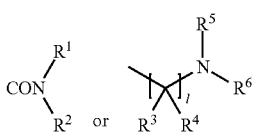

or alternatively represents the following heterocycles of G1-G9:

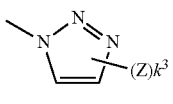 G4

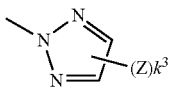 G5

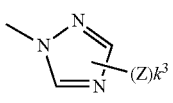 G6

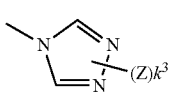 G7

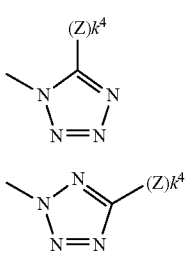 G8

G9

$R^1$ and $R^3$ each independently represents hydrogen, $C_{1-4}$ alkyl which may be substituted, $C_{2-4}$ alkenyl which may be substituted, $C_{2-4}$ alkynyl which may be substituted, $C_{3-6}$ cycloalkyl which may be substituted, $C_{1-4}$ alkylsulfonyl, $C_{1-4}$ haloalkylsulfonyl or $CH_2$—$R^7$; or when taken together represent $C_{3-5}$ alkylene;

$R^3$ and $R^4$ each independently represents hydrogen, cyano, $C_{1-4}$ alkyl which may be substituted, $C_{2-4}$ alkenyl which may be substituted, $C_{2-4}$ alkynyl which may be substituted, $C_{3-6}$ cycloalkyl which may be substituted or $C_{1-4}$ alkoxy-carbonyl; or when taken together represent $C_{3-5}$ alkylene;

l represents 1 or 2;

$R^5$ represents hydrogen, $C_{1-4}$ alkyl, $C_{3-6}$ cycloalkyl which may be substituted, $C_{1-4}$ haloalkyl, cyano, $C_{2-4}$ alkenyl, $C_{2-4}$ alkynyl, $C_{1-4}$ alkyl-carbonyl or $CH_2$—$R^7$;

$R^6$ represents formyl, cyano, $C_{1-4}$ alkyl-carbonyl, $C_{1-4}$ alkylthio-carbonyl, $C_{1-4}$ haloalkyl-carbonyl, $C_{1-4}$ haloalkylthio-carbonyl, alkylamino-carbonyl, alkylaminothio-carbonyl, dialkylamino-carbonyl having from 2 to 6 carbon atoms, dialkylaminothio-carbonyl having from 2 to 6 carbon atoms, $C_{1-4}$ alkoxyamino-carbonyl, $C_{1-4}$ alkoxyaminothio-carbonyl, $C_{1-4}$ alkoxy-carbonyl, alkoxythio-carbonyl, thioalkoxy-carbonyl, $C_{1-4}$ thioalkoxythio-carbonyl, CO—$R^7$, CS—$R^7$, $C_{1-4}$ alkylsulfonyl or $C_{1-4}$ haloalkylsulfonyl; or alternatively Z which may be same or different, represents chlorine, bromine or iodine, trifluormethyl, nitro, methyl, ethyl, propyl, i-propyl, butyl, t-butyl, 2-methyl-propyl, cyano;

$k^3$ represents 0 or 1;

$k^4$ represents 0 or 1;

$R^7$ represents phenyl which may be substituted or a heterocyclic ring selected from the group consisting of pyridyl, pyrolidinyl, imidazolyl, triazolyl, oxadiazolyl, tetrazolyl, pyrimidinyl, and triazinyl which may be substituted, wherein the substituent is at least one selected from chlorine, bromine, iodine and methyl, ethyl, i-propyl, n-propyl, 2-methyl propyl, n-butyl and t-butyl; and A represents C.

The compounds of the formula (I) or formula (Ia) of the present invention have asymmetric carbons, and thus encompass optical isomers.

As used herein, "alkyl" refers to linear or branched $C_{1-12}$ alkyl such as methyl, ethyl, n- or iso-propyl, n-, iso-, sec-, or tert-butyl, n-pentyl, n-hexyl, n-heptyl, n-octyl, n-nonyl, n-decyl, n-undecyl, n-dodecyl and the like, preferably refers to $C_{1-6}$ alkyl.

As used herein, "haloalkyl" refers to alkyl groups having 1 to 12 carbonatoms, preferably 1 to 6 or 1 to 4 carbon atoms in which at least on hydrogen atom is exchanged by a halogen. Suitable haloalkyls are for example CH2F, CHF2, CF3, CF2Cl, CFCl2, CF2Br, CF2CF3, CFHCF3, CH2CF3, CFClCF3, CCl2CF3, CF2CH3, CF2CH2F, CF2CHF2, CF2CF2Cl, CF2CF2Br, CFHCH3, CFHCH2F, CFHCHF2, CHFCF3, CHFCF2Cl, CHFCF2Br, CH2CF3, CFClCF3, CCl2CF3, CF2CF2CF3, CH2CF2CF3, CF2CH2CF3, CF2CF2CH3, CHFCF2CF3, CF2CHFCF3, CF2CF2CHF2, CF2CF2CH2F, CF2CF2CF2Cl, CF2CF2CF2Br. The haloalkyl moiety can be substituted by at least one suitable substituent.

As used herein, "alkoxy" refers to alkoxy groups having 1 to 12 carbonatoms, preferably 1 to 6 or 1 to 4 carbon atoms. Suitable alkoxy groups are for example methoxy, ethoxy, n-propoxy, i-propoxy, n-, iso-, sec-oder tert-butoxy, pentyloxy, oder hexyloxy. The alkoxy moiety can be substituted by at least one suitable substituent.

Each alkyl moiety in each group having alkyl as a part of its configuration may additionally be illustrated by those same as described for "alkyl" above.

"Acylamino" represents, for example, alkylcarbonylamino, cyclopropylcarbonylamino and benzoylamino, wherein alkyl moiety may be illustrated by those same as described for "alkyl" above.

"Halogen" and each halogen moiety in each group substituted with halogen refer to fluorine, chlorine, bromine and iodine, preferably refer to fluorine, chlorine or bromine.

"Cycloalkyl" refers to $C_{3-8}$ cycloalkyl such as cyclopropyl, cyclobutyl, cyclopentyl, cyclohexyl, cycloheptyl, cyclooctyl, preferably refers to $C_{3-7}$ cycloalkyl.

"Alkenyl" refers to $C_{2-5}$ alkenyl such as vinyl, allyl, 1-propenyl, 1-(or 2- or 3-)butenyl, 1-pentenyl, preferably refers to $C_{2-4}$ alkenyl.

"Alkynyl" refers to $C_{2-5}$ alkynyl such as ethynyl, propargyl, 1-propynyl, butane-3-ynyl, pentane-4-ynyl and the like, preferably refers to $C_{2-4}$ alkynyl.

A "heterocyclic group" refers to a 5 or 6-membered heterocyclic group containing at least one hetero atom selected from N, O or S, wherein said ring also refers to a condensed heterocyclic group which may be benzo-condensed.

Heterocyclic groups are for example furyl, thienyl, pyrrolyl, isoxazolyl, pyrazolyl, oxazolyl, oxathiazolyl, imidazolyl, triazolyl, oxadiazolyl, thiadiazolyl, tetrazolyl, pyridyl, pyrolidinyl, pyrimidinyl, pyridazinyl, pyrazinyl, triazinyl, indolyl, benzoxazolyl, quinolyl and the like.

The compounds of the formula (I) or formula (Ia) of the invention may be obtained, for example, by the preparation methods (a) to (j) described below.

Preparation method (a) comprises reacting a compound of formula (II)

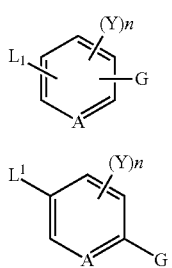

(II)

wherein X, R and m have the same meanings as defined herein, with a compound of formula (III) or formula (III-a)

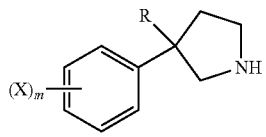

(III)

(III-a)

wherein
Y, A, G and n have the same meanings as defined herein,
$L^1$ represents halogen or a $C_1$-$C_4$ haloalkylsulfonyloxy group.

In an embodiment of the preparation method (a), the compounds of formula (II) and formula (III) or formula (III-a) are reacted in the presence of a base or in the presence of at least one metallic catalyst.

Preparation methods (b) and (c) for the preparation of compounds according to formula (I) or formula (Ia), wherein G stands for a group —$CONR^1R^2$:

Method (b) comprises reacting a compound represented by the formula (IV) or formula (IV-a)

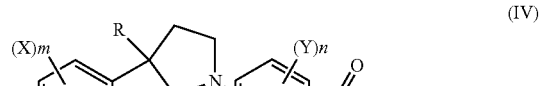

(IV)

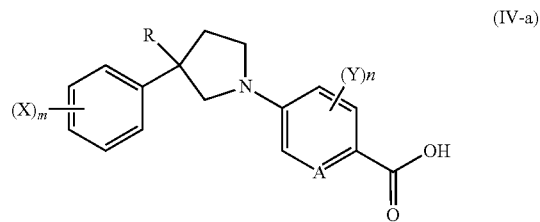

(IV-a)

wherein X, Y, R, A, m and n have the same meanings as defined herein, or
a compound represented by the formula (V) or formula (V-a)

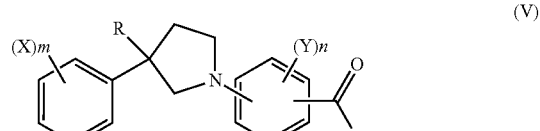

(V)

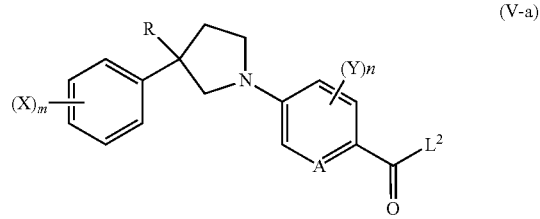

(V-a)

wherein X, Y, R, A, m and n have the same meanings as defined herein and $L^2$ represents chlorine, bromine, $C_{1-4}$ alkylcarbonyloxy, $C_{1-4}$ alkoxycarbonyloxy or azolyl,
with a compound represented by the formula (VI):

(VI)

wherein $R^1$ and $R^2$ have the same meanings as defined herein, using a condensation agents, if desired, in the presence of base.

Method (c) comprises reacting a compound represented by the formula (Ib) or formula (Ie):

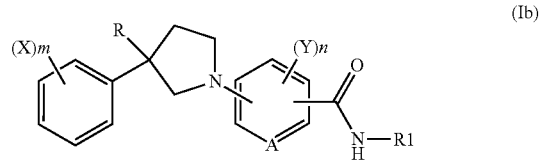

(Ib)

(Ie)

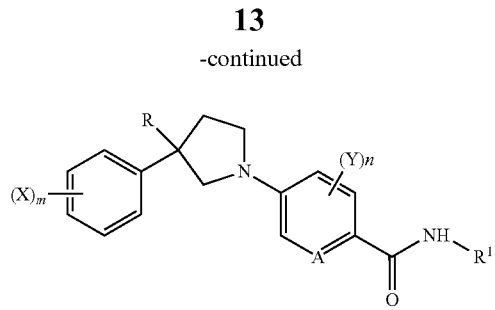

wherein X, Y, R, R¹, A, m and n have the same meanings as defined herein,
with a compound represented by the formula:
R²-L³ (VII), wherein R² has the same meaning as defined herein and L³ represents chlorine, bromine, iodine, $C_{1-4}$ alkylsulfonyloxy, $C_{1-4}$ haloalkylsulfonyloxy, arylsulfonyloxy or azolyl, if desired, in the presence of base.

Preparation method (d) for the preparation of compounds according to formula (I) or formula (Ia), wherein G stands for a group —CSNR¹R²:

Method (d) comprises reacting a compound represented by the formula (If) or formula (Id):

(If)

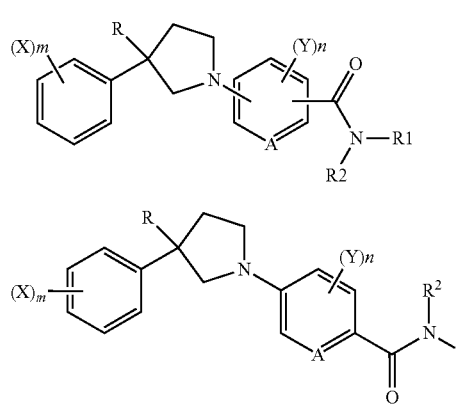

(Id)

wherein X, Y, R, R¹, R², A, m and n have the same meanings as defined herein, with sulfating agents.

Preparation methods (e), (f) and (g) for the preparation of compounds according to formula (I) or formula (Ia), wherein G stands for

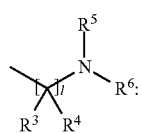

Method (e) comprises reacting a compound represented by the formula (VIII) or formula (VIII-b):

(VIII)

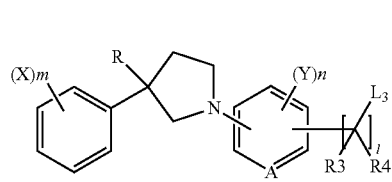

(VIII-b)

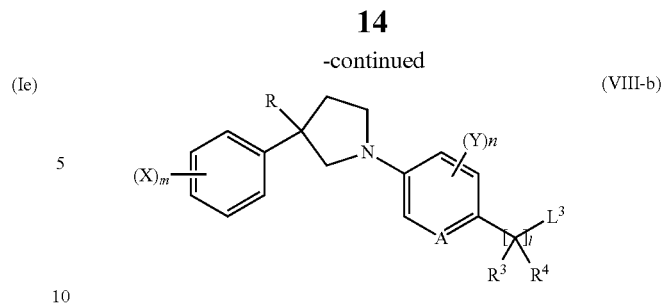

wherein X, Y, R, R³, R⁴, A, l, m, n and L³ have the same meanings as defined herein, with a compound represented by the formula (IX):

(IX)

wherein R⁵ and R⁶ have the same meanings as defined herein, if desired, in the presence of base.

Method (f) comprises reacting a compound represented by the formula (X) or formula (X-a):

(X)

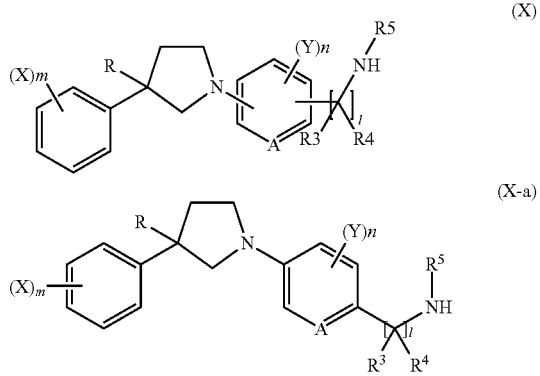

(X-a)

wherein X, Y, R, R³, R⁴, R⁵, A, l, m and n have the meanings as defined herein, with a compound represented by the formula:

R⁶-L⁴ (XI)

wherein R⁶ has the same meanings as defined herein and L⁴ represents fluorine, chlorine, bromine, $C_{1-4}$ alkyl-carbonyloxy, $C_{1-4}$ alkoxy-carbonyloxy, azolyl, alkylsulfonyloxy, $C_{1-4}$ haloalkylsulfonyloxy, arylsulfonyloxy, if desired, in the presence of base.

Method (g) comprises reacting a compound represented by the formula (Ic) or formula (Ig):

(Ic)

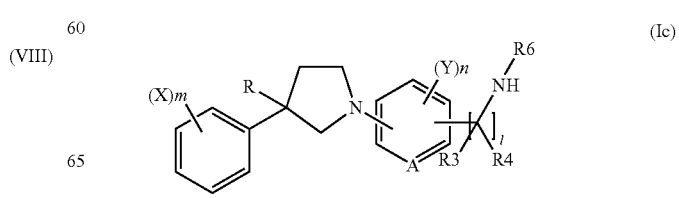

-continued

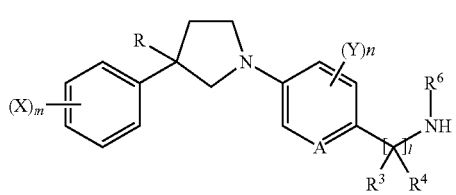
(Ig)

wherein X, Y, R, R³, R⁴, R⁶, A, l, m and n have the same meanings as defined herein, with a compound represented by the formula

R⁵-L⁴    (XII), wherein R⁵ and L⁴ have the same meanings as defined herein, if desired, in the presence of base.

Preparation method (h) for the preparation of compounds according to formula (I) or formula (Ia), wherein G stands for G1, G6 or G8:

Method (h) comprises reacting a compound represented by the formula (XIII) or formula (XIII-a):

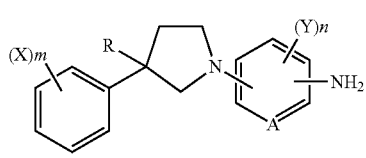
(XIII)

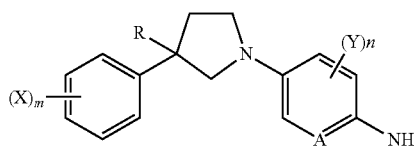
(XIII-a)

wherein X, Y, A, m and n have the same meanings as defined herein, with dialkoxytetrahydrofuran, 1,2-diformylhydrazine or sodium azide and trialkyl orthoformate.

Preparation method (i) for the preparation of compounds according to formula (I) or formula (Ia), wherein G stands for G2:

Method (i) comprises reacting a compound represented by the formula (XIV) or formula (XIV-a):

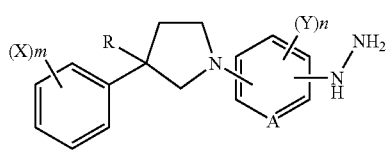
(XIV)

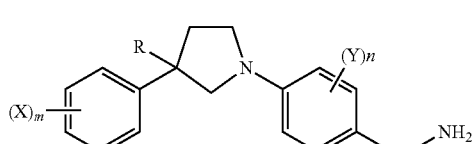
(XIV-a)

wherein X, Y, A, m and n have the same meanings as defined herein, with 1,1,3,3-tetra alkoxypropane.

Preparation method (j) for the preparation of compounds according to formula (I) or formula (Ia), wherein G stands for G2, G3, G4, G5, G6, G8 or G9:

Method (j) comprises reacting a compound represented by the formula (XV) or formula (XV-a):

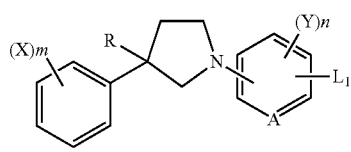
(Xa)

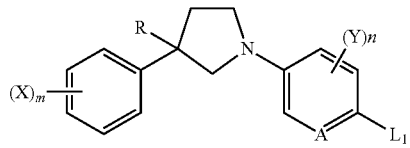
(XV-a)

wherein X, Y, R, A, m, n and L¹ have the same meanings as defined herein, with the protonated groups named G2, G3, G4, G5, G6, G8 or G9, namely G2-H, G3-H, G4-H, G5-H, G6-H or G8-H.

According to the present invention, aryl pyrrolidines of the above formula (I) or formula (Ia) of the invention exhibit a potent insecticidal action.

Above mentioned preparation method (a), when using, for example, 3-(3,5-dichlorophenyl)-3-(trifluoromethyl)pyrrolidine and N-(4-bromo-2-methylbenzyl)acetamide as starting materials, may be represented by the reaction formula below.

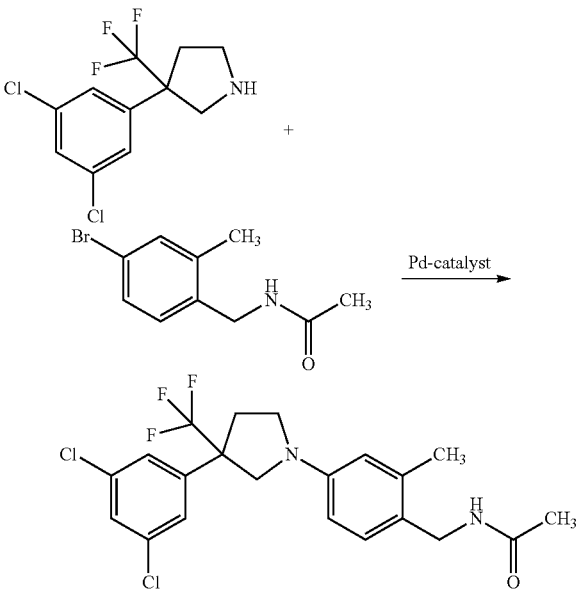

The preparation method (b), when using, for example, 4-[3-(3,5-dichlorophenyl)-3-(trifluoromethyl)pyrrolidin-1-yl]-2-nitrobenzoic acid and 2-picolylamine as starting materials, may be represented by the reaction formula below.

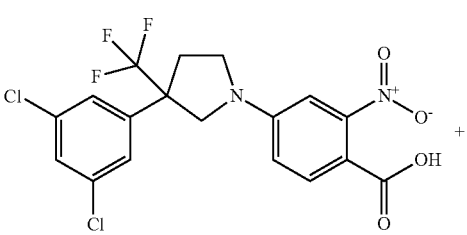

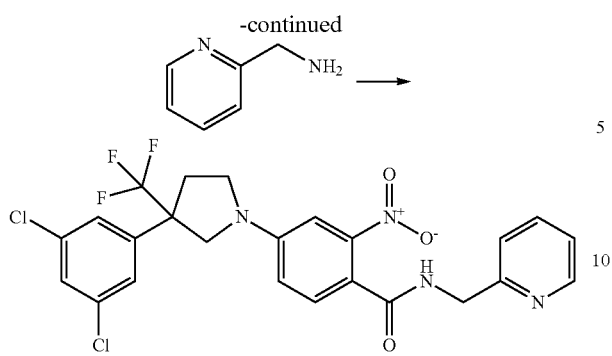

The preparation method (c), when using, for example, 4-[3-(3,5-dichlorophenyl)-3-(trifluoromethyl)pyrrolidin-1-yl]-2-nitro-N-(pyridine-2-yl-methyl)benzamide and iodomethane as starting materials, may be represented by the reaction formula below.

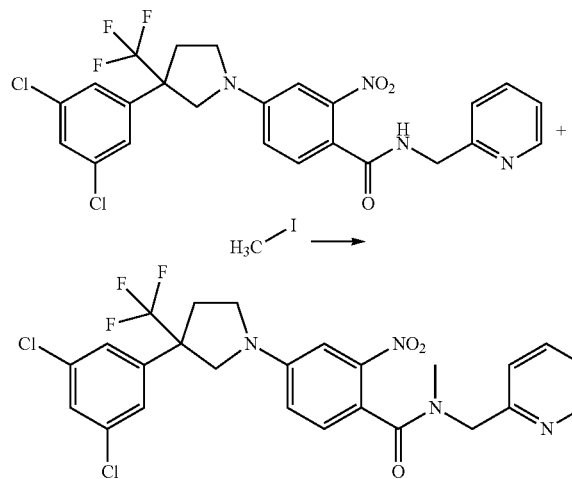

The preparation method (d), when using, for example, 2-chloro-4-[3-(3,5-dichlorophenyl)-3-(trifluoromethyl)pyrrolidin-1-yl]-N-(pyridine-2-yl-methyl)benzamide and Lawesson reagent as starting materials, may be represented by the reaction formula below.

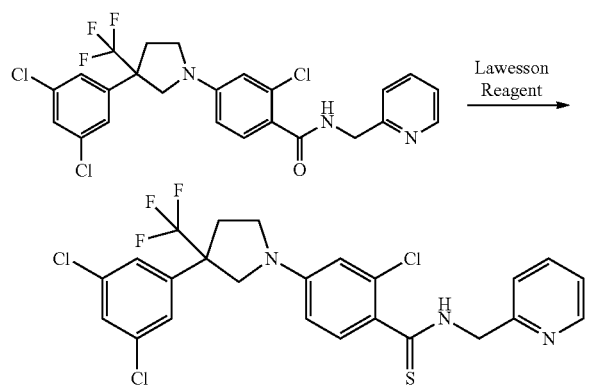

The preparation method (e), when using, for example, 1-[4-(bromomethyl)phenyl]-3-(3,5-dichlorophenyl)-3-(trifluoromethyl)pyrrolidine and benzamide as starting materials, may be represented by the reaction formula below.

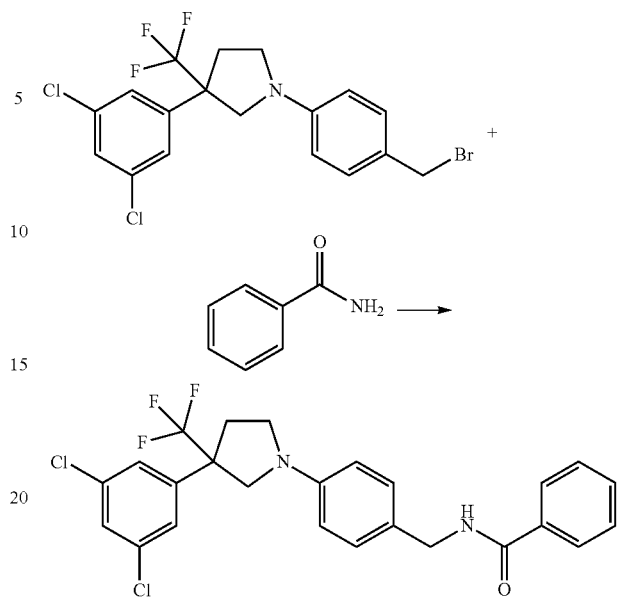

The preparation method (f), when using, for example, 1-{2-chloro-4-[3-(3,5-dichlorophenyl)-3-(trifluoromethyl)pyrrolidin-1-yl]phenyl}methanamine and acetyl chloride as starting materials, may be represented by the reaction formula below.

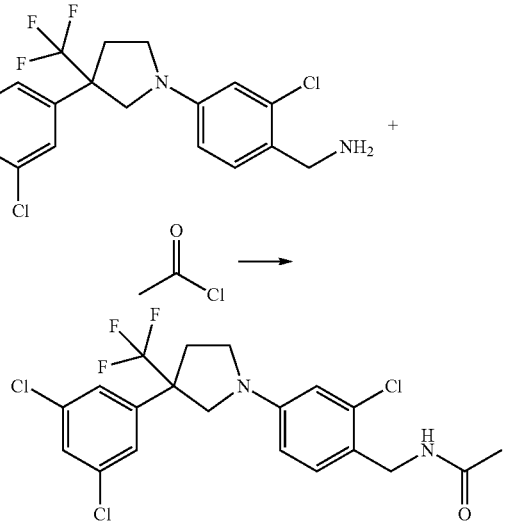

The preparation method (g), when using, for example, N-{2-chloro-4-[3-(3,5-dichlorophenyl)-3-(trifluoromethyl)pyrrolidin-1-yl]benzyl}acetamide and iodomethane as starting materials, may be represented by the reaction formula below.

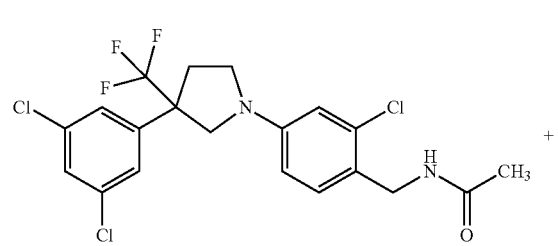

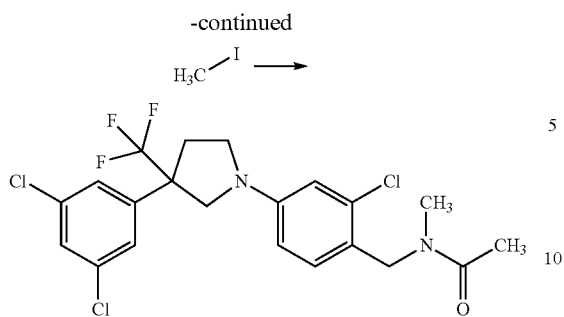

The preparation method (h), when using, for example, 4-[3-(3,5-dichlorophenyl)-3-(trifluoromethyl)pyrrolidin-1-yl) aniline and 2,5-dimethoxytetrahydrofuran as starting materials, may be represented by the reaction formula below.

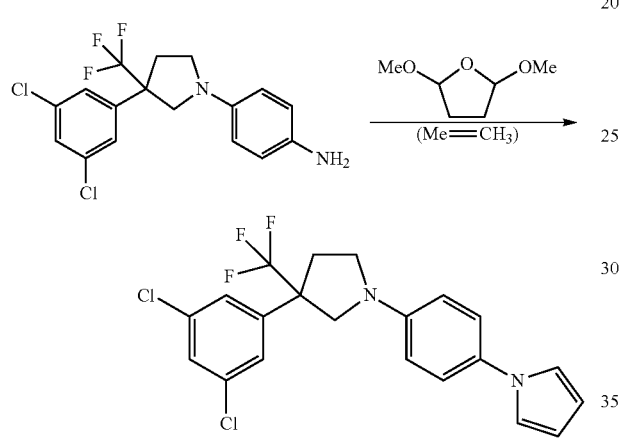

The preparation method (i), when using, for example, 3-(3,5-dichlorophenyl)-1-(4-hydrazinophenyl)-3-(trifluoromethyl)pyrrolidine and 1,1,3,3-tetraethoxypropane as starting materials, may be represented by the reaction formula below.

The preparation method (j), when using, for example, 5-(3,5-dichlorophenyl)-3-(trifluoromethyl)pyrrolidin-1-yl]-2-fluorobenzonitrile and 1H-1,2,4-triazole as starting materials, may be represented by the reaction formula below.

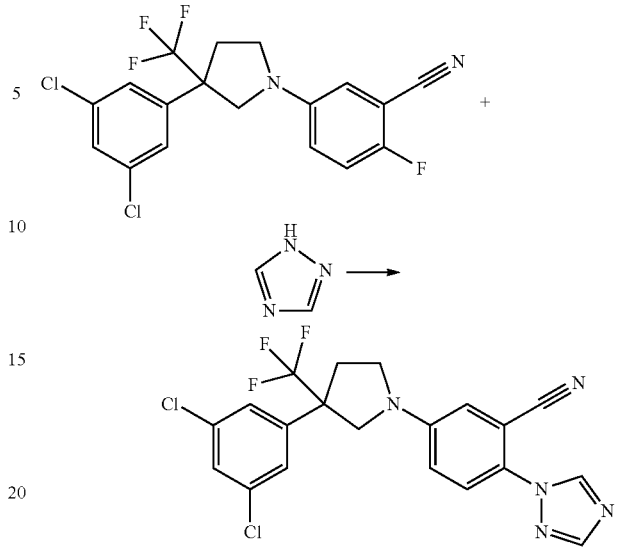

Many of the compounds of the formula (II), which are the starting materials in the preparation method (a), are novel compounds and may be synthesized by the method described below. The compound represented by the formula (XVI):

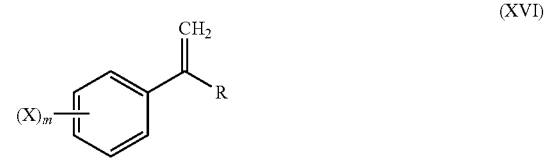

(XVI)

wherein X, m and R have the same meanings as defined herein is reacted with, for example, N-benzyl-1-methoxy-N-[(trimethylsilyl)methyl]methanamine in the presence of catalysts to obtain the compound represented by the formula (XVII) below:

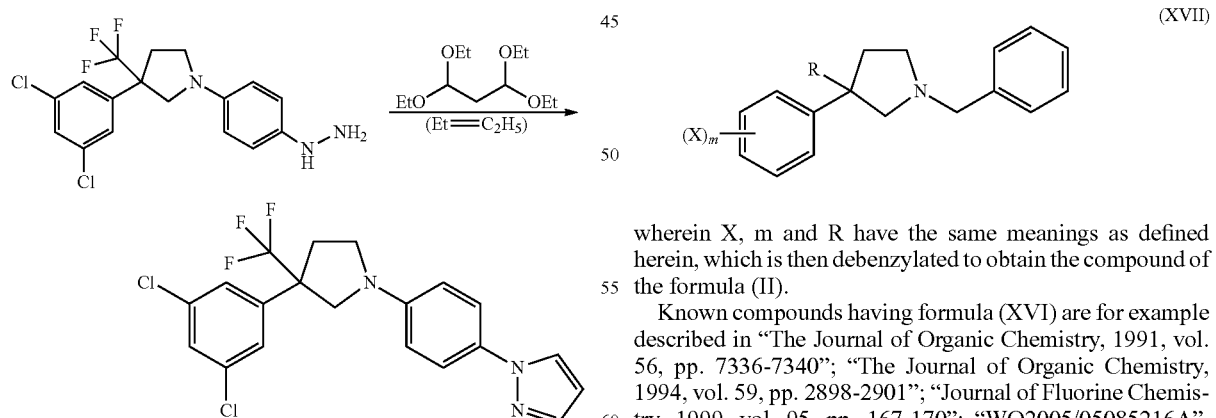

(XVII)

wherein X, m and R have the same meanings as defined herein, which is then debenzylated to obtain the compound of the formula (II).

Known compounds having formula (XVI) are for example described in "The Journal of Organic Chemistry, 1991, vol. 56, pp. 7336-7340"; "The Journal of Organic Chemistry, 1994, vol. 59, pp. 2898-2901"; "Journal of Fluorine Chemistry, 1999, vol. 95, pp. 167-170"; "WO2005/05085216A". Such compounds may also be synthesized by the methods described in these publications.

Representative examples of the compounds of the formula (XVI) include [1-(trifluoromethyl)vinyl]benzene; 1-chloro-3-[1-(trifluoromethyl)vinyl]benzene; 1-bromo-3-[1-(trifluoromethyl)vinyl]benzene; 1-nitro-3-[1-(trifluoromethyl)vinyl]benzene; 1-trifluoromethyl-3-[1-(trifluoromethyl)vinyl]

benzene; 1,3-difluoro-5-[1-(trifluoromethyl)vinyl]benzene; 1,3-dichloro-5-[1-(trifluoromethyl)vinyl]benzene; 1,3-difluoro-5-[1-(trifluoromethyl)vinyl]benzene; 1-fluoro-2-(trifluoromethyl)-4-[1-(trifluoromethyl)vinyl]benzene; 1,2,3-trichloro-5-[1-(trifluoromethyl)vinyl]benzene; or 1,3-dimethyl-2-nitro-5-[1-(trifluoromethyl)vinyl]benzene.

Instead of N-benzyl-1-methoxy-N-[(trimethylsilyl)methyl]methanamine in the above reaction, N-benzyl-1-butoxy-N-[(trimethylsilyl)methyl]methanamine or N-(butoxymethyl)-N-[(trimethylsilyl)methyl]cyclohexylamine may be used. These are well known compounds.

The catalysts used in the above reaction may include trifluoroacetic acid, trimethylsilyl trifluoromethansulfonate, iodotrimethylsilane, cesium fluoride and the like.

The above reaction may be performed according to the methods described in "Chemistry Letters, 1984, 1117-1120" and "Tetrahedron Letters, 1993, 34, 3279-3282", and the deprotection reaction such as debenzylation may be performed according to the methods described in "Journal of the Organic Chemistry, 1984, 49, 2081" and "PROTECTIVE GRLUOS in ORGANIC CHEMISTRY THIRD EDITION, JOHN WILEY & SONS, INC".

Representative examples of the compounds of the formula (II) in the preparation method (a) include: 3-(3,5-dichlorophenyl)-3-(trifluoromethyl)pyrrolidine; 3-[3,5-bis(trifluoromethyl)phenyl]-3-(trifluoromethyl)pyrrolidine; 3-(3,4,5-trichlorophenyl)-3-(trifluoromethyl)pyrrolidine; 3-(3,5-dimethyl-4-nitrophenyl)-3-(trifluoromethyl)pyrrolidine.

Many of the compounds of the formula (III) or formula (III-a), which are the starting materials in the preparation method (a), are known compounds, which may be synthesized by the methods well known in organic chemistry.

Representative examples of the compounds of the formula (III) and formula (III-a), respectively, include: N-(4-bromobenzyl)acetamide, N-(4-iodobenzyl)acetamide.

The reaction of the preparation methods (a), (b), (c), (d), (e), (f), (g), (h), (i) and (j) may be performed in a suitable diluent such as aliphatic hydrocarbons (e.g. hexane, cyclohexane, heptane etc.), aliphatic halogenated hydrocarbons (e.g. dichloromethane, chloroform, carbon tetrachloride, dichloroethane), aromatic hydrocarbons (e.g. benzene, toluene, xylene, chlorobenzene etc.), ethers (e.g. diethylether, dibutylether, dimethoxyethane (DME), tetrohydrofuran, dioxane etc.), esters (e.g. ethyl acetate, ethyl propionate etc.), amides (e.g. dimethylformamide (DMF), dimethylacetamide (DMA), N-methylpyrrolidone etc.), nitriles (e.g. acetonitrile, propionitrile etc.), dimethylsulfoxide (DMSO), water or mixed solvents thereof.

The reaction of the preparation methods (a), (b), (c), (d), (e), (f), (g), (h), (i) and (j) may be performed using the following bases such as alkali metal bases (e.g. lithium hydride, sodium hydride, potassium hydride, butyl lithium, tert-butyl lithium, trimethylsilyl lithium, lithium hexamethyldisilazide, sodium carbonate, potassium carbonate, cesium carbonate, tripotassium phosphate, sodium acetate, potassium acetate, sodium methoxide, sodium ethoxide, sodium-tert-butoxide and potassium-tert-butoxide etc.), organic bases (e.g. triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane, imidazole etc.).

The preparation methods (a), (b), (c), (d), (e), (f), (g), (h), (i) and (j) may be performed within in wide temperature range. Generally, it may be performed at the temperature in the range from about −78° C. to about 200° C., preferably from about −10° C. to about 150° C. Said reaction is preferably performed at normal pressure although it may be performed under light pressure or reduced pressure. The reaction time is from 0.1 to 72 hours, preferably from 0.1 to 24 hours.

The reaction of preparation method (a) may also be performed using suitable metal catalysts such as transition metal catalysts like for example $Pd_2(dba)_3$, $Pd_2(dba)_3CHCl_3$ (dba=dibenzylidene acetone), $Pd(OAc)_2$, CuI, or $Cu_2O$. If desired, it may be performed using phosphine ligands such as 2,2'-bis(diphenylphosphino)-1,1'-binaphtalene (BINAP), 4,5-bis(diphenylphosphino)-9,9-dimethylxanthene (Xantphos) tributylphosphine and the like or amine ligands such as 8-quinolinol, proline, N,N-dimethylglycine and the like.

In performing the preparation method (a), for example, 1 mole of the compound of the formula (II) is reacted with 1 to 3 moles of the compound of the formula (III) or formula (III-a) in the presence of 1 to 3 moles of base and catalytic amount of $Pd_2(dba)_3CHCl_3$ and Xantphos in a diluent such as toluene to obtain the respective compound of the formula (I) or formula (Ia) of the invention.

The compounds of the formula (IV) or formula (IV-a), which are used in the preparation method (b), are novel compounds. They can be synthesized by the methods described below. The compound of formula (II) may be reacted with a compound represented by the formula (XVIII):

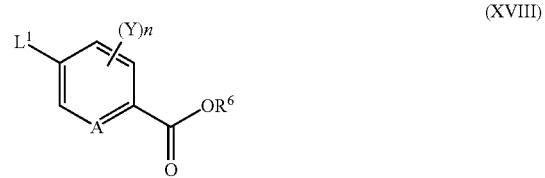

(XVIII)

wherein Y, A, n and $L^1$ have the same meanings as defined herein, $R^8$ represents hydrogen or $C_{1-4}$ alkyl, to obtain a compound represented by the formula (XIX) or formula (XIX-a):

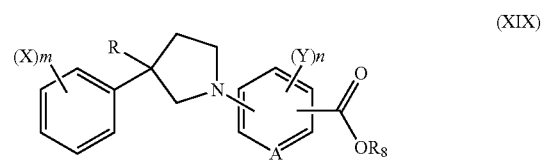

(XIX)

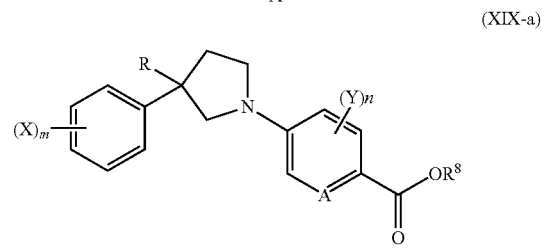

(XIX-a)

wherein X, Y, R, A, m, n and $R^8$ have the same meanings as defined herein. When $R^8$ represents $C_{1-4}$ alkyl, the compound of above formula (XIX) or formula (XIX-a) may be hydrolyzed to obtain the compound of the formula (IV) or formula (IV-a).

The compounds of the formula (XVIII) are known and include for example, the following compounds: methyl 4-iodobenzoate; methyl 4-bromo-2-methylbenzoate; ethyl 2-fluoro-4-iodobenzoate; methyl 2-chloro-4-iodobenzoate; methyl 2-bromo-4-iodobenzoate; methyl 4-fluoro-2-nitrobenzoate; and ethyl 4-fluoro-2-(trifluoromethyl)benzoate.

The compounds of the formula (V) or formula (V-a), which are the starting materials in the preparation method (b), are well known compounds.

For example, the compound of formula (IV) or formula (IV-a) may be easily obtained by the method comprising a reaction with a chlorinating agent such as thionyl chloride, oxalyl chloride or phosphorus pentachloride, or the method comprising a reaction with an organic halide such as pivaloyl chloride, or the method comprising a reaction with carbonyl diimidazole or sulfonyl imidazole etc.

Representative compounds of the formula (IV) and formula (IV-a), respectively, in the preparation method (b) include: 4-[3-(3,5-dichlorophenyl)-3-(trifluoromethyl)pyrrolidin-1-yl]benzoic acid; 4-[3-(3,5-dichlorophenyl)-3-(trifluoromethyl)pyrrolidin-1-yl]-2-nitrobenzoic acid; 4-{3-[3,5-bis(trifluoromethyl)phenyl]-3-(trifluoromethyl)pyrrolidin-1-yl}-2-nitrobenzoic acid; 4-[3-(3,5-dichlorophenyl)-3-(trifluoromethyl)pyrrolidin-1-yl]-2-(trifluoromethyl)benzoic acid and the like.

Representative compounds of the formula (V) and formula (V-a), respectively, include: 4-[3-(3,5-dichlorophenyl)-3-(trifluoromethyl)pyrrolidin-1-yl)benzoyl chloride; 4-(3-(3,5-dichlorophenyl)-3-(trifluoromethyl)pyrrolidin-1-yl]-2-nitrobenzoylchloride; 4-(3-[3,5-bis(trifluoromethylphenyl]-3-(trifluoromethyl)pyrrolidin-1-yl]-2-nitrobenzoyl chloride and the like.

The compounds of the formula (VI), which are the starting materials in the preparation method (b), are well known compounds.

Representative examples include: methylamine; ethylamine, cyclopropylamine, propargylamine, 2,2,2-trifluoroethylamine, 2-picolylamine, 3-aminomethyl-6-chloropyridine and the like.

The reaction of the preparation method (b) may be performed using the following condensation agents: 1,3-dicyclohexyl carbodiimide (DCC), 1-ethyl-3-(3'-dimethylaminopropyl)-carbodiimide hydrochloride (WSCI), carbonyldiimidazole (CDI), diethyl cyanophosphate (DEPC), 2-chloro-1-methylpyridinium iodide (Mukouyama Reagent) and the like.

In performing the preparation method (b), for example, 1 mole of the compound of the formula (IV) or formula (IV-a) may be reacted with 1 to 3 moles of the compound of the formula (VI) using 1 mole to 3 moles of a condensation agent and, if desired, with catalytic amount of an additive such as 1-hydroxybenzotriazole in a diluent (e.g. DMF) to obtain the corresponding compound of the formula (I) or formula (Ia).

The compounds of the formula (Ib) or formula (Ie), which are the starting materials in the preparation method (c), are encompassed in the formula (I) or formula (Ia) of the present invention obtained by preparation method (b).

The compounds of the formula (VII), which are the starting materials are well known compounds and specific examples include iodomethane, iodoethane and the like.

In performing the preparation method (c), for example, 1 mole of the compound of the formula (Ib) or formula (Ie) may be reacted with 1 to 5 moles of the compound of the formula (VII) in the presence of base in a diluent (e.g. THF) to obtain the corresponding compound of the formula (I) or formula (Ia).

The compounds of the formula (If) or formula (Id), which are the starting materials in the preparation method (d), are encompassed in the formula (I) or formula (Ia) of the present invention obtained by above preparation method (b) or (c).

Sulfurizing agents used in the preparation method (d) may include phosphorus pentasulfide, Lawesson reagent and the like.

In performing the preparation method (d), for example, 1 mole of the compound of the general formula (If) or formula (Id) may be reacted with 0.5 to 3 moles of Lawesson reagent in a diluent (e.g. toluene) to obtain the corresponding compound of the formula (I) or formula (Ia).

The compounds of the formula (VIII) or formula (VIII-b), which are the starting materials in the preparation method (e), are novel compounds and may be synthesized by the method below. The compound of above formula (XIX) or formula (XIX-a) may be reduced to obtain the compound represented by the formula (XX) or formula (XX-a):

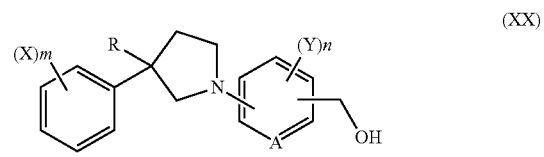

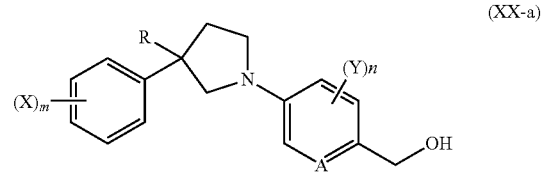

wherein X, Y, R, A, m and n have the same meanings as defined herein, which may be then subjected to a reaction such as halogenation or alkylsulfonylation in the usual manner to obtain the compound represented by the formula (VIII-a) or (VIII-c):

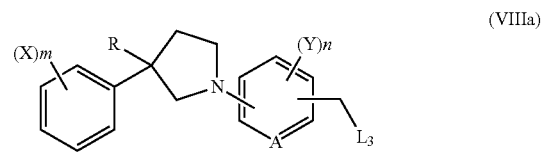

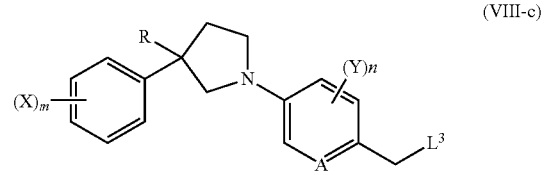

wherein X, Y, R, A, m, n and $L^3$ have the same definitions as above.

Representative examples of the compounds of the formula (VIII) and formula (VIII-b), respectively, in the preparation method (e) include: 1-[3-chloro-4-(chloromethyl)phenyl]-3-(3,5-dichlorophenyl)-3-(trifluoromethyl)pyrrolidine; 4-[3-(3,5-dichlorophenyl)-3-(trifluoromethyl)pyrrolidin-1-yl) benzylmethansulfonate; 1-[3-bromo-4-(chloromethyl) phenyl]-3-(3,5-dichlorophenyl)-3-(trifluoromethyl) pyrrolidine and the like.

The compounds of the formula (IX), which are the starting materials in the preparation method (e), are well known compounds and representative examples include: acetoamide; propionamide; benzamide; 2-chlorobenzamide; 3-chlorobenzamide; 4-chlorobenzamide and the like.

In performing the preparation method (e), for example, 1 mole of the compound of the formula (VIII) or formula (VIII-b) may be reacted with 1 to 3 moles of the formula (IX) in the presence of base in a diluent (e.g. THF) to obtain the corresponding compound of the formula (I) or formula (Ia).

The compounds of the formula (X), or formula (X-a) which are the starting materials in the preparation method (f), are novel compound and may be obtained by reacting a compound of formula (VIII) or formula (VIII-b) with a compound R⁵—NH₂ (XXI) wherein R₅ has the same meanings as defined herein.

The compounds of the formula (X) or formula (X-a) wherein 1 is 1 may be also synthesized by the alternative method comprising reacting a compound of above formula (II) with a compound represented by the formula (XXII):

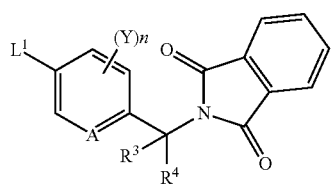

(XXII)

wherein Y, A, R³, R⁴, n and L¹ have the same meanings as defined herein, to obtain the compound represented by the formula (XXIII) or formula (XXIII-a):

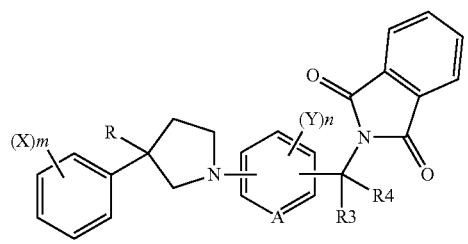

(XXIII)

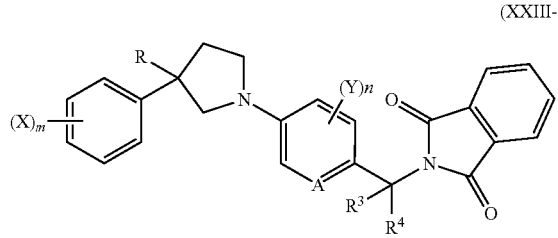

(XXIII-a)

wherein X, Y, R, A, m, n, R³ and R⁴ have the same meanings as defined herein, which is then reacted according to Gabriel synthetic reaction.

The compounds of above formula (XXII) are known compounds and include: 2-(4-bromobenzyl)-1H-isoindole-1,3(2H)-dione; 2-(4-bromo-2-nitrobenzyl)-1H-isoindole-1,3(2H)-dione; 2-(4-iodobenzyl)-1H-isoindole-1,3(2H)-dione; 2-(4-iodo-2-nitrobenzyl)-1H-isoindole-1,3(2H)-dione; 2-(2-chloro-4-iodobenzyl)-1H-isoindole-1,3(2H)-dione.

The compounds of the formula (X) or formula (X-a) wherein R³, R⁴ and R⁵ represent hydrogen may be easily synthesized by the alternative method comprising usual reduction reaction of the nitrile compound represented by the formula (XXIV) or formula (XXIV-a):

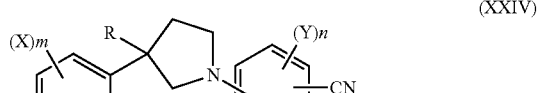

(XXIV)

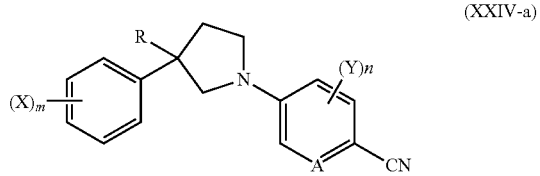

(XXIV-a)

wherein X, Y, R, m and n have the same meanings as defined herein.

The compounds of above formula (XXIV) or formula (XXIV-a) are novel compounds and may be obtained as shown in the synthetic example 8 described below.

Representative examples of the compounds of the formula (X) and formula (X-a), respectively, in the preparation method (f) include: 1-(2-chloro-4-[3-(3,5-dichlorophenyl)-3-(trifluoromethyl)pyrrolidin-1-yl]phenyl)methanamine; 1-{2-bromo-4-[3-(3,5-dichlorophenyl)-3-(trifluoromethyl)pyrrolidin-1-yl]phenyl}methanamine and the like.

The compounds of the formula (XI), which are the starting materials in the preparation method (f), are well known compounds, and the specific examples include: acetyl chloride; propionyl chloride; benzoyl chloride; 2-chlorobenzoyl chloride; 3-chlorobenzoyl chloride; 4-chlorobenzoyl chloride; nicotinoylchloride hydrochloride and the like.

In performing the preparation method (f), for example, 1 mole of the compound of the formula (X) formula (X-a) may be reacted with 1 to 3 moles of the formula (XI) in the presence of base in a diluent (e.g. THF) to obtain the corresponding compound of the formula (I) or formula (Ia).

The compounds of the formula (Ic) or formula (Ig), which are the starting materials in the preparation method (g), are encompassed in the formula (I) or formula (Ia) of the present invention obtained by above preparation method (e) or (f).

The compounds of the formula (XII), which are the starting materials are well known and the specific examples include iodomethane, iodoethane, acetyl chloride and the like.

In performing the preparation method (g), for example, 1 mole of the compound of the formula (Ic) or formula (Ig) may be reacted with 1 to 3 moles of the formula (XII) in the presence of base in a diluent (e.g. THF) to obtain the corresponding compound of the formula (I) or formula (Ia).

The compounds of the formula (XIII) or formula (XIII-a), which are the starting materials in the preparation method (h), are novel compounds and may be synthesized by the method described below.

More specifically, the compound of above formula (II) is reacted with a compound represented by the formula (XXV) or formula (XXV-a):

(XXV)

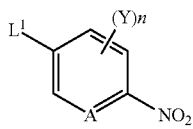

wherein Y, A, n and $L^1$ have the same meanings as defined herein, to obtain a compound represented by the formula (XXVI) or formula (XXVI-a):

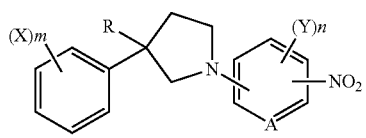

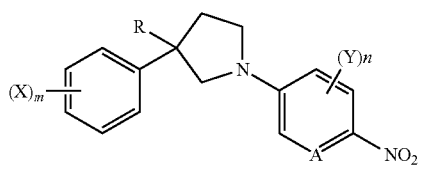

wherein X, Y, R, A, m and n have the same meanings as defined herein, which is then reduced to obtain the compound of the formula (XIII) or formula (XIII-a).

The specific examples of compounds of formula (XXV) and formula (XXV-a) include; 2-fluoro-4-nitrobenzene; 2-bromo-4-nitrobenzene; 2-iodo-4-nitrobenzene; 2-bromo-4-fluoronitrobenzene; 4-fluoro-2-methylnitrobenzene and the like.

Representative examples of the compounds of the formula (XIII) and formula (XIII-a), espectively, in the preparation method (h) include: 4-[3-(3,5-dichlorophenyl)-3-(trifluoromethyl)pyrrolidin-1-yl]aniline; 2-bromo-4-[3-(3,5-dichlorophenyl)-3-(trifluoromethyl)pyrrolidin-1-yl]aniline and the like.

Dialkoxy tetrahydrofurans, which are the starting materials in the preparation method (h), are known compounds and the specific examples include: 2,5-dimethoxytetrahydrofuran; 2,5-diethoxytetrahydrofuran and the like.

In performing above preparation method (h), for example, 1 mole of the compound of the formula (XIII) or formula (XIII-a) may be reacted with 1 to 5 moles of 2,5-dimethoxytetrahydrofuran in a diluent (e.g. acetic acid) to obtain the corresponding compound of the formula (I) or formula (Ia) of the present invention.

In the preparation method (h), said reaction, when using 1,2-diformylhydrazine, may be performed in the presence of base and trialkylhalosilane.

The examples of the base may include organic bases such as triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane, imidazole etc.

Representative examples of trialkylhalosilanes include: trimethylchlorosilane; triethylchlorosilane; trimethylbromosilane and the like.

In performing the preparation method (h), 1 mole of the compound of the formula (XIII) or formula (XIII-a) may be reacted with 1 to 5 moles of 1,2-diformylhydrazine, 1 to 10 moles of base and 1 to 25 moles of trialkylhalosilane in great excess amount of pyridine to obtain the desired corresponding compound of the formula (I) or formula (Ia).

In the case of the reaction of sodium azide with trialkyl orthoformate in the preparation method (h), the examples of trialkyl orthoformates may include trimethyl orthoformate and triethyl orthoformate and the like.

In performing the preparation method (h), 1 mole of the compound of the formula (XIII) or formula (XIII-a) may be reacted with 1 to 3 moles of sodium azide and 1 to 10 moles of trialkyl orthoformate in a diluent (e.g. acetic acid) to obtain the corresponding compound of the formula (I) or formula (Ia) of the invention.

The compounds of the formula (XIV) or formula (XIV-a), which are the starting materials in the preparation method (i), are novel compounds and may be synthesized by the method described below. More specifically, the compound of above formula (XIII) or formula (XIII-a) is subjected to Sandmeyer's reaction, which is known in the field of organic chemistry, followed by reduction to obtain the compound of the formula (XIV) or formula (XIV-a).

Representative examples of the compounds of the formula (XIV) and formula (XIV-a), respectively may include: 3-(3,5-dichlorophenyl)-1-(4-hydrazinophenyl)-3-(trifluoromethyl)pyrrolidine; 3-(3,5-dichlorophenyl)-1-(4-hydrazino-3-methylphenyl)-3-(tri-fluoromethyl)pyrrolidine and the like.

2,5-Dialkoxy tetrahydrofurans, which are used as starting material in the preparation method (i), are known compounds and representative examples include: 1,1,3,3-tetramethoxypropane; 1,1,3,3-tetraethoxypropane and the like.

In performing above preparation method (i), for example, 1 mole of the compound of the formula (XIV) or formula (XIV-a) may be reacted with 1 to 5 moles of 1,1,3,3-tetraalkoxypropane with, if desired, addition of catalytic amount of acid such as sulfuric acid in a diluent (e.g. ethanol) to obtain the corresponding compound of the formula (I) or formula (Ia) of the invention.

The compounds of the formula (XV) or formula (XV-a), which are the starting material in the preparation method (j), are novel compounds and may be synthesized by the method described below. More specifically, the compound of above formula (II) is reacted with a compound represented by the formula (XXVII) or formula (XXVII-a)

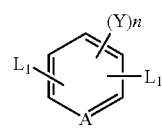

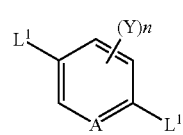

wherein Y, A, n and $L^1$ have the same meanings as defined herein, to obtain the compound of the formula (XV) or formula (XV-a).

The specific examples of compounds of above formula (XXVII) and formula (XXVII-a), respectively, include: 2-fluoro-5-iodobenzonitrile; 5-bromo-2-fluorobenzonitrile; 1-chloro-4-iodo-2-nitrobenzene; 1,4-dibromobenzene; 1,4-diiodo benzene and the like.

Representative examples of the compounds of the formula (XV) and formula (XV-a), respectively in the preparation method (j) may include: 5-[3-(3,5-dichlorophenyl)-3-(trifluoromethyl)pyrrolidin-1-yl]-2-fluorobenzonitrile; 5-{3-[3,5-bis(trifluoromethyl)phenyl]-3-(trifluoromethyl)pyrrolidin-1-yl}-2-fluorobenzonitrile and the like.

Many of the compounds represented by the formula G2-H, G3-H, G4-H, G5-G, G6-H, G8-H, G9-H, which are the starting materials in the preparation method (j), are known compounds and the specific examples may include: 1H-imidazole; 1H-pyrazole; 4-methyl-1H-pyrazole; 4-fluoro-1H-pyrazole; 4-chloro-1H-pyrazole; 4-bromo-1H-pyrazole; 4-iodo-1H-pyrazole; 4-nitro-1H-pyrazole; 4-methyl-1H-pyrazole; 3-trifluoromethyl-1H-pyrazole; 4-trifluoromethyl-1H-pyrazole; 4-cyano-1H-pyrazole; 1H-1,2,3-triazole; 1H-1,2,4-triazole; 1H-tetrazole; 5-methyl-1H-tetrazole; 5-(methylthio)-1H-tetrazole and the like.

In performing the preparation method (j), for example, 1 mole of the compound of the formula (XV) or formula (XV-a) may be reacted with 1 to 3 moles of G6-H in the presence of 1 to 3 moles of base in a diluent (e.g. DMF) to obtain the corresponding compound of the formula (I) or formula (Ia) of the invention.

In preparation methods of the compounds of the formula (I) or formula (Ia) of the present invention, novel materials among the compounds which are the raw materials (starting materials and intermediates) can be collectively represented by the formula described below.

Formula (II-a)

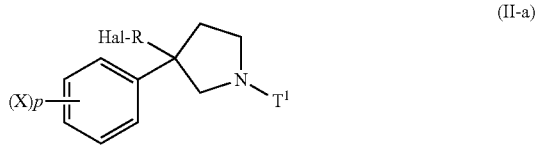

(II-a)

wherein X has the same meanings as defined herein, $T^1$ represents hydrogen or benzyl, Hal-R represents haloalkyl and p represents 1, 2, 3, 4 or 5.

Formula (XVI-a)

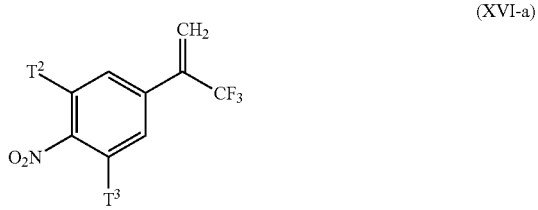

(XVI-a)

wherein $T^2$ and $T^3$ each independently represent alkyl.

Compounds of Formula (XXVIII) or compounds of formula (XXVIII-a)

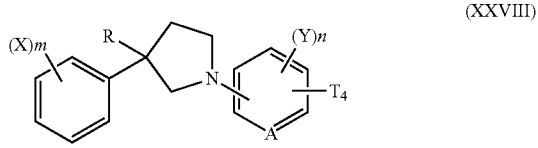

(XXVIII)

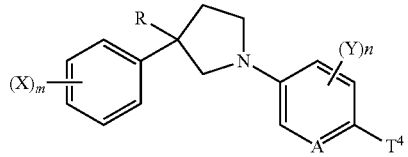

(XXVIII-a)

wherein X, Y, R, A, m and n has the same definition as above, $T^4$ represents:

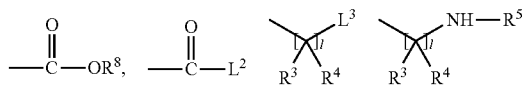

cyano, amino or nitro, $R^8$, $L^2$, $L^3$, $R^3$, $R^4$ and $R^5$ have the same meanings as defined herein.

The compounds according to the present invention have potent insecticidal and acaricidal activity. Therefore, the compounds represented by formula (I) or formula (Ia) of the present invention can be used as insecticides and/or acaricides. They are particularly useful in the agricultural field. The compounds according to the present invention also exert an appropriate controlling effect against harmful insects without phytotoxicity against cultured plants. In addition, the compounds of the present invention can be used for controlling a wide variety of pests including, for example, harmful sucking insects, biting insects and other plant-parasitic pests, stored grain pests and hygienic pests as well as pests in the veterinary field and can be applied for their control, in particular eradication and extermination. Therefore, the present invention also encompasses a method for combating harmful pests.

Such pest insects include for example

Beetles, such as adzuki bean beetle (*Callosobruchus Chinensis*), maize weevil (*Sitophilus zeamais*), red flour beetle (*Tribolium Castaneum*), large 28-spotted lady beetle (*Epilachna vigintioctomaculata*), barley wireworm (*Agriotes fuscicollis*), soy bean beetle (*Anomala rufocuprea*), colorado potato beetle (*Leptinotarsa decemlineata*), diabrotica (*Diabrotica* spp.), Japanese pine sawyer (*Monochamus alternatus*), rice water weevil (*Lissorhoptrus oryzophilus*), powderpost beetle (*Lyctus bruneus*), cucurbit leaf beetle (*Aulacophora femoralis*).

Lepidopteran pests, such as gypsy moth (*Lymantria dispar*), tent caterpillar (*Malacosoma neustria*), small white (*Pieris rapae*), common cutworm (*Spodoptera litura*), cabbage moth (*Mamestra brassicae*), Striped Rice Borer (*Chilo suppressalis*), corn borer (*Pyrausta nubilalis*), dried currant moth (*Ephestia cautella*), summer fruit tortrix moth (*Adoxophyes orana*), codling moth (*Carpocapsa pomonella*), common cutworm moth (*Agrotis fucosa*), wax moth (*Galleria mellonella*), diamondback moth (*Plutella maculipennis*), Heliothis (*Heliothis virescens*), citrus leafminer (*Phyllocnistis citrella*).

Hemipterous pests, such as Been rice leafhopper (*Nephotettix cincticeps*), brown planthopper (*Nilaparvata lugens*), comstock mealybug (*Pseudococcus comstocki*), arrowhead scale (*Unaspis yanonensis*), Momoaka-aburamusi (*Myzus persicas*), Green apple aphid (*Aphis pomi*), cotton aphid (*Aphis gossypii*), turnip aphid (*Phopalosiphum pseudobrassicas*), Nashi-gunbai (*Stephanitis nashi*), Nazara (*Nazara* spp.), greenhouse whitefly (*Trialcurodes vaporariorm*), Pshylla (*Pshylla* spp.).

Thripid pests, such as melon thrips (*Thrips palmi*), western flower thrip (*Frankliniella occidentalis*).

Orthopteran pests, such as german Cockroach (*Blatella germanica*), american cockroach (*Periplaneta americana*), mole cricket (*Gryllotalpa africana*), migratory locust (*Locusts migratoria* migratoriaodes)

Isoptera pests, such as Japanese subterranean termite (*Reticulitermes speratus*), termite (*Coptotermes formosanus*);

Dipterous pests, such as house fly (*Musca domestics*), yellow fever mosquito (*Aedes aegypti*), bean seed fly (*Hylemia platura*), Aka-ie-ka (*Culex pipiens*), Sina-hamadara-ka (*Anopheles sinensis*), kodaka-aka-ie-ka (*Culex tritaeniorhychus*), american serpentine leafminer (*Liriomyza trifolii*).

Mites, such as Nise-nami-hadani (*Tetranychus cinnabarinus*), Nami-ha-dani (*Tetrahychus urticae*), citrus red mite (*Panonychus citri*), pink citrus rust mite (*Aculops pelekassi*), Tarsonemus (*Tarsonemus* spp.).

Nematode pests, such as sweet potato root-knot nematode (*Meloidogyne incognita*), pine wood nematode (*Bursaphelenchus lignicolus* Mamiya et Kiyohara), rice nematode (*Aphelenchoides besseyi*), soybean cyst nematode (*Heterodera glycines*), meadow nematode (*Pratylenchus* spp.).

Additionally, the compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, in the hygiene and animal health sector. They may be preferably employed as plant protection agents. They are active against normally sensitive and resistant species and against all or some stages of development. The pests which can be combated by using the compounds and compositions according to the invention further include inter alia:

From the order of the Anoplura (*Phthiraptera*), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eotetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus orator, Hylamorpha elegans, Hylotrupes bajulus, Hypera postica, Hypothenemus* spp., *Lachnosterna con-*

*sanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.; as well as *Callosobruchus Chinensis, Sitophilus zeamais, Tribolium Castaneum, Epilachna vigintioctomaculata, Agriotes fuscicollis, Anomala rufocuprea, Leptinotarsa decemlineata, Diabrotica* spp., *Monochamus alternatus, Lissorhoptrus oryzophilus, Lyctus bruneus*, and *Aulacophora femoralis.*

From the order of the Collembola, for example, *Onychiurus armatus.*

From the order of the Dermaptera, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Taenia* spp., *Tipula paludosa, Wohlfahrtia* spp.; as well as *Musca domestica, Aedes aegypti, Hylemia platura, Culex pipiens, Anopheles sinensis, Culex tritaeniorhychus* and *Liriomyza trifolii.*

From the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta*

*persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Cameocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Reticulitermes* spp., *Odontotermes* spp.; as well as *Reticulitermes speratus* and *Coptotermes formosanus.*

From the order of the Lepidoptera, for example, *Acronicta major, Aedia teucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flanunea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.; as well as *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotis fucosa, Galleria mellonella, Plutella maculipennis, Heliothis virescens* and *Phyllocnistis citrella.*

From the order of the Orthoptera, for example, *Acheta domesticus, Blatta orientalis, Gryllotalpa* spp., *Leucophaea maderae, Locusta* spp., *Melanoplus* spp., *Schistocerca gregaria*; as well as *Blattella germanica, Periplaneta americana, Gryllotalpa africana* and *Locusta migratoria* migratoriaodes.

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Enneothrips Havens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.; as well as *Thrips palmi* and *Frankliniella occidentalis.*

From the order of Hemiptera, for example, *Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nazara* spp., *Trialeurodes vaporariorm* and *Pshylla* spp.;

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Radopholus similis, Rotylenchus* spp., *Trichodorus* spp., *Tylenchorhynchus* spp., *Tylenchulus* spp., *Tylenchulus semipenetrans, Xiphinema* spp.; as well as *Meloidogyne incognita, Bursaphelenchus lignicolus* Mamiya et Kiyohara, *Aphelenchoides besseyi,* and *Heterodera glycines* and *Pratylenchus* spp.

Mites include, for example, *Tetranychus cinnabarinus, Tetranychus urticae, Panonychus citri, Aculops pelekassi* and *Tarsonemus* spp. or Mites, such as *Ornithodoros* spp., *Ixodes* spp., *Boophilus* spp. and the like.

In the present invention, substances having insecticidal effects against vermins encompassing all of such pests are referred to as insecticides.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active compounds.

In the veterinary field, the novel compounds of the invention can be effectively used to various harmful animal parasites (endoparasites and ectoparasites), including insects and worms.

Examples of such animal parasites may include the following vermins: insects, such as bot fly (*Gastrophilus* spp.), stable fly (*Stomoxys* spp.), biting louse (*Trichodectes* spp.), Rhodnius (*Rhodnius* spp.), inu-nomi (*Ctenocephalides canis*), bedbug (*Cimx lecturius*), neko-nomi (*Ctenocephalides felis*), sheep blowfly (*Lucilia cuprina*) and the like.

As already mentioned before, in the veterinary fields, i.e. in the field of veterinary medicine, the active compounds according to the present invention are active against animal parasites, in particular ectoparasites or endoparasites. The term endoparasites includes in particular helminths, such as cestodes, nematodes or trematodes, and protozoae, such as coccidia. Ectoparasites are typically and preferably arthropods, in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like.

These parasites include;

From the order of the Anoplurida, for example *Haematopinus* spp., *Linognathus* spp., *Pediculus* spp., *Phtirus* spp., *Solenopotes* spp.; particular examples are: *Linognathus setosus, Linognathus vituli, Linognathus ovillus, Linognathus oviformis, Linognathus pedalis, Linognathus stenopsis, Haematopinus asini macrocephalus, Haematopinus eurystemus, Haematopinus suis, Pediculus humanus capitis, Pediculus humanus corporis, Phylloera vastatrix, Phthirus pubis, Solenopotes capillatus.*

From the order of the Mallophagida and the suborders Amblycerina and Ischnocerina, for example *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.; particular examples are: *Bovicola bovis, Bovicola ovis, Bovicola limbata, Damalina bovis, Trichodectes canis, Felicola subrostratus, Bovicola caprae, Lepikentron ovis, Werneckiella equi.*

From the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *lthinoestrus* spp., *Tipula* spp.; particular examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Ilybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricomis, Gasterophilus pecorum, Braula coeca.*

From the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides felis, Pulex irritans, Tunga penetrans, Xenopsylla cheopis.*

From the order of the Heteropterida, for example *Cimex* spp., *Triatoma* spp., *Rhodnius* spp., *Panstrongylus* spp.

From the order of the Blattarida, for example *Blatta orientalis, Periplaneta americana, Blattela germanica, Supella* spp. (e.g. *Suppella longipalpa*).

From the subclass of the Acari (Acarina) and the orders of the Meta- and Mesostigmata, for example *Argas* spp., *Omithodorus* spp., *Otobius* spp., *Ixodes* spp., *Amblyomma* spp., *Rhipicephalus* (*Boophilus*) spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Omithodorus moubata, Otobius megnini, Rhipicephalus* (*Boophilus*) *microplus, Rhipicephalus* (*Boophilus*) *decoloratus, Rhipicephalus* (*Boophilus*) *annulatus, Rhipicephalus* (*Boophilus*) *calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Nodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicomi, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zarnbeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni.*

From the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakci, Demodex canis, Demodex bovis, Demodex ovis, Demodex caprae, Demodex equi, Demodex caballi, Demodex suis, Neotrombicula autumnalis, Neotrombicula desaleri, Neoschtingastia xerothermobia, Trombicula akamushi, Otodectes cynotis, Notoedres cati, Sarcoptis canis, Sarcoptes bovis, Sarcoptes ovis, Sarcoptes rupicaprae* (=*S. caprae*), *Sarcoptes equi, Sarcoptes suis, Psoroptes ovis, Psoroptes cuniculi, Psoroptes equi, Chorioptes bovis, Psoergates ovis, Pneumonyssoidic Mange, Pneumonyssoides caninum, Acarapis woodi.*

The active compounds according to the invention are also suitable for controlling arthropods, helminths and protozoae, which attack animals. The control of arthropods is preferred. The control of insects is particularly preferred. Equally, the control of acarids is particularly preferred.

Animals which may be treated to control the parasites include birds, insects and in particular mammals. Animals includeagricultural livestock such as, for example, cattle, sheep, goats, horses, pigs, donkeys, camels, buffaloes, rabbits, chickens, fur-bearing animals, turkeys, ducks, geese, cultured fish, honeybees. Moreover, animals include domestic animals—also referred to as companion animals—such as, for example, dogs, cats, ferrets, cage birds, aquarium fish, reptiles and what are known as experimental animals such as, for example, hamsters, guinea pigs, rats and mice.

By controlling these arthropods, helminths and/or protozoae, it is intended to reduce deaths and improve performance (in the case of meat, milk, wool, hides, eggs, honey and the like) and health of the host animal, so that more economical and simpler animal keeping is made possible by the use of the active compounds according to the invention.

For example, it is desirable to prevent or interrupt the uptake of blood by the parasites from the hosts (when applicable). Also, controlling the parasites may help to prevent the transmittance of infectious agents.

The term "controlling" as used herein with regard to the veterinary field, means that the active compounds are effective in reducing the incidence of the respective parasite in an animal infected with such parasites to innocuous levels. More specifically, "controlling", as used herein, means that the active compound is effective in killing the respective parasite, inhibiting its growth, or inhibiting its proliferation.

The active compounds of the present invention, when used as insecticides, may be formed into conventional formulation forms. Such formulation forms include, for example, solutions, emulsions, wettable powders, water dispersible granules, suspensions, powders, foams, pastes, tablets, granules, aerosols, active compound-impregnated natural and synthetic substances, microcapsules, seed coating agents, formulations used with burning device (burning devices include, for example, fumigation and smoking cartridges, cans and coils) and UVL [cold mist, warm mist].

The active compounds of the formula (I) or formula (Ia) of the invention may be present in the commercially useful formulations and usage forms prepared from their formulations, as a mixed formulation form with other active compounds such as insecticides, toxic baits, bactericides, acaricides, nematocides, fungicides, growth regulating agents, herbicides and the like. Above mentioned insecticides may include, for example, organophosphorus agents, carbamate agents, carboxylate chemical agents, chlorohydrocarbon type chemical agents, insecticidal substances produced by microorganisms and the like.

These formulations may be prepared by the method known per se. For example, they can be prepared by mixing the active compounds together with spreading agents, i.e. liquid diluents or carriers; Liquefied gas diluents or carriers; solid diluents or carriers, and, optionally, surfactants i.e. emulsifiers and/or dispersants and/or foam forming agents.

When water is used as a spreading agent, for example organic solvents may be used as an auxiliary solvent.

Liquid diluents or carriers may include, for example, aromatic hydrocarbons (e.g. xylene, toluene, alkylnaphthalene etc.), chlorinated aromatic or chlorinated aliphatic hydrocarbons (e.g. chlorobenzens, ethylene chlorides, methylene chlorides etc.), aliphatic hydrocarbons (e.g. cyclohexanes or paraffins (e.g. mineral oil fractions)), alcohols (e.g. butanol, glycol and ethers or esters thereof etc.), ketones (e.g. acetone, methylethylketone, methylisobutylketone, cyclohexanone etc.), strong polar solvents (e.g. dimethylformamide, dimethylsulfoxide etc.), water and the like.

Liquefied gas diluents or carriers may include substances which exist as gas at ambient temperature and normal pressure, for example aerosol propellants such as furan, propane, nitrogen gas, carbon dioxide, halogenated hydrocarbons.

Solid diluents may include, for example, crushed natural minerals (e.g. kaolin, clay, talc, chalk, quartz, attapulgite, montmorillonite or diatom earth etc.), crushed synthetic minerals (e.g. highly-dispersive silic acid, alumina, silicate etc.) and the like.

Solid carriers for granules may include, for example, crushed and fractionated rocks (e.g. calcite, marble, pumice stone, sepiolite, dolomite etc.), synthetic granules of inorganic or organic powders, fine particles of organic materials (e.g. sawdust, coconut shells, corncob, stalk of Indian weed etc.).

Emulsifiers and/or foams may include, for example, nonionic or anionic emulsifiers (e.g. polyoxyethylene fatty acid esters, polyoxyethylene fatty alcohol ethers (e.g. alkylarylpolyglycol ether), alkyl sulfonates, alkyl sulfates, aryl sulfonates etc.), albumin hydrolyzed products and the like.

Examples of dispersants include, for example, lignin sulfite waste liquor, methylcellulose and the like.

Adhesive agents may also be used for the formulations (powders, granules, emulsions), such as carboxymethylcellulose, natural or synthetic polymers (e.g. acacia, polyvinyl alcohols, polyvinyl acetates etc.) and the like.

Colorants may be used, such as inorganic pigments (e.g. ferric oxide, titanic oxide, Prussian blue etc.), organic pigments (e.g. alizarin dyes, azo dyes or metallophthalocyanine dyes etc.) as well as trace elements (e.g. salts of iron, manganese, boron, cupper, cobalt, molybdenum or zinc etc.).

Generally such formulations may contain the active compounds described above in a range from 0.1 to 95% by weight, preferably 0.5 to 90% by weight.

The compounds according to the present invention may be used in ordinary manners suitable for their application forms. It is understood that the compounds according to the invention can also be present in compositions containing further ingredients, such as auxiliaries or active ingredients. The skilled person will choose a suitable ingredient among those named herein and known in the art and which are supposed to enhance a property which is considered being favorable in view of the intended application and use.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof, are treated. The terms "parts", "parts of plants" and "plant parts" have been explained above.

Particularly preferably, plants of the plant cultivars which are in each case commercially available or in use are treated according to the invention. Plant cultivars are understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive "synergistic" effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are the increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds or compositions according to the invention. The preferred ranges stated above for the active compounds or compositions also apply to the treatment of these plants. Particular emphasis is given to the treatment of plants with the compounds or compositions specifically mentioned in the present text.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticomis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharine.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the *Opiliones*, for example, *Pseudoscorpiones chelifer, Pseudoscorpiones cheiridium, Opiliones phalangium*.

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Diana orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga eamaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of domestic insecticides, a combination with other suitable active compounds, such as phosphoric esters, carbamates, pyrethroids, neonicotinoids, growth regulators or active compounds from other known classes of insecticides can be used and is especially preferable.

The compounds or compositions according to the invention, preferable in their suitable application form, can be used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for scattering or in bait stations.

The compounds or compositions according to the invention are particularly suitable for treating seed. A large part of the damage to crop plants which is caused by pests occurs as early as when the seed is attacked during storage and after the seed is introduced into the soil, during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seed of plants has been known for a long time and is subject-matter of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants. It is furthermore desirable to optimize the amount of active compound employed in such a way as to provide maximum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and also the germinating plant with a minimum of crop protection agents being employed.

The present invention therefore in particular also relates to a method for the protection of seed and germinating plants from attack by pests, by treating the seed with a composition according to the invention. The invention likewise relates to the use of the compositions according to the invention for the treatment of seed for protecting the seed and the resulting plant from pests. Furthermore, the invention relates to seed which has been treated with a composition according to the invention so as to afford protection from pests.

One of the advantages of the present invention is that the particular systemic properties of the compositions according to the invention mean that treatment of the seed with these compositions not only protects the seed itself, but also the resulting plants after emergence, from pests. In this manner, the immediate treatment of the crop at the time of sowing or shortly thereafter can be dispensed with.

Furthermore, it must be considered as advantageous that the compounds or compositions according to the invention can also be employed in particular in transgenic seed, the plants arising from this seed being capable of expressing a protein directed against pests. By treating such seed with the compositions according to the invention, certain pests can be controlled merely by the expression of the, for example, insecticidal protein, and additionally be protected by the compositions according to the invention against damage.

The compounds or compositions according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, sorghum and millet, wheat, barley, oats, rye, sunflower, tobacco, potatoes or vegetables (for example tomatoes, cabbage plants). The compositions according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with a composition according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The active compounds of the present invention, when used against hygienic pests and stored grain pests, have a good stability to alkali on calcareous substances and also show an excellent residual activity in wood and soil.

In addition, the active compounds of the formula (I) or formula (Ia) of the invention may be present as a mixed formulation with synergists and such formulations and usage forms may include commercially useful formulations and forms. Such synergists, which are not necessarily active per se, are compounds enhancing the action of the active compounds.

Generally, when used for the treatment of animals the active compounds according to the invention can be applied directly. Preferably they are applied as pharmaceutical compositions which may contain pharmaceutically acceptable excipients and/or auxiliaries which are known in the art.

In the veterinary field and in animal keeping, the active compounds are applied (=administered) in the known manner by enteral administration in the form of, for example, tablets, capsules, drinks, drenches, granules, pastes, boluses, the feed-through method, suppositories; by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like. The active compounds may be formulated as shampoo or as suitable formulations usable in aerosols, unpressurized sprays, for example pump sprays and atomizer sprays.

When used for livestock, poultry, domestic animals and the like, the active compounds according to the present invention can be applied as formulations (for example powders, wettable powders ["WP"], emulsions, emulsifiable concentrates ["EC"], flowables, homogeneous solutions and suspension concentrates ["SC"]) which comprise the active compounds in an amount of from 1 to 80% by weight, either directly or after dilution (e.g. 100- to 10 000-fold dilution), or else as a chemical bath.

When used in the veterinary field the active compounds according to the invention may be used in combination with suitable synergists or other active compounds, such as for example, acaricides, insecticides, anthelmintics, anti-protozoal drugs.

The present invention is more specifically illustrated by means of the following examples. However the present invention should not be limited only to these examples.

Synthetic Example 1

Synthesis of N-{4-[3-(3,5-dichlorophenyl)-3-(trifluoromethyl)pyrrolidin-1-yl]-2-methylbenzyl}acetamide (No. 3-11)

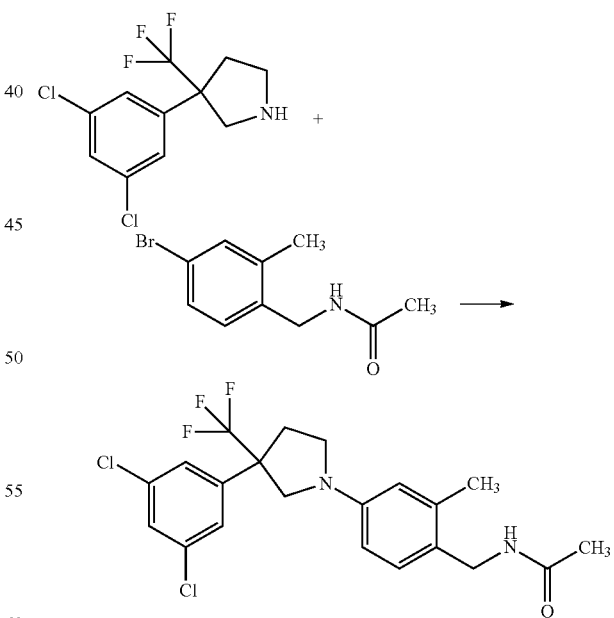

Sodium tert-butoxide (0.3 g), Tris(dibenzylidene acetone) dipalladium(0) (chloroform adduct)(0.04 g) and xantphos (0.07 g) was added to the solution of 3-(3,5-dichlorophenyl)-3-(trifluoromethyl)pyrrolidine (0.59 g) and N-(4-bromo-2-methylbenzyl)acetamide (0.5 g) in toluene under argon atmosphere, and the mixture was heated with stirring at 80° C. for 5 hours. The reaction solution was diluted with t-butylmethylether and then washed with water and brine. The organic layer was dried over anhydrous magnesium sulfate. The solvent was distilled away under the reduced pressure, and the residue was then purified by silica gel chromatography to yield N-{4-[3-(3,5-dichlorophenyl)-3-(trifluoromethyl)pyrrolidin-1-yl]-2-methylbenzyl}acetamide (0.6 g).

$^1$H-NMR (CDCl$_3$) δ: 2.13-2.18 (6H, m), 2.51-2.53 (1H, m), 2.81-2.83 (1H, m), 3.45-3.56 (2H, m), 3.75-3.78 (1H, m), 4.01-4.04 (1H, m), 4.25 (1H, s), 4.57 (1H, s), 6.40-6.44 (2H, m), 6.93-6.96 (1H, m), 7.30-7.38 (3H, m)

Synthetic Example 2

Synthesis of 4-[3-(3,5-dichlorophenyl)-3-(trifluoromethyl)pyrrolidin-1-yl]-2-nitro-N-(pyridin-2-ylmethyl)benzamide (No. 1-16)

Synthetic Example 2-1

Synthesis of 1-benzyl-3-(3,5-dichlorophenyl)-3-(trifluoromethyl)pyrrolidine (No. 5-11)

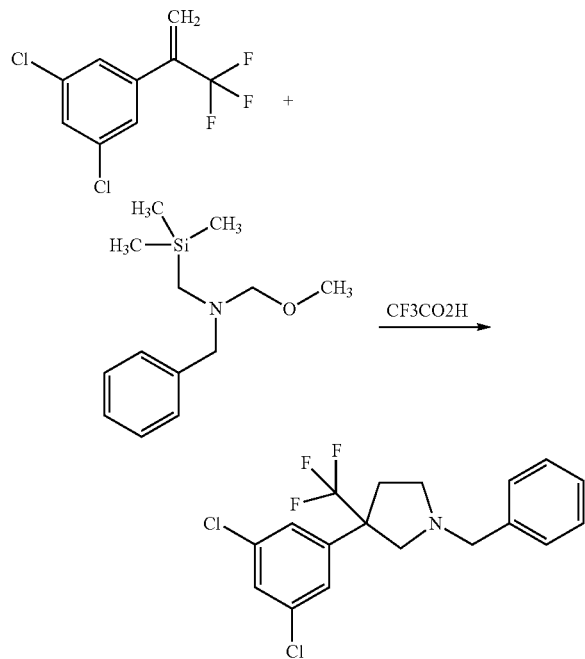

To the solution of 1,3-dichloro-5-[1-trifluoromethyl)vinyl]benzene (6.1 g) and N-benzyl-1-methoxy-N-[(trimethylsilyl)methyl]methanamine (5.0 g) in dichloromethane was added dropwise the solution of trifluoroacetic acid (0.24 g) in dichloromethane while cooling with ice. On completion of the dropwise addition, the mixture was warmed to room temperature and stirred for 3 hours. The solution was concentrated under the reduced pressure, and the residue was then diluted with t-butylmethylether. The solution was washed with saturated sodium bicarbonate water and dried over anhydrous magnesium sulfate. After the drying agent was filtered off, the solvent was distilled away under the reduced pressure, and the residue was then purified by silica gel chromatography to yield 1-benzyl-3-(3,5-dichlorophenyl)-3-(trifluoromethyl)pyrrolidine (5.7 g). $^1$H-NMR (CDCl$_3$) δ: 2.27-2.36 (1H, m), 2.53-2.62 (1H, m), 2.69-2.83 (2H, m), 3.08 (2H, dd), 3.67 (2H, s), 7.25-7.36 (8H, m)

Synthetic Example 2-2

Synthesis of 3-(3,5-dichlorophenyl)-3-(trifluoromethyl)pyrrolidine (No. 5-12)

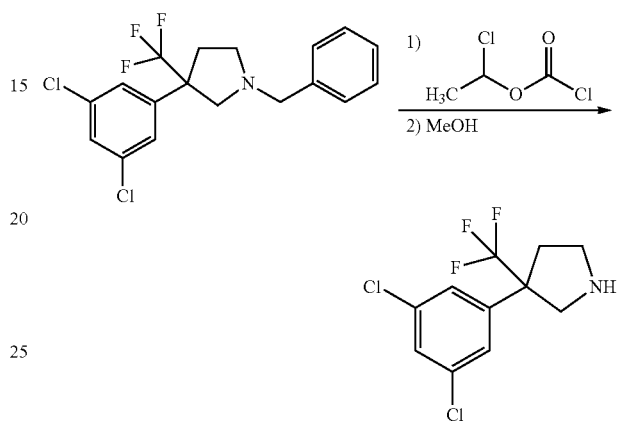

The solution of 1-benzyl-3-(3,5-dichlorophenyl)-3-(trifluoromethyl)pyrrolidine (5.7 g) and 1-chloroethyl chloroformate (4.4 g) in dichloroethane was heated to reflux for 3 hours. The mixture was cooled to room temperature and then concentrated under the reduced pressure. Methanol was added to the resultant residue, which was then heated with stirring at 60° C. for two hours. The mixture was cooled to room temperature, to which was then added water. The solution was washed twice with the mixed solvent of hexane and ethyl acetate (9:1). The solution was alkalized with sodium hydrogen carbonate and then extracted with ethyl acetate three times. The organic layer was combined, which was then washed with brine and dried over anhydrous magnesium sulfate. After the drying agent was filtered off, the solvent was distilled away under the reduced pressure to yield 3-(3,5-dichlorophenyl)-3-(trifluoromethyl)pyrrolidine (4.2 g). $^1$H-NMR (CDCl$_3$) δ: 2.24-2.33 (1H, m), 2.51-2.56 (1H, m), 2.97-3.07 (1H, m), 3.19-3.26 (2H, m), 3.74 (1H, d), 7.25 (2H, d), 7.35 (1H, t)

Synthetic Example 2-3

Synthesis of methyl 4-[3-(3,5-dichlorophenyl)-3-(trifluoromethyl)pyrrolidin-1-yl]-2-nitrobenzoate (No. 4-6)

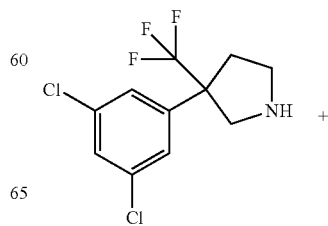

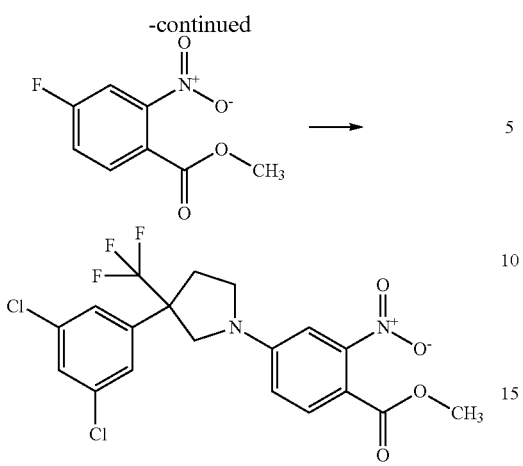

To the solution of methyl 4-fluoro-2-nitrobenzoate (1.1 g) and 3-(3,5-dichlorophenyl)-3-(trifluoromethyl)pyrrolidine (1.5 g) in 1-methyl-2-pyrrolidinone was added potassium carbonate (1.5 g) and the mixture was heated with stirring at 100° C. for two hours. The mixture was cooled to room temperature and then poured into water, which was then extracted twice with ethyl acetate. The organic layer was combined, which was then washed with water and dried over anhydrous magnesium sulfate. After the drying agent was filtered off, the solvent was distilled away under the reduced pressure, and the residue was then purified by silica gel chromatography to yield methyl 4-[3-(3,5-dichlorophenyl)-3-(trifluoromethyl)pyrrolidin-1-yl]-2-nitrobenzoate (1.24 g). $^1$H-NMR (CDCl$_3$) δ: 2.53-2.67 (1H, m), 2.89-2.97 (1H, m), 3.50-3.71 (2H, m), 3.83 (1H, d), 3.85 (3H, s), 4.15 (1H, d), 6.69 (1H, dd), 6.75 (1H, d), 7.26 (2H, d), 7.42 (1H, t), 7.81 (1H, d)

Synthetic Example 2-4

Synthesis of 4-[3-(3,5-dichlorophenyl)-3-(trifluoromethyl)pyrrolidin-1-yl]-2-nitrobenzoic acid (No. 4-7)

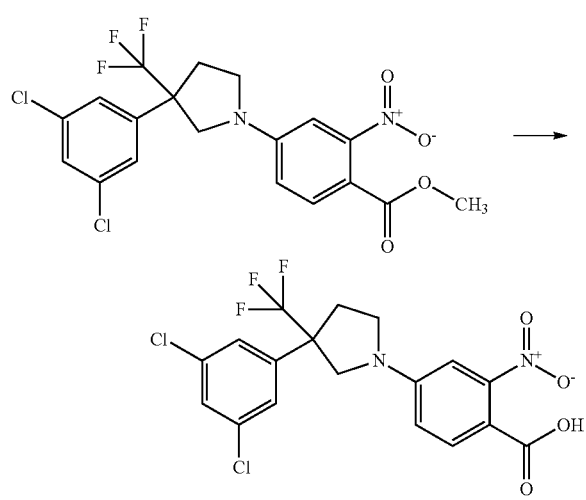

To the solution of methyl 4-[3-(3,5-dichlorophenyl)-3-(trifluoromethyl)pyrrolidin-1-yl]-2-nitrobenzoate (1.24 g) in 1,4-dioxane was added 2N aqueous sodium hydroxide (5.4 mL), and the mixture was heated with stirring at 80° C. The mixture was cooled to room temperature and then acidified with 2N hydrochloric acid before the mixture was extracted twice with ethyl acetate. The organic layer was combined, which was then washed with water and dried over anhydrous magnesium sulfate. After the drying agent was filtered off, the solvent was distilled away under the reduced pressure to yield 4-[3-(3,5-dichlorophenyl)-3-(trifluoromethyl)pyrrolidin-1-yl]-2-nitrobenzoic acid (0.85 g). $^1$H-NMR (DMSO-d6) δ: 2.58-2.72 (1H, m), 2.91-3.04 (1H, m), 3.47-3.57 (2H, m), 3.87 (1H, d), 4.32 (1H, d), 6.86 (1H, dd), 7.04 (1H, d), 7.65 (2H, d), 7.71 (1H, t), 7.78 (1H, d)

Synthetic Example 2-5

Synthesis of 4-[3-(3,5-dichlorophenyl)-3-(trifluoromethyl)pyrrolidin-1-yl]-2-nitro-N-(pyridin-2-ylmethyl)benzamide (No. 1-16)

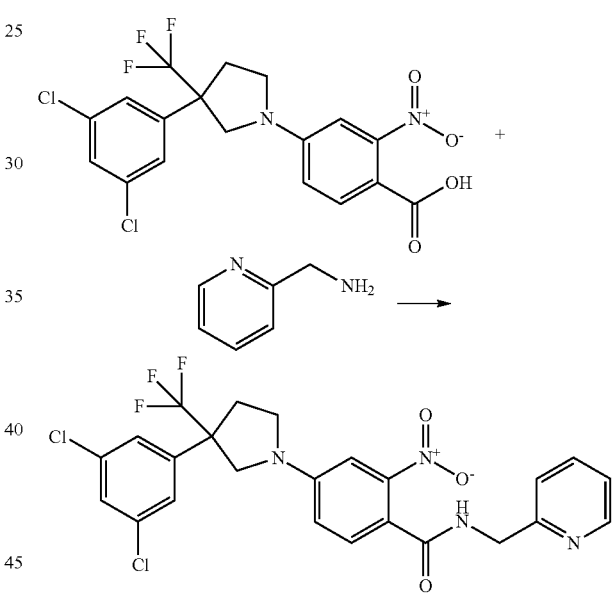

To the solution of 4-[3-(3,5-dichlorophenyl)-3-(trifluoromethyl)pyrrolidin-1-yl]-2-nitrobenzoic acid (0.3 g) and 2-picolylamine (0.07 g) in DMF was added 1-ethyl-3-(3'-dimethylaminopropyl)carbodiimide hydrochloride (0.13 g) and 1-hydroxybenzotriazole monohydrate (0.01 g), and the mixture was stirred for 6 hour at room temperature. The reaction solution was poured into water, which was then extracted twice with ethyl acetate. The organic layer was combined, which was then washed with water and dried over anhydrous magnesium sulfate. After the drying agent, was filtered off, the solvent was distilled away under the reduced pressure, and the residue was then purified by silica gel chromatography to yield 4-[3(3,5-dichlorophenyl)-3-(trifluoromethyl)pyrrolidin-1-yl]-2-nitro-N-(pyridine-2-ylmethyl)benzamide (0.19 g). $^1$H-NMR (CDCl$_3$) δ: 2.54-2.65 (1H, m), 2.89-2.97 (1H, m), 3.51-3.67 (2H, m), 3.83 (1H, d), 4.13 (1H, d), 4.74 (2H, d), 6.75 (1H, dd), 7.08 (1H, d), 7.15-7.23 (2H, m), 7.28 (2H, br s), 7.37 (1H, d), 7.41 (1H, t), 7.49 (1H, d), 7.70 (1H, td), 8.52 (1H, d).

Synthetic Example 3

2-chloro-4-[3-(3,5-dichlorophenyl)-3-(trifluoromethyl)pyrrolidin-1-yl]-N-(pyridin-2-ylmethyl)benzenecarbothioamide (No. 1-81)

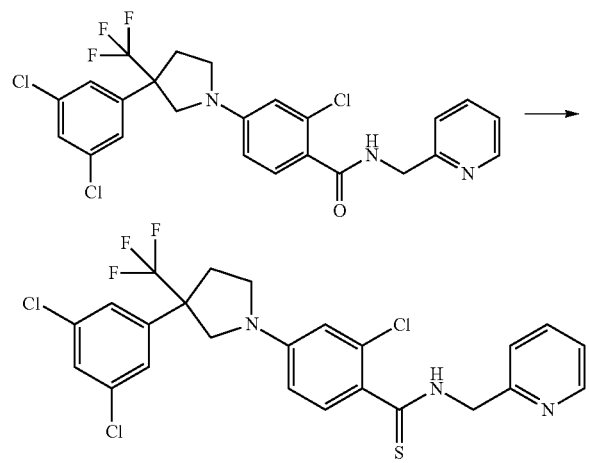

To the solution of 2-chloro-4-[3-(3,5-dichlorophenyl)-3-(trifluoromethyl)pyrrolidin1-yl]-N-(pyridin-2-ylmethyl)benzamide (0.35 g) in toluene was added Lawesson reagent (0.28 g) and the mixture was heated to reflux for 3 hours. After the mixture was cooled to room temperature, the solvent was distilled away under the reduced pressure, and the residue was purified by silica gel chromatography to yield 2-chloro-4-[3-(3,5-dichlorophenyl)-3-(trifluoromethyl)pyrrolidin1-yl]-N-(pyridin-2-ylmethyl)benzenecarbothioamide (0.10 g). $^1$H-NMR (CDCl$_3$) δ: 2.51-2.61 (1H, m), 2.84-2.92 (1H, m), 3.45-3.61 (2H, m), 3.79 (1H, d), 4.08 (1H, d), 5.08 (2H, d), 6.49-6.54 (2H, m), 7.22-7.28 (3H, m), 7.36 (1H, d), 7.40 (1H, t), 7.72 (1H, td), 7.79 (1H, d), 8.54 (1H, d), 9.27 (1H, br s).

Synthetic Example 4

Synthesis of N-{2-chloro-4-[3-(3,5-dichlorophenyl)-3-(trifluoromethyl)pyrrolidin-1-yl]benzyl}acetamide (No. 3-3)

Synthetic Example 4-1

Synthesis of 1-{2-chloro-4-[3-(3,5-dichlorophenyl)-3-(trifluoromethyl)pyrrolidin-1-yl]phenyl}methanamine (No. 4-49)

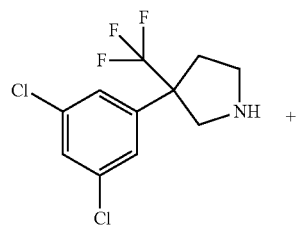 +

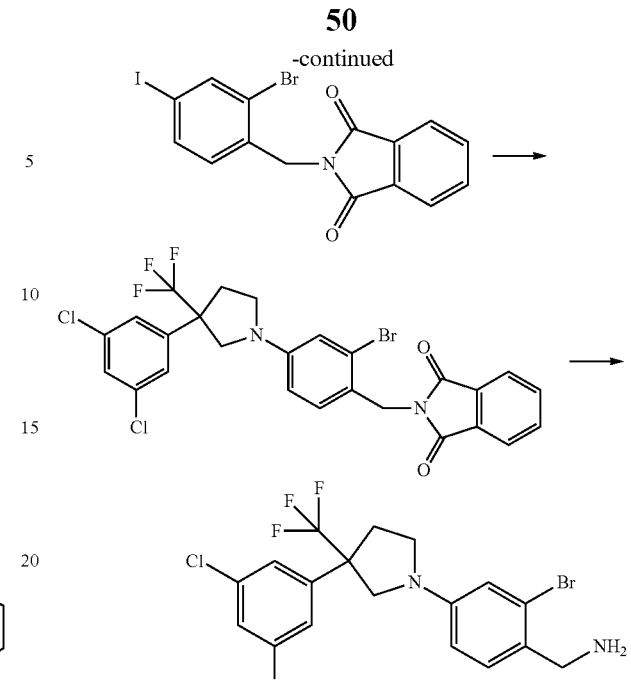

Sodium tert-butoxide (0.2 g), Tris(dibenzylidene acetone) dipalladium(0) (chloroform adduct)(0.03 g) and xantphos (0.05 g) was added to the solution of 3-(3,5-dichlorophenyl)-3-(trifluoromethyl)pyrrolidine (0.4 g) and 2-(2-chloro-4-iodobenzyl)-1H-isoindole-1,3-(2H)-dione (0.69 g) in toluene under argon atmosphere, and the mixture was heated with stirring at 80° C. for 3 hours. The reaction solution was diluted with t-butylmethylether and then washed with water and brine. The organic layer was dried over anhydrous magnesium sulfate. The solvent was distilled away under the reduced pressure to yield the crude product. The product was dissolved in methanol, to which was then added aqueous hydrazine (0.03 g), followed by the mixture heated to reflux for 12 hours. The reaction solution was diluted with t-butylmethylether and then washed with saturated saline. The organic layer was dried over anhydrous magnesium sulfate. The solvent was distilled away under the reduced pressure, and the residue was then purified by silica gel chromatography to yield 1-{2-chloro-4-[3-(3,5-dichlorophenyl)-3-(trifluoromethyl)pyrrolidin-1-yl]phenyl}methanamine (0.12 g). $^1$H-NMR (CDCl$_3$) δ: 2.47-2.54 (1H, m), 2.78-2.85 (1H, m), 3.46-3.49 (2H, m), 3.69-4.01 (4H, m), 6.47-6.50 (1H, m), 6.73-6.76 (1H, m), 7.25-7.35 (4H, m).

Synthetic Example 4-2

Synthesis of N-{2-chloro-4-[3-(3,5-dichlorophenyl)-3-(trifluoromethyl)pyrrolidin-1-yl]benzyl}acetamide (No. 3-3)

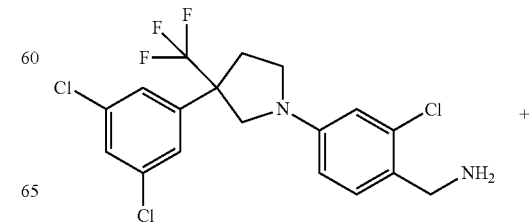 +

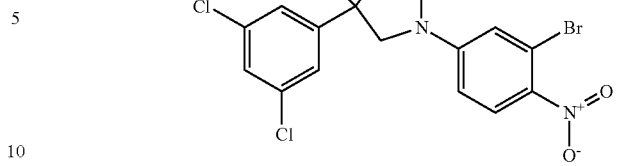

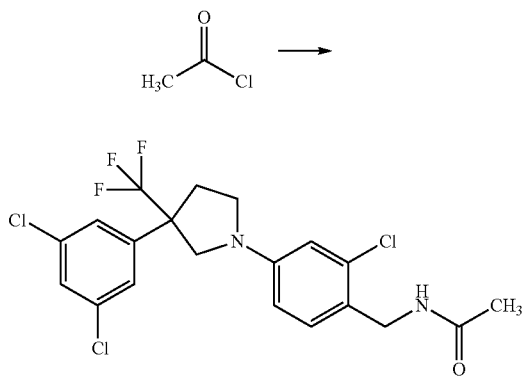

To the solution of 1-{2-chloro-4-[3-(3,5-dichlorophenyl)-3-(trifluoromethyl)pyrrolidin-1-yl]phenyl}methanamine (0.12 g) and triethylamine (0.04 g) in tetrahydrofuran was added dropwise acetyl chloride (0.02 g), and the mixture was stirred for one hour at room temperature. The reaction solution was diluted with t-butylmethylether and then washed with water and brine. The organic layer was dried over anhydrous magnesium sulfate. The solvent was distilled away under the reduced pressure, and the residue was then purified by silica gel chromatography to yield N-{2-chloro-4-[3-(3,5-dichlorophenyl)-3-(trifluoromethyl)pyrrolidin-1-yl]benzyl}acetamide (0.1 g). $^1$H-NMR (CDCl$_3$) δ: 1.98-2.01 (3H, m), 2.50-2.58 (1H, m), 2.82-2.87 (1H, m), 3.45-3.51 (2H, m), 3.74 (1H, d), 4.02 (1H, d), 4.41 (2H), 6.43-6.46 (1H, m), 6.58-6.59 (1H, m), 7.26-7.38 (4H, m)

Synthetic Example 5

Synthesis of 1-{2-bromo-4-[3-(3,5-dichlorophenyl)-3-(trifluoromethyl)pyrrolidin-1-yl]phenyl}-1H-tetrazole (No. 2-23)

Synthetic Example 5-1

Synthesis of 1-(bromo-4-nitrophenyl)-3-(3,5-dichlorophenyl)-3-(trifluoromethyl)pyrrolidine (No. 4-20)

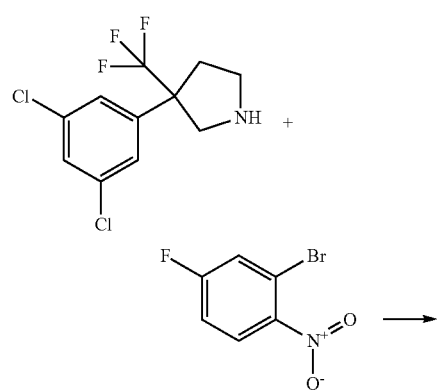

To the solution of 3-(3,5-dichlorophenyl)-3-(trifluoromethyl)pyrrolidine (1.3 g) and 2-bromo-4-fluoro-1-nitrobenzene (1.0 g) in 1-methyl-2-pyrrolidinone was added potassium carbonate (1.3 g), and the mixture was heated with stirring at 100° C. for 3 hours. The mixture was cooled to room temperature and then poured into water, which was extracted twice with ethyl acetate. The organic layer was combined, which was then washed with water and dried over anhydrous magnesium sulfate. After the drying agent was filtered off, the solvent was distilled away under the reduced pressure, and the residue was then purified by silica gel chromatography to yield 1-(3-bromo-4-nitrophenyl)-3-(3,5-dichlorophenyl)-3-(trifluoromethyl)pyrrolidine (1.56 g). $^1$H-NMR (CDCl$_3$) δ: 2.53-2.66 (1H, m), 2.89-2.97 (1H, m), 3.51-3.71 (2H, m), 3.83 (1H, d), 4.16 (1H, d), 6.53 (1H, dd), 6.84 (1H, d), 7.27 (2H, br s), 7.42 (1H, t), 8.07 (1H, d).

Synthetic Example 5-2

Synthesis of 2-bromo-4-[3-(3,5-dichlorophenyl)-3-(trifluoromethyl)-pyrrolidin-1-yl]aniline (No. 4-21)

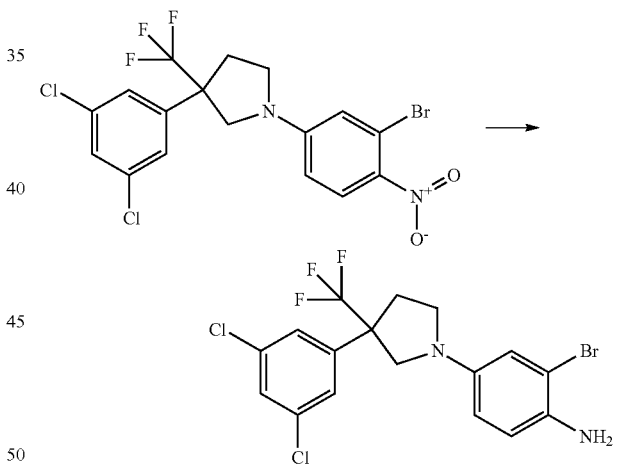

To the solution of 1-(3-bromo-4-nitrophenyl)-3-(3,5-dichlorophenyl)-3-(trifluoromethyl)pyrrolidine (1.10 g) in the mixed solvent of 1,4-dioxane and ethanol was added stannous chloride dihydrate (2.05 g) and a small amount of concentrated hydrochloric acid, and the mixture was then stirred 4 hours at 90° C. The mixture was cooled to room temperature and then poured into the mixed solution of ethyl acetate and water, which was then neutralized with sodium hydrogen carbonate with vigorous stirring. After filtration of precipitate through Celite, the organic layer was separated and the aqueous layer was extracted with ethyl acetate. The organic layer was combined, which was then washed with brine and dried over anhydrous magnesium sulfate. After the drying agent was filtered off, the solvent was distilled away under the reduced pressure, and the residue was then purified by silica gel chromatography to yield 2-bromo-4-[3-(3,5-dichlorophenyl)-3-(trifluoromethyl)-pyrrolidin-1-yl]aniline (0.73 g). $^1$H-NMR (CDCl$_3$) δ: 2.44-2.54 (1H, m), 2.75-2.83 (1H, m), 3.32-3.50 (2H, m), 3.56-3.76 (3H, m), 3.92 (1H, d), 6.46 (1H, dd), 6.70-6.78 (2H, m), 7.29 (2H, br s), 7.37 (1H, t).

Synthetic Example 5-3

Synthesis of 1-{2-bromo-4-[3-(3,5-dichlorophenyl)-3-(trifluoromethyl)pyrrolidin-1-yl]phenyl}-1H-tetrazole (No. 2-23)

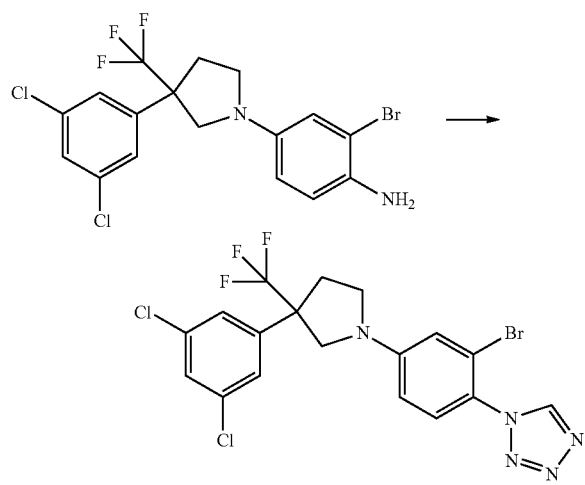

To the mixture of 2-bromo-4-[3-(3,5-dichlorophenyl)-3-(trifluoromethyl)-pyrrolidin-1-yl]aniline (0.60 g), triethyl orthoformate (0.98 g) and sodium azide (0.38 g) was added acetic acid (1.1 g), and the mixture was then heated with stifling at 100° C. for 4 hours. The mixture was cooled to room temperature and then poured into water, which was then extracted twice with ethyl acetate. The organic layer was combined, which was then washed with water and dried over anhydrous magnesium sulfate. After the drying agent was filtered off, the solvent was distilled away under the reduced pressure, and the residue was then purified by silica gel chromatography to yield 1-{2-bromo-4-[3-(3,5-dichlorophenyl)-3-(trifluoromethyl)-pyrrolidin-1-yl]phenyl}-1H-tetrazole (0.52 g). m.p. 193-194° C.

Synthetic Example 6

Synthesis of 5-[3-(3,5-dichlorophenyl)-3-(trifluoromethyl)pyrrolidin-1-yl]-2-(1H-1,2,4-triazol-1-yl)benzonitrile (No. 2-39)

Synthetic Example 6-1

Synthesis of 5-[3-(3,5-dichlorophenyl)-3-(trifluoromethyl)pyrrolidin-1-yl]-2-fluorobenzonitrile (No. 4-17)

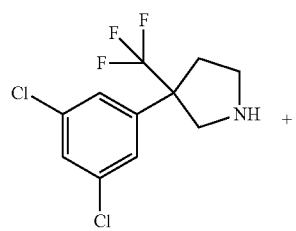

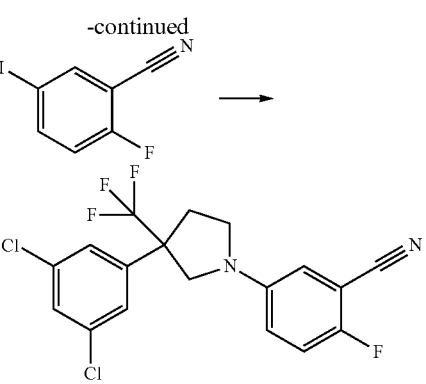

3-(3,5-dichlorophenyl)-3-(trifluoromethyl)pyrrolidine (0.6 g) and 2-fluoro-5-iodobenzonitrile (0.57 g) was dissolved in toluene, which was then degassed 3 times. To the solution in toluene was added sodium tert-butoxide (0.20 g), Tris(dibenzylidene acetone)dipalladium chloroform complex (0.04 g) and Xantphos (0.07 g) under argon atmosphere, and the mixture was stirred at 80° C. for two hours. The mixture was cooled to room temperature and then diluted with ethyl acetate, which was then washed with water and dried over anhydrous magnesium sulfate. After the drying agent was filtered off, the solvent was distilled away under the reduced pressure, and the residue was then purified by silica gel chromatography to yield 5-[3-(3,5-dichlorophenyl)-3-(trifluoromethyl)pyrrolidin-1-yl]-2-fluorobenzonitrile (0.54 g). m.p. 184-186° C.

Synthetic Example 6-2

Synthesis of 5-[3-(3,5-dichlorophenyl)-3-(trifluoromethyl)pyrrolidin-1-yl]-2-(1H-1,2,4-triazol-1-yl)benzonitrile (No. 2-39)

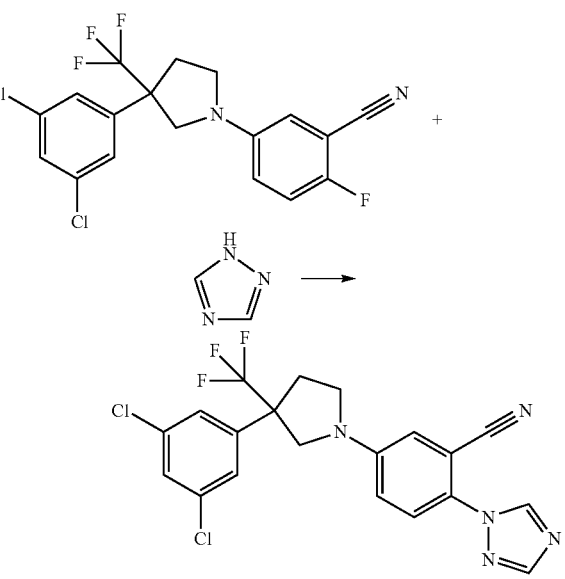

To the solution of 1H-1,2,4-triazole (0.06 g) in DMF was added sodium hydride (0.04 g) while cooling with ice, and the mixture was warmed to room temperature and then stirred for 0.5 hr. To this solution was added the solution of 5-[3-(3,5-dichlorophenyl)-3-(trifluoromethyl)pyrrolidin-1-yl]2-fluorobenzonitrile (0.30 g) in DMF, and the mixture was heated to reflux for 6 hours. The mixture was cooled to room temperature and then poured into water, which was then extracted twice with ethyl acetate. The organic layer was combined, which was then washed with water and dried over anhydrous magnesium sulfate. After the drying agent was filtered off, the solvent was distilled away under the reduced pressure, and the residue was then purified by silica gel chromatography to yield 5-[3-(3,5-dichlorophenyl)-3-(trifluoromethyl)pyrrolidin-1-yl]-2-(1H-1,2,4-triazol-1-yl)benzonitrile (0.18 g). $^1$H-NMR (DMSO-d6) δ: 2.62-2.73 (1H, m), 2.95-3.03 (1H, m), 3.49-3.55 (2H, m), 3.90 (1H, d), 4.31 (1H, d), 7.09 (1H, dd), 7.29 (1H, d), 7.61 (1H, d), 7.68 (2H, d), 7.71 (1H, t), 8.26 (1H, s), 8.98 (1H, s)

Synthetic Example 7

Synthesis of 1,3-dimethyl-2-nitro-5-[1-(trifluoromethyl)vinyl]benzene (No. 6-1)

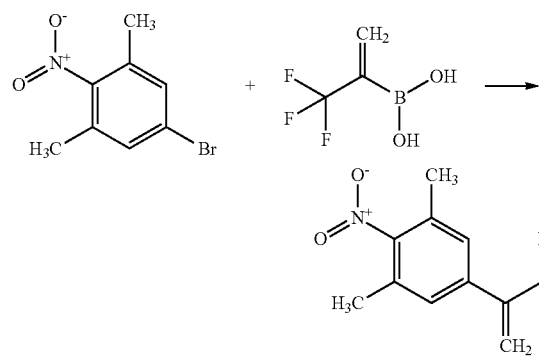

5-bromo-1,3-dimethyl-2-nitrobenzene (10.0 g), [1-(trifluoromethyl)vinyl]boronic acid (purity: 60%, 13.4 g) and potassium carbonate (14.4 g) was dissolved in the mixed solvent of THF and water, which was then degassed three times. To the solution was added dichloro bis(triphenylphosphine)palladium (II) (1.5 g), and the mixture was heated to reflux for 3 hours under argon atmosphere. The mixture was cooled to room temperature and then poured into water, which was then extracted twice with ethyl acetate. The organic layer was combined, which was then washed with water and dried over anhydrous magnesium sulfate. After the drying agent was filtered off, the solvent was distilled away under the reduced pressure, and the residue was then purified by silica gel chromatography to yield 1,3-dimethyl-2-nitro-5-[1-(trifluoromethyl)vinyl]benzene (11.2 g). $^1$H-NMR (CDCl$_3$) δ: 2.34 (6H, s), 5.78-5.80 (1H, m), 6.03-6.04 (1H, m), 7.20 (2H, s).

Synthetic Example 8

Synthesis of 4-[3-(3,5-dichlorophenyl)-3-(trifluoromethyl)pyrrolidin-1-yl]benzonitrile (No. 4-2)

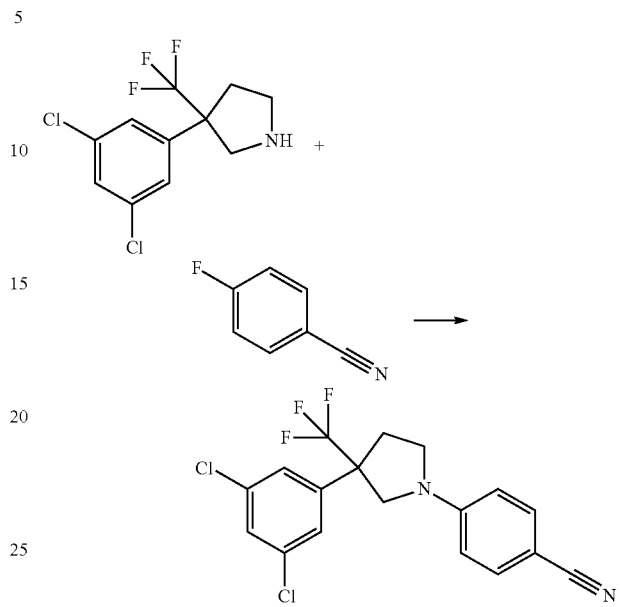

To the solution of 3-(3,5-dichlorophenyl)-3-(trifluoromethyl)pyrrolidine (0.30 g) and 4-fluorobenzonitrile (0.12 g) in DMSO (dimethylsurufoxide) was added potassium carbonate (0.27 g), and the mixture was heated with stirring at 120° C. for 6 hours. The mixture was cooled to room temperature and then poured onto water, which was then extracted twice with ethyl acetate. The organic layer was combined, which was then washed with water and dried over anhydrous magnesium sulfate. After the drying agent was filtered off, the solvent was distilled away under the reduced pressure, and the residue was then purified by silica gel chromatography to yield 4-[3-(3,5-dichlorophenyl)-3-(trifluoromethyl)pyrrolidin-1-yl]benzonitrile (0.05 g). $^1$H-NMR (CDCl$_3$) δ: 2.51-2.62 (1H, m), 2.86-2.94 (1H, m), 3.56-3.61 (2H, m), 3.80 (1H, d), 4.12 (1H, d), 6.59 (2H, d), 7.26 (2H, br s), 7.41 (1H, t), 7.52 (2H, d).

The compounds and intermediates of the formula (I) or formula (Ia) of the invention obtained by the same methods as those of the above synthetic examples and according to the methods described above in detail, as well as their physical values are showed in tables 1-13. Each compound obtained in the above synthetic examples is also showed in each correspondent table.

In these tables, the following abbreviations are used.

Me: methyl, Et: ethyl, Pr: propyl, Bu: butyl, Ph: phenyl, Pen: pentyl.

TABLE 1

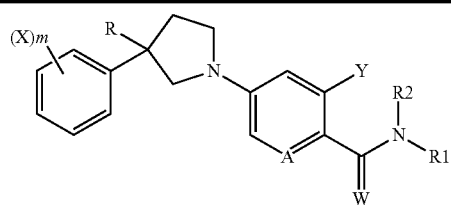

| | (X)m | R | Y | R1 | R2 | A | W | m.p. ° C.) |
|---|---|---|---|---|---|---|---|---|
| 1-1 | 3,5-diCl | CF3 | H | CF3CH2 | H | CH | O | |
| 1-2 | 3,5-diCl | CF3 | H | 2-PyridylCH2 | H | CH | O | |
| 1-3 | 3,5-diCl | CF3 | CH3 | CF3CH2 | H | CH | O | |

TABLE 1-continued

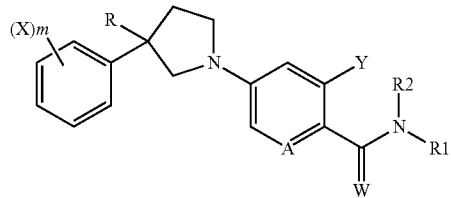

| | (X)m | R | Y | R1 | R2 | A | W | m.p. ° C.) |
|---|---|---|---|---|---|---|---|---|
| 1-4 | 3,5-diCl | CF3 | CH3 | 2-PyridylCH2 | H | CH | O | |
| 1-5 | 3,5-diCl | CF3 | F | CF3CH2 | H | CH | O | |
| 1-6 | 3,5-diCl | CF3 | F | 2-PyridylCH2 | H | CH | O | |
| 1-7 | 3,5-diCl | CF3 | Cl | CF3CH2 | H | CH | O | |
| 1-8 | 3,5-diCl | CF3 | Cl | 2-PyridylCH2 | H | CH | O | |
| 1-9 | 3,5-diCl | CF3 | Br | CF3CH2 | H | CH | O | |
| 1-10 | 3,5-diCl | CF3 | Br | 2-PyridylCH2 | H | CH | O | |
| 1-11 | 3,5-diCl | CF3 | Br | cyclo-Pr | H | CH | O | |
| 1-12 | 3,5-diCl | CF3 | Br | NCCH2CH2 | H | CH | O | |
| 1-13 | 3,5-diCl | CF3 | I | CF3CH2 | H | CH | O | |
| 1-14 | 3,5-diCl | CF3 | I | 2-PyridylCH2 | H | CH | O | |
| 1-15 | 3,5-diCl | CF3 | NO2 | CF3CH2 | H | CH | O | |
| 1-16 | 3,5-diCl | CF3 | NO2 | 2-PyridylCH2 | H | CH | O | |
| 1-17 | 3-Cl | CF3 | NO2 | 2-PyridylCH2 | H | CH | O | |
| 1-18 | 3-Cl | CF3 | NO2 | CF3CH2 | H | CH | O | |
| 1-19 | 3-Br | CF3 | NO2 | 2-PyridylCH2 | H | CH | O | |
| 1-20 | 3-CF3 | CF3 | NO2 | 2-PyridylCH2 | H | CH | O | 169-170 |
| 1-21 | 3-CF3 | CF3 | NO2 | CF3CH2 | H | CH | O | |
| 1-22 | 3,5-diCF3 | CF3 | NO2 | 2-PyridylCH2 | H | CH | O | |
| 1-23 | 3,5-diCF3 | CF3 | NO2 | CF3CH2 | H | CH | O | |
| 1-24 | 3-NO2 | CF3 | NO2 | 2-PyridylCH2 | H | CH | O | 176-179 |
| 1-25 | 3,5-diCl | CF3 | CF3 | 2-PyridylCH2 | H | CH | O | |
| 1-26 | 3,5-diCl | CF3 | CH3O | 2-PyridylCH2 | H | CH | O | |
| 1-27 | 3,5-diCl | CF3 | CN | 2-PyridylCH2 | H | CH | O | |
| 1-28 | 3,5-diCl | CF3 | CF3O | 2-PyridylCH2 | H | CH | O | |
| 1-29 | 3,5-diCl | CF3 | CH3S | 2-PyridylCH2 | H | CH | O | |
| 1-30 | 3,5-diCl | CF3 | CH3S(O) | 2-PyridylCH2 | H | CH | O | |
| 1-31 | 3,5-diCl | CF3 | CH3S(O)2 | 2-PyridylCH2 | H | CH | O | |
| 1-32 | 3,5-diCl | CF3 | CF3S | 2-PyridylCH2 | H | CH | O | |
| 1-33 | 3,5-diCl | CF3 | CF3S(O) | 2-PyridylCH2 | H | CH | O | |
| 1-34 | 3,5-diCl | CF3 | CF3S(O)2 | 2-PyridylCH2 | H | CH | O | |
| 1-35 | 3,5-diCl | CF3 | OH | 2-PyridylCH2 | H | CH | O | |
| 1-36 | 3,5-diCl | CF3 | SH | 2-PyridylCH2 | H | CH | O | |
| 1-37 | 3,5-diCl | CF3 | NH2 | 2-PyridylCH2 | H | CH | O | |
| 1-38 | 3,5-diCl | CF3 | NHCOCH3 | 2-PyridylCH2 | H | CH | O | |
| 1-39 | 3,5-diCl | CF3 | NHCOCF3 | 2-PyridylCH2 | H | CH | O | |
| 1-40 | 3,5-diCl | CF3 | NHCO2CH3 | 2-PyridylCH2 | H | CH | O | |
| 1-41 | 3,5-diCl | CF3 | NHCO2CH2CCl3 | 2-PyridylCH2 | H | CH | O | |
| 1-42 | 3-CH3 | CF3 | H | 2-PyridylCH2 | H | CH | O | |
| 1-43 | 3-CH3O | CF3 | H | 2-PyridylCH2 | H | CH | O | |
| 1-44 | 3-CN | CF3 | H | 2-PyridylCH2 | H | CH | O | |
| 1-45 | 3-CF3O | CF3 | H | 2-PyridylCH2 | H | CH | O | |
| 1-46 | 3-CH3S | CF3 | H | 2-PyridylCH2 | H | CH | O | |
| 1-47 | 3-CH3S(O) | CF3 | H | 2-PyridylCH2 | H | CH | O | |
| 1-48 | 3-CH3S(O)2 | CF3 | H | 2-PyridylCH2 | H | CH | O | |
| 1-49 | 3-CF3S | CF3 | H | 2-PyridylCH2 | H | CH | O | |
| 1-50 | 3-CF3S(O) | CF3 | H | 2-PyridylCH2 | H | CH | O | |
| 1-51 | 3-CF3S(O)2 | CF3 | H | 2-PyridylCH2 | H | CH | O | |
| 1-52 | 3-OH | CF3 | H | 2-PyridylCH2 | H | CH | O | |
| 1-53 | 3-SH | CF3 | H | 2-PyridylCH2 | H | CH | O | |
| 1-54 | 3,5-diCl | CF3 | H | 2-PyridylCH2 | H | CH | O | |
| 1-55 | 3,4-diCl | CF3 | H | CF3CH2 | H | CH | O | 77-80 |
| 1-56 | 3,4,5-triCl | CF3 | H | 2-PyridylCH2 | H | CH | O | |
| 1-57 | 3,4,5-triCl | CF3 | H | CF3CH2 | H | CH | O | |
| 1-58 | 3,5-diBr | CF3 | H | 2-PyridylCH2 | H | CH | O | |
| 1-59 | 3,5-diBr | CF3 | H | CF3CH2 | H | CH | O | |
| 1-60 | 3,5-diMe-4-NO2 | CF3 | H | 2-PyridylCH2 | H | CH | O | |
| 1-61 | 3,5-diMe-4-NO2 | CF3 | H | CF3CH2 | H | CH | O | |
| 1-62 | 3,5-diCl | CF3 | H | 2-PyridylCH2 | H | CH | S | |
| 1-63 | 3,5-diCl | CF3 | NO2 | H | H | CH | O | |
| 1-64 | 3,5-diCl | CF3 | NO2 | Me | H | CH | O | |
| 1-65 | 3,5-diCl | CF3 | NO2 | iso-Pr | H | CH | O | |
| 1-66 | 3,5-diCl | CF3 | NO2 | PhCH2 | H | CH | O | |
| 1-67 | 3,5-diCl | CF3 | NO2 | CH2CO2CH3 | H | CH | O | |
| 1-68 | 3,5-diCl | CF3 | NO2 | CH2CONMe | H | CH | O | |
| 1-69 | 3,5-diCl | CF3 | NO2 | CH2(cyclo)Pr | H | CH | O | |
| 1-70 | 3,5-diCl | CF3 | NO2 | SO2Me | H | CH | O | |

TABLE 1-continued

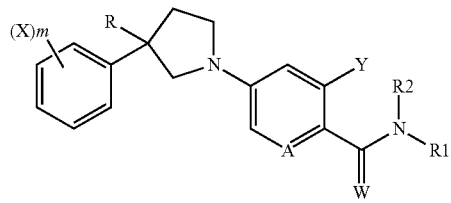

| | (X)m | R | Y | R1 | R2 | A | W | m.p. ° C.) |
|---|---|---|---|---|---|---|---|---|
| 1-71 | 3,5-diCl | CF3 | NO2 | SO2CF3 | H | CH | O | |
| 1-72 | 3,5-diCl | CF3 | NO2 | CH2=CHCH2 | H | CH | O | |
| 1-73 | 3,5-diCl | CF3 | NO2 | HCCCH2 | H | CH | O | |
| 1-74 | 3,5-diCl | CF3 | NO2 | CH2CN | H | CH | O | |
| 1-75 | 3,5-diCl | CF3 | NO2 | C(Me)2CH2SCH3 | H | CH | O | |
| 1-76 | 3,5-diCl | CF3 | NO2 | 2-F—Ph | H | CH | O | |
| 1-77 | 3,5-diCl | CH3 | H | 2-PyridylCH2 | H | CH | O | |
| 1-78 | 3,5-diCl | CF3 | H | 2-PyridylCH2 | H | N | O | |
| 1-79 | 3,5-diCl | CF3 | H | 2-PyridylCH2 | CH3 | CH | O | |
| 1-80 | 3-NO2 | CF3 | NO2 | CF3CH2 | H | CH | O | |
| 1-81 | 3,5-diCl | CF3 | Cl | 2-PyridylCH2 | H | CH | S | |
| 1-82 | 2-diCl | CF3 | NO2 | 2-PyridylCH2 | H | CH | O | |
| 1-83 | 2,3-diCl | CF3 | NO2 | 2-PyridylCH2 | H | CH | O | |
| 1-84 | 3,5-diCl | CF3 | NO2 | 3-PyridylCH2 | H | CH | O | |
| 1-85 | 3,5-diCl | CF3 | NO2 | 4-PyridylCH2 | H | CH | O | |
| 1-86 | 3,5-diCl | CF3 | NO2 | 2-(6-Cl-pyridyl)CH2 | H | CH | O | |
| 1-87 | 3,5-diCl | CF3 | NO2 | 3-(6-Cl-pyridyl)CH2 | H | CH | O | |
| 1-88 | 3,5-diCl | CF3 | NO2 | 2-PyrinidinylCH2 | H | CH | O | |
| 1-89 | 3,5-diCl | CF3 | NO2 | 1-(1-ethylpyrrolidin-2-yl)CH2 | H | CH | O | |
| 1-90 | 3,5-diCl | CF3 | CF3 | CF3CH2 | H | CH | O | |
| 1-91 | 3,5-diCl | CF3 | CF3 | 2-(6-Cl-pyridyl)CH2 | H | CH | O | |
| 1-92 | 3,5-diCl | CF3 | NO2 | Me2NCH= | | CH | O | |
| 1-93 | 3,5-diCl | CF3 | NO2 | EtON=CH | H | CH | O | |
| 1-94 | 3,5-diCl | CF3 | C=NOCH3 | 2-PyridylCH2 | H | CH | O | |
| 1-95 | 4-Cl | CF3 | NO2 | 2-PyridylCH2 | H | CH | O | |
| 1-96 | 4-Cl | CF3 | NO2 | CF3CH2 | H | CH | O | |
| 1-97 | 3,5-diCl | CF3 | CN | CF3CH2 | H | CH | O | |
| 1-98 | 3,5-diCl | CF3 | CF3 | H | H | CH | O | |
| 1-99 | 3,5-diCF3 | CF3 | CF3 | 2-PyridylCH2 | H | CH | O | |
| 1-100 | 3,5-diCF3 | CF3 | CF3 | CF3CH2 | H | CH | O | |
| 1-101 | 3,5-diCl | CF3 | H | CF3CH2 | H | N | O | |
| 1-102 | 3,4,5-triCl | CF3 | CF3 | 2-PyridylCH2 | H | CH | O | |

TABLE 2

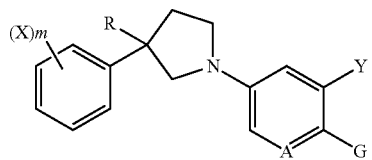

G1 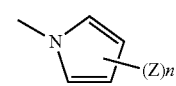

G2 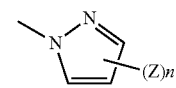

G3 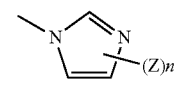

G4 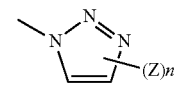

TABLE 2-continued

G5 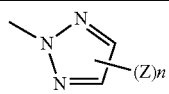

G6 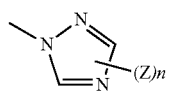

G7 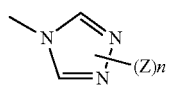

G8 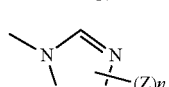

G9 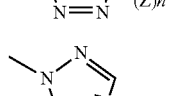

| | (X)m | R | Y | G | Z | A | m.p. ° C. |
|---|---|---|---|---|---|---|---|
| 2-1 | 3,5-diCl | CF3 | H | G1 | H | CH | |
| 2-2 | 3,5-diCl | CF3 | H | G2 | H | CH | |

TABLE 2-continued

| | | | | | | |
|---|---|---|---|---|---|---|
| 2-3 | 3,5-diCl | CF3 | H | G3 | H | CH |
| 2-4 | 3,5-diCl | CF3 | H | G4 | H | CH |
| 2-5 | 3,5-diCl | CF3 | H | G5 | H | CH |
| 2-6 | 3,5-diCl | CF3 | H | G6 | H | CH |
| 2-7 | 3,5-diCl | CF3 | H | G7 | H | CH |
| 2-8 | 3,5-diCl | CF3 | H | G8 | H | CH |
| 2-9 | 3,5-diCl | CF3 | H | G9 | H | CH |
| 2-10 | 3,5-diCl | CF3 | F | G6 | H | CH |
| 2-11 | 3,5-diCl | CF3 | F | G8 | H | CH |
| 2-12 | 3,5-diCl | CF3 | F | G9 | H | CH |
| 2-13 | 3,5-diCl | CF3 | Cl | G6 | H | CH |
| 2-14 | 3,5-diCl | CF3 | Cl | G8 | H | CH |
| 2-15 | 3,5-diCl | CF3 | Cl | G9 | H | CH |
| 2-16 | 3,5-diCl | CF3 | Br | G1 | H | CH |
| 2-17 | 3,5-diCl | CF3 | Br | G2 | H | CH |
| 2-18 | 3,5-diCl | CF3 | Br | G3 | H | CH |
| 2-19 | 3,5-diCl | CF3 | Br | G4 | H | CH |
| 2-20 | 3,5-diCl | CF3 | Br | G5 | H | CH |
| 2-21 | 3,5-diCl | CF3 | Br | G6 | H | CH |
| 2-22 | 3,5-diCl | CF3 | Br | G7 | H | CH |
| 2-23 | 3,5-diCl | CF3 | Br | G8 | H | CH 193-194 |
| 2-24 | 3,5-diCl | CF3 | Br | G9 | H | CH |
| 2-25 | 3,5-diCl | CF3 | I | G6 | H | CH |
| 2-26 | 3,5-diCl | CF3 | I | G8 | H | CH |
| 2-27 | 3,5-diCl | CF3 | I | G9 | H | CH |
| 2-28 | 3,5-diCl | CF3 | Me | G6 | H | CH |
| 2-29 | 3,5-diCl | CF3 | Me | G8 | H | CH |
| 2-30 | 3,5-diCl | CF3 | CF3 | G6 | H | CH |
| 2-31 | 3,5-diCl | CF3 | CF3 | G8 | H | CH |
| 2-32 | 3,5-diCl | CF3 | NO2 | G6 | H | CH |
| 2-33 | 3,5-diCl | CF3 | NO2 | G8 | H | CH |
| 2-34 | 3,5-diCl | CF3 | CN | G1 | H | CH |
| 2-35 | 3,5-diCl | CF3 | CN | G2 | H | CH |
| 2-36 | 3,5-diCl | CF3 | CN | G3 | H | CH |
| 2-37 | 3,5-diCl | CF3 | CN | G4 | H | CH |
| 2-38 | 3,5-diCl | CF3 | CN | G5 | H | CH |
| 2-39 | 3,5-diCl | CF3 | CN | G6 | H | CH |
| 2-40 | 3,5-diCl | CF3 | CN | G7 | H | CH |
| 2-41 | 3,5-diCl | CF3 | CN | G8 | H | CH 192-193 |
| 2-42 | 3,5-diCl | CF3 | CN | G9 | H | CH |
| 2-43 | 3,5-diCl | CF3 | NO2 | G6 | H | CH |
| 2-44 | 3,5-diCl | CF3 | NO2 | G8 | H | CH |
| 2-45 | 3,5-diCl | CF3 | CH3 | G6 | H | CH |
| 2-45 | 3,5-diCl | CF3 | MeS | G6 | H | CH |
| 2-47 | 3,5-diCl | CF3 | MeSO | G6 | H | CH |
| 2-48 | 3,5-diCl | CF3 | MeSO2 | G6 | H | CH |
| 2-49 | 3,5-diCl | CF3 | CF3S | G6 | H | CH |
| 2-50 | 3,5-diCl | CF3 | CF3S(O) | G6 | H | CH |
| 2-51 | 3,5-diCl | CF3 | CF3S(O)2 | G6 | H | CH |
| 2-52 | 3,5-diCl | CF3 | OCH3 | G6 | H | CH |
| 2-53 | 3,5-diCl | CF3 | OCF3 | G6 | H | CH |
| 2-54 | 3,5-diCl | CF3 | OH | G6 | H | CH |
| 2-55 | 3,5-diCl | CF3 | SH | G6 | H | CH |
| 2-56 | 3,5-diCl | CF3 | NH2 | G6 | H | CH |
| 2-57 | 3,5-diCl | CF3 | NHCOCH3 | G6 | H | CH |
| 2-58 | 3,5-diCl | CF3 | NHCO2CH3 | G6 | H | CH |
| 2-59 | 3,5-diCl | CF3 | NHCO2CH2CCl3 | G6 | H | CH |
| 2-60 | 3,5-diCl | CF3 | CN | G2 | 3-NO2 | CH |
| 2-61 | 3,5-diCl | CF3 | CN | G2 | 3-CN | CH |
| 2-62 | 3,5-diCl | CF3 | CN | G6 | 3-NO2 | CH |
| 2-63 | 3,5-diCl | CF3 | CN | G6 | 3-CN | CH |
| 2-64 | 3,5-diCl | CF3 | CN | G2 | Cl | CH |
| 2-65 | 3,5-diCl | CF3 | CN | G2 | Br | CH |
| 2-66 | 3,5-diCl | CF3 | CN | G2 | CH3 | CH |
| 2-67 | 3,5-diCl | CF3 | CN | G2 | CF3 | CH |
| 2-68 | 3-Cl | CF3 | CN | G6 | H | CH |
| 2-89 | 3-Cl | CF3 | CN | G8 | H | CH |
| 2-70 | 3-CF3 | CF3 | CN | G6 | H | CH |
| 2-71 | 3-CF3 | CF3 | CN | G8 | H | CH |
| 2-72 | 3,5-diCF3 | CF3 | CN | G6 | H | CH |
| 2-73 | 3,5-diCF3 | CF3 | CN | G8 | H | CH |
| 2-74 | 3-NO2 | CF3 | CN | G6 | H | CH |
| 2-75 | 3-NO2 | CF3 | CN | G8 | H | CH |
| 2-76 | 3,4-diCl | CF3 | CN | G6 | H | CH |
| 2-77 | 3,4-diCl | CF3 | CN | G8 | H | CH |
| 2-78 | 3,5-diBr | CF3 | CN | G6 | H | CH |
| 2-79 | 3,5-diBr | CF3 | CN | G8 | H | CH |
| 2-80 | 3,5-diBr | CF3 | Br | G6 | H | CH |
| 2-81 | 3,5-diBr | CF3 | Br | G8 | H | CH |
| 2-82 | 3,4,5-triCl | CF3 | CN | G6 | H | CH |
| 2-83 | 3,4,5-triCl | CF3 | CN | G8 | H | CH |
| 2-84 | 3,4,5-triCl | CF3 | Br | G6 | H | CH |
| 2-85 | 3,4,5-triCl | CF3 | Br | G8 | H | CH |
| 2-86 | 3,5-diMe-4-NO2 | CF3 | CN | G8 | H | CH |
| 2-87 | 3-CH3 | CF3 | CN | G6 | H | CH |
| 2-88 | 3-CH3O | CF3 | CN | G6 | H | CH |
| 2-89 | 3-CN | CF3 | CN | G6 | H | CH |
| 2-90 | 3-CF3O | CF3 | CN | G6 | H | CH |
| 2-91 | 3-CF3O | CF3 | CN | G8 | H | CH |
| 2-92 | 3-CH3S | CF3 | CN | G6 | H | CH |
| 2-93 | 3-CH3S | CF3 | CN | G8 | H | CH |
| 2-94 | 3-CH3S(O) | CF3 | CN | G6 | H | CH |
| 2-95 | 3-CH3S(O)2 | CF3 | CN | G6 | H | CH |
| 2-96 | 3-CF3S | CF3 | CN | G6 | H | CH |
| 2-97 | 3-CF3S(O) | CF3 | CN | G6 | H | CH |
| 2-98 | 3-CF3S(O)2 | CF3 | CN | G6 | H | CH |
| 2-99 | 3-OH | CF3 | CN | G6 | H | CH |
| 2-100 | 3-SH | CF3 | CN | G6 | H | CH |
| 2-101 | 3,5-diCl | CH3 | Br | G6 | H | CH |
| 2-102 | 3,5-diCl | CH3 | Br | G8 | H | CH |
| 2-103 | 3,5-diCl | CF3 | Br | G6 | H | N |
| 2-104 | 3,5-diCl | CF3 | Br | G8 | H | N |
| 2-105 | 3,5-diCl | CF3 | CN | G6 | H | N |
| 2-106 | 3,5-diCl | CF3 | CN | G8 | H | N |
| 2-107 | 3,5-diCl | CF3 | C=NOCH3 | G6 | H | CH |
| 2-108 | 3,5-diCl | CF3 | C=NOCH3 | G8 | H | CH |
| 2-109 | 3,5-diCl | CF3 | NHSO2CH3 | G6 | H | CH |
| 2-110 | 3,5-diCl | CF3 | NHSO2CH3 | G8 | H | CH |
| 2-111 | 3,5-diCl | CF3 | NHSO2CF3 | G6 | H | CH |
| 2-112 | 3,5-diCl | CF3 | NHSO2CF3 | G8 | H | CH |

TABLE 3

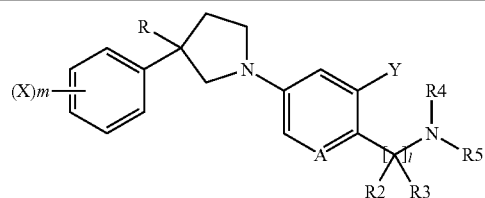

| | (X)m | R | Y | R2 | R3 | R4 | R5 | A | l | m.p. ° C.) |
|---|---|---|---|---|---|---|---|---|---|---|
| 3-1 | 3,5-diCl | CF3 | H | H | H | H | COCH3 | CH | 1 | |
| 3-2 | 3,5-diCl | CF3 | H | H | H | H | COC2H5 | CH | 1 | |
| 3-3 | 3,5-diCl | CF3 | Cl | H | H | H | COCH3 | CH | 1 | |
| 3-4 | 3,5-diCl | CF3 | Br | H | H | H | COCH3 | CH | 1 | |
| 3-5 | 3,5-diCl | CF3 | Br | H | H | H | COC2H5 | CH | 1 | |
| 3-6 | 3,5-diCl | CF3 | Br | H | H | H | CO(i-Pr) | CH | 1 | |

TABLE 3-continued

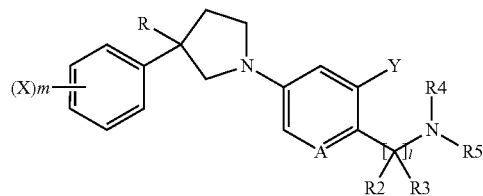

| | (X)m | R | Y | R2 | R3 | R4 | R5 | A | l | m.p. °C.) |
|---|---|---|---|---|---|---|---|---|---|---|
| 3-7 | 3,5-diCl | CF3 | Br | H | H | H | CO2-pyridyl | CH | 1 | |
| 3-8 | 3,5-diCl | CF3 | F | H | H | H | COCH3 | CH | 1 | |
| 3-9 | 3,5-diCl | CF3 | I | H | H | H | COCH3 | CH | 1 | |
| 3-10 | 3,5-diCl | CF3 | NO2 | H | H | H | COCH3 | CH | 1 | |
| 3-11 | 3,5-diCl | CF3 | CH3 | H | H | H | COCH3 | CH | 1 | |
| 3-12 | 3,5-diCl | CF3 | MeS | H | H | H | COCH3 | CH | 1 | |
| 3-13 | 3,5-diCl | CF3 | MeSO | H | H | H | COCH3 | CH | 1 | |
| 3-14 | 3,5-diCl | CF3 | MeSO2 | H | H | H | COCH3 | CH | 1 | |
| 3-15 | 3,5-diCl | CF3 | CF3S | H | H | H | COCH3 | CH | 1 | |
| 3-16 | 3,5-diCl | CF3 | CF3S(O) | H | H | H | COCH3 | CH | 1 | |
| 3-17 | 3,5-diCl | CF3 | CF3S(O)2 | H | H | H | COCH3 | CH | 1 | |
| 3-18 | 3,5-diCl | CF3 | OCH3 | H | H | H | COCH3 | CH | 1 | |
| 3-19 | 3,5-diCl | CF3 | OCF3 | H | H | H | COCH3 | CH | 1 | |
| 3-20 | 3,5-diCl | CF3 | OH | H | H | H | COCH3 | CH | 1 | |
| 3-21 | 3,5-diCl | CF3 | SH | H | H | H | COCH3 | CH | 1 | |
| 3-22 | 3,5-diCl | CF3 | NH2 | H | H | H | COCH3 | CH | 1 | |
| 3-23 | 3,5-diCl | CF3 | NHCOCH3 | H | H | H | COCH3 | CH | 1 | |
| 3-24 | 3,5-diCl | CF3 | NHCO2CH3 | H | H | H | COCH3 | CH | 1 | |
| 3-25 | 3,5-diCl | CF3 | NHCO2CH2CCl3 | H | H | H | COCH3 | CH | 1 | |
| 3-26 | 3,5-diCl | CF3 | Cl | H | H | Me | CO2-pyridyl | CH | 1 | |
| 3-27 | 3,5-diCl | CF3 | Cl | H | H | Me | COCH3 | CH | 1 | |
| 3-28 | 3,5-diCl | CF3 | Cl | H | H | Et | COCH3 | CH | 1 | |
| 3-29 | 3,5-diCl | CF3 | Cl | H | H | vinyl | COCH3 | CH | 1 | |
| 3-30 | 3,5-diCl | CF3 | Cl | H | H | propargyl | COCH3 | CH | 1 | |
| 3-31 | 3,5-diCl | CF3 | Cl | H | H | CH2Ph | COCH3 | CH | 1 | |
| 3-32 | 3,5-diCl | CF3 | Cl | H | H | CN | COCH3 | CH | 1 | |
| 3-33 | 3,5-diCl | CF3 | Cl | H | H | CH2CF3 | COCH3 | CH | 1 | |
| 3-34 | 3,5-diCl | CF3 | Cl | H | H | cycloPr | COCH3 | CH | 1 | |
| 3-35 | 3,5-diCl | CF3 | Cl | H | H | COCH3 | COCH3 | CH | 1 | |
| 3-36 | 3,5-diCl | CF3 | Cl | H | H | H | COC2H5 | CH | 1 | |
| 3-37 | 3,5-diCl | CF3 | Cl | H | H | H | COC2F5 | CH | 1 | |
| 3-38 | 3,5-diCl | CF3 | Cl | H | H | H | COPh | CH | 1 | |
| 3-39 | 3,5-diCl | CF3 | Cl | H | H | H | CO2-pyridyl | CH | 1 | |
| 3-40 | 3,5-diCl | CF3 | Cl | H | H | H | CONMe2 | CH | 1 | |
| 3-41 | 3,5-diCl | CF3 | Cl | H | H | H | CO2Me | CH | 1 | |
| 3-42 | 3,5-diCl | CF3 | Cl | H | H | H | COSMe | CH | 1 | |
| 3-43 | 3,5-diCl | CF3 | Cl | H | H | Me | COCH3 | CH | 1 | |
| 3-44 | 3,5-diCl | CF3 | Cl | H | H | 2-pyridylCO | COCH3 | CH | 1 | |
| 3-45 | 3,5-diBr | CF3 | Cl | H | H | H | COCH3 | CH | 1 | |
| 3-46 | 3-Cl | CF3 | Cl | H | H | H | COCH3 | CH | 1 | |
| 3-47 | 3-CF3 | CF3 | Cl | H | H | H | COCH3 | CH | 1 | |
| 3-48 | 3,5-diCF3 | CF3 | Cl | H | H | H | COCH3 | CH | 1 | |
| 3-49 | 3,4,5-triCl | CF3 | Cl | H | H | H | COCH3 | CH | 1 | |
| 3-50 | 3,5-diMe-4-NO2 | CF3 | Cl | H | H | H | COCH3 | CH | 1 | |
| 3-51 | 3-NO2 | CF3 | Cl | H | H | H | COCH3 | CH | 1 | |
| 3-52 | 3,5-diCl | CF3 | Cl | H | H | H | COCH3 | N | 1 | |
| 3-53 | 3-CH3 | CF3 | Cl | H | H | H | COCH3 | CH | 1 | |
| 3-54 | 3-CH3O | CF3 | Cl | H | H | H | COCH3 | CH | 1 | |
| 3-55 | 3-CN | CF3 | Cl | H | H | H | COCH3 | CH | 1 | |
| 3-56 | 3-CF3O | CF3 | Cl | H | H | H | COCH3 | CH | 1 | |
| 3-57 | 3-CH3S | CF3 | Cl | H | H | H | COCH3 | CH | 1 | |
| 3-58 | 3-CH3S(O) | CF3 | Cl | H | H | H | COCH3 | CH | 1 | |
| 3-59 | 3-CH3S(O)2 | CF3 | Cl | H | H | H | COCH3 | CH | 1 | |
| 3-60 | 3-CF3S | CF3 | Cl | H | H | H | COCH3 | CH | 1 | |
| 3-61 | 3-CF3S(O) | CF3 | Cl | H | H | H | COCH3 | CH | 1 | |
| 3-62 | 3-CF3S(O)2 | CF3 | Cl | H | H | H | COCH3 | CH | 1 | |
| 3-63 | 3-OH | CF3 | Cl | H | H | H | COCH3 | CH | 1 | |
| 3-64 | 3-SH | CF3 | Cl | H | H | H | COCH3 | CH | 1 | |
| 3-65 | 3,5-diCl | CF3 | Cl | CN | H | H | COCH3 | CH | 1 | |
| 3-66 | 3,5-diCl | CF3 | Cl | Me | H | H | COCH3 | CH | 1 | |
| 3-67 | 3,5-diCl | CF3 | Cl | Me | Me | H | COCH3 | CH | 1 | |
| 3-68 | 3,5-diCl | CF3 | Cl | cyclo-Pr | H | H | COCH3 | CH | 1 | |
| 3-69 | 3,5-diCl | CF3 | Cl | CF3 | H | H | COCH3 | CH | 1 | |
| 3-70 | 3,5-diCl | CF3 | Cl | CO2Me | H | H | COCH3 | CH | 1 | |
| 3-71 | 3,5-diCl | CF3 | Cl | CH=CH2 | H | H | COCH3 | CH | 1 | |
| 3-72 | 3,5-diCl | CF3 | Cl | CH2CH2 | H | H | COCH3 | CH | 1 | |

TABLE 3-continued

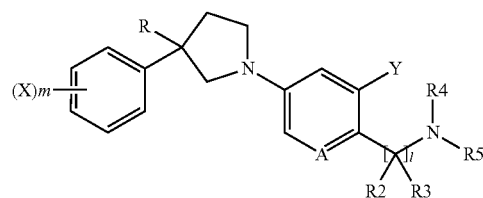

| | (X)m | R | Y | R2 | R3 | R4 | R5 | A | l | m.p. ° C.) |
|---|---|---|---|---|---|---|---|---|---|---|
| 3-73 | 3,5-diCl | CF3 | Cl | CCH | H | H | COCH3 | CH | 1 | |
| 3-74 | 3,5-diCl | CF3 | Br | H | H | H | COEt | CH | 1 | |
| 3-75 | 3,5-diCl | CF3 | Br | H | H | H | COPr-n | CH | 1 | |
| 3-76 | 3,5-diCl | CF3 | Br | H | H | H | COPr-iso | CH | 1 | |
| 3-77 | 3,5-diCl | CF3 | Br | H | H | H | COBu-tert | CH | 1 | |
| 3-78 | 3,5-diCl | CF3 | Br | H | H | H | COCF3 | CH | 1 | |
| 3-79 | 3,5-diCl | CF3 | Br | H | H | H | COPh | CH | 1 | |
| 3-80 | 3,5-diCl | CF3 | Br | H | H | H | COpyridyl-2 | CH | 1 | |
| 3-81 | 3,5-diCl | CF3 | Br | H | H | H | COpyridyl-3 | CH | 1 | |
| 3-82 | 3,5-diCl | CF3 | Br | H | H | H | COpyridylCO-4 | CH | 1 | |
| 3-83 | 3,5-diCl | CF3 | Br | H | H | H | COPh—F-2 | CH | 1 | |
| 3-84 | 3,5-diCl | CF3 | Br | H | H | H | COPh—F-3 | CH | 1 | |
| 3-85 | 3,5-diCl | CF3 | Br | H | H | H | COPh—F-4 | CH | 1 | |
| 3-86 | 3,5-diCl | CF3 | Br | H | H | H | COPh—Cl-2 | CH | 1 | |
| 3-87 | 3,5-diCl | CF3 | Br | H | H | H | COPh—Cl-3 | CH | 1 | |
| 3-88 | 3,5-diCl | CF3 | Br | H | H | H | COPh—Cl-4 | CH | 1 | |
| 3-89 | 3,5-diCl | CF3 | Br | H | H | H | COPh—Br-2 | CH | 1 | |
| 3-90 | 3,5-diCl | CF3 | Br | H | H | H | COPh—Me-2 | CH | 1 | |
| 3-91 | 3,5-diCl | CF3 | Br | H | H | H | COvinyl | CH | 1 | |
| 3-92 | 3,5-diCl | CF3 | Br | H | H | H | COpropargyl | CH | 1 | |
| 3-93 | 3,5-diCl | CF3 | Br | H | H | H | MeSO2 | CH | 1 | |
| 3-94 | 3,5-diCl | CF3 | Br | H | H | H | CF3SO2 | CH | 1 | |
| 3-95 | 3,5-diCl | CF3 | Br | H | H | H | CONHMe | CH | 1 | |
| 3-96 | 3,5-diCl | CF3 | Br | H | H | H | CONMe2 | CH | 1 | |
| 3-97 | 3,5-diCl | CF3 | Br | H | H | H | CO2Me | CH | 1 | |
| 3-98 | 3,5-diCl | CF3 | Br | H | H | H | C(O)SMe | CH | 1 | |
| 3-99 | 3,5-diCl | CF3 | Br | H | H | H | CSMe | CH | 1 | |
| 3-100 | 3,5-diCl | CF3 | Br | H | H | H | CON(Me)OMe | CH | 1 | |
| 3-101 | 3,5-diCl | CH3 | Br | H | H | H | COCH3 | CH | 1 | |
| 3-102 | 3,5-diCl | CH3 | CF3 | H | H | H | COCH3 | CH | 1 | |
| 3-103 | 3,5-diCl | CH3 | CN | H | H | H | COCH3 | CH | 1 | |
| 3-104 | 3,5-diCl | CH3 | NH2 | H | H | H | COCH3 | CH | 1 | |
| 3-105 | 3,5-diCl | CH3 | NHCOCH3 | H | H | H | COCH3 | CH | 1 | |
| 3-106 | 3,5-diCl | CH3 | NHCOCF3 | H | H | H | COCH3 | CH | 1 | |
| 3-107 | 3,5-diCl | CH3 | NHCO2CH3 | H | H | H | COCH3 | CH | 1 | |
| 3-108 | 3,5-diCl | CH3 | NHCO2CH2CCl3 | H | H | H | COCH3 | CH | 1 | |
| 3-109 | 3,5-diCl | CH3 | NHSO2CH3 | H | H | H | COCH3 | CH | 1 | |
| 3-110 | 3,5-diCl | CH3 | NHSO2CF3 | H | H | H | COCH3 | CH | 1 | |
| 3-111 | 3,5-diCl | CH3 | C=NOCH3 | H | H | H | COCH3 | CH | 1 | |
| 3-112 | 3,5-diCl | CF3 | Br | H | H | H | COCH3 | CH | 2 | |
| 3-113 | 3,5-diCF3 | CF3 | CF3 | H | H | H | COCH3 | CH | 1 | |
| 3-114 | 3,5-diCF3 | CF3 | CF3 | H | H | H | COC2H5 | CH | 1 | |
| 3-115 | 3,5-diCF3 | CF3 | CF3 | H | H | H | COPr-cyclo | CH | 1 | |
| 3-116 | 3,4,5-triCl | CF3 | CF3 | H | H | H | COCH3 | CH | 1 | |
| 3-117 | 3,4,5-triCl | CF3 | CF3 | H | H | H | COC2H5 | CH | 1 | |
| 3-118 | 3,4,5-triCl | CF3 | CF3 | H | H | H | COPr-cyclo | CH | 1 | |
| 3-119 | 3,4-diCl, 5-CF3 | CF3 | CF3 | H | H | H | COCH3 | CH | 1 | |

TABLE 4

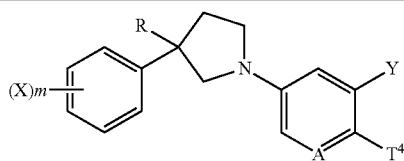

| | (X)m | R | Y | T4 | A | m.p. ° C.) |
|---|---|---|---|---|---|---|
| 4-1 | 3,5-diCl | CF3 | H | NO2 | CH | |
| 4-2 | 3,5-diCl | CF3 | H | CN | CH | |

TABLE 4-continued

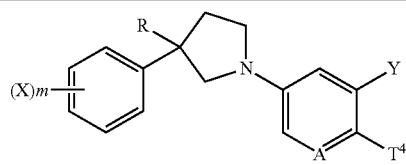

| | (X)m | R | Y | T4 | A | m.p. ° C.) |
|---|---|---|---|---|---|---|
| 4-3 | 3,5-diCl | CF3 | H | NH2 | CH | |
| 4-4 | 3,5-diCl | CF3 | H | CO2Et | CH | 161-163 |

TABLE 4-continued

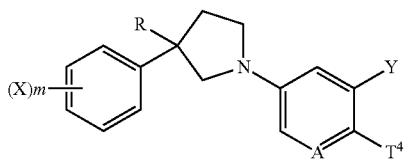

| | (X)m | R | Y | T⁴ | A | m.p. ° C. |
|---|---|---|---|---|---|---|
| 4-5 | 3,5-diCl | CF3 | H | CO2H | CH | |
| 4-6 | 3,5-diCl | CF3 | NO2 | CO2Me | CH | |
| 4-7 | 3,5-diCl | CF3 | NO2 | CO2H | CH | |
| 4-8 | 3,5-diCl | CF3 | NH2 | CO2Me | CH | |
| 4-9 | 3,5-diCl | CF3 | F | CO2Me | CH | |
| 4-10 | 3,5-diCl | CF3 | Cl | CO2Me | CH | |
| 4-11 | 3,5-diCl | CF3 | Cl | CO2Bu-t | CH | |
| 4-12 | 3,5-diCl | CF3 | Cl | CO2H | CH | |
| 4-13 | 3,5-diCl | CF3 | Br | CO2Me | CH | |
| 4-14 | 3,5-diCl | CF3 | I | CO2Me | CH | |
| 4-15 | 3,5-diCl | CF3 | CH3 | CO2Me | CH | |
| 4-16 | 3,5-diCl | CF3 | Cl | CH3 | CH | |
| 4-17 | 3,5-diCl | CF3 | CN | F | CH | 184-186 |
| 4-18 | 3,5-diCl | CF3 | CH3 | NO2 | CH | |
| 4-19 | 3,5-diCl | CF3 | CH3 | NH2 | CH | |
| 4-20 | 3,5-diCl | CF3 | Br | NO2 | CH | |
| 4-21 | 3,5-diCl | CF3 | Br | NH2 | CH | |
| 4-22 | 3-CF3 | CF3 | NO2 | CO2Me | CH | 146-148 |
| 4-23 | 3-CF3 | CF3 | NO2 | CO2H | CH | |
| 4-24 | 3,5-diCF3 | CF3 | NO2 | CO2Me | CH | |
| 4-25 | 3,5-diCF3 | CF3 | NO2 | CO2H | CH | |
| 4-26 | 3,4-diCl | CF3 | NO2 | CO2Me | CH | |
| 4-27 | 3,4-diCl | CF3 | NO2 | CO2H | CH | |
| 4-28 | 3-Cl | CF3 | NO2 | CO2Me | CH | 142-144 |
| 4-29 | 3-Cl | CF3 | NO2 | CO2H | CH | |
| 4-30 | 3,5-diBr | CF3 | NO2 | CO2Me | CH | |
| 4-31 | 3,4,5-triCl | CF3 | NO2 | CO2Me | CH | |
| 4-32 | 3,5-diMe-4-NO2 | CF3 | NO2 | CO2Me | CH | |
| 4-33 | 3-NO2 | CF3 | NO2 | CO2Me | CH | |
| 4-34 | 3-CH3 | CF3 | NO2 | CO2Me | CH | |
| 4-35 | 3-CH3O | CF3 | NO2 | CO2Me | CH | |
| 4-36 | 3-CN | CF3 | NO2 | CO2Me | CH | |
| 4-37 | 3-CF3O | CF3 | NO2 | CO2Me | CH | |
| 4-38 | 3-CH3S | CF3 | NO2 | CO2Me | CH | |
| 4-39 | 3-CH3S(O) | CF3 | NO2 | CO2Me | CH | |
| 4-40 | 3-CH3S(O)2 | CF3 | NO2 | CO2Me | CH | |
| 4-41 | 3-CF3S | CF3 | NO2 | CO2Me | CH | |
| 4-42 | 3-CF3S(O) | CF3 | NO2 | CO2Me | CH | |
| 4-43 | 3-CF3S(O)2 | CF3 | NO2 | CO2Me | CH | |
| 4-44 | 3-OH | CF3 | NO2 | CO2Me | CH | |
| 4-45 | 3-SH | CF3 | NO2 | CO2Me | CH | |
| 4-46 | 3,5-diCl | CF3 | H | CO2Me | N | |
| 4-47 | 3-NO2 | CF3 | NO2 | CO2H | CH | |
| 4-48 | 3,4,5-triCl | CF3 | NO2 | CO2H | CH | |
| 4-49 | 2-Cl | CF3 | NO2 | CO2Me | CH | |
| 4-50 | 2-Cl | CF3 | NO2 | CO2H | CH | |
| 4-51 | 4-Cl | CF3 | NO2 | CO2Me | CH | |
| 4-52 | 4-Cl | CF3 | NO2 | CO2H | CH | |
| 4-53 | 3,5-diCl | CF3 | CF3 | CO2Et | CH | |
| 4-54 | 3,5-diCl | CF3 | CF3 | CO2H | CH | |
| 4-55 | 3,5-diMe-4-NO2 | CF3 | NO2 | CO2H | CH | |
| 4-56 | 3,4,5-triCl | CF3 | NO2 | CO2Me | CH | |
| 4-57 | 3,5-diCl | CF3 | CN | CO2H | CH | |
| 4-58 | 3,5-diCl | CF3 | CN | CO2Me | CH | |
| 4-59 | 3,5-diCl | CF3 | H | CO2Bu-t | N | |
| 4-60 | 3,5-diCl | CF3 | H | CO2H | N | |
| 4-61 | 3,5-diCF3 | CF3 | CF3 | CO2Et | CH | |
| 4-62 | 3,5-diCl | CF3 | CF3 | F | CH | |
| 4-63 | 3,5-diCl | CF3 | CF3 | NO2 | CH | |
| 4-64 | 3,5-diCl | CF3 | CF3 | NH2 | CH | |
| 4-65 | 3,5-diCl | CF3 | F | CO2Et | CH | |
| 4-66 | 3,4,5-triCl | CF3 | CF3 | CO2Et | CH | |
| 4-67 | 3,4,5-triCl | CF3 | CF3 | CO2H | CH | |

TABLE 5

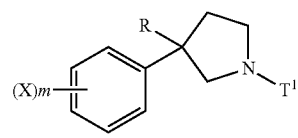

| | (X)m | R | T¹ | m.p. ° C. |
|---|---|---|---|---|
| 5-1 | 2-Cl | CF3 | CH2Ph | |
| 5-2 | 2-Cl | CF3 | H | |
| 5-3 | 3-Cl | CF3 | CH2Ph | |
| 5-4 | 3-Cl | CF3 | H | |
| 5-5 | 4-Cl | CF3 | CH2Ph | |
| 5-6 | 4-Cl | CF3 | H | |
| 5-7 | 2,3-diCl | CF3 | CH2Ph | |
| 5-8 | 2,3-diCl | CF3 | H | |
| 5-9 | 3,4-diCl | CF3 | CH2Ph | |
| 5-10 | 3,4-diCl | CF3 | H | |
| 5-11 | 3,5-diCl | CF3 | CH2Ph | |
| 5-12 | 3,5-diCl | CF3 | H | |
| 5-13 | 3,5-diCl | CF3 | H, HCl salt | |
| 5-14 | 3,4,5-triCl | CF3 | CH2Ph | |
| 5-15 | 3,4,5-triCl | CF3 | H | |
| 5-16 | 3-CF3 | CF3 | CH2Ph | |
| 5-17 | 3-CF3 | CF3 | H | |
| 5-18 | 3,5-diCF3 | CF3 | CH2Ph | |
| 5-19 | 3,5-diCF3 | CF3 | H | |
| 5-20 | 3-Br | CF3 | CH2Ph | |
| 5-21 | 3-Br | CF3 | H | |
| 5-22 | 3,5-diBr | CF3 | CH2Ph | |
| 5-23 | 3,5-diBr | CF3 | H | |
| 5-24 | 3-NO2 | CF3 | CH2Ph | |
| 5-25 | 3-NO2 | CF3 | H | |
| 5-26 | 3,5-diMe-4-NO2 | CF3 | CH2Ph | |
| 5-27 | 3,5-diMe-4-NO2 | CF3 | H | |
| 5-28 | 3-CN | CF3 | CH2Ph | |
| 5-29 | 3-CN | CF3 | H | |
| 5-30 | 3-OCF₃ | CF3 | CH2Ph | |
| 5-31 | 3-OCF₃ | CF3 | H | |
| 5-32 | 3-SCF₃ | CF3 | CH2Ph | |
| 5-33 | 3-SCF₃ | CF3 | H | |
| 5-34 | 3-S(O)CF₃ | CF3 | CH2Ph | |
| 5-35 | 3-S(O)CF₃ | CF3 | H | |
| 5-36 | 3-S(O)₂CF₃ | CF3 | CH2Ph | |
| 5-37 | 3-S(O)₂CF₃ | CF3 | H | |
| 5-38 | 3,4-diCl, 5-CF3 | CF3 | CH2Ph | |
| 5-39 | 3,4-diCl, 5-CF3 | CF3 | H | |

TABLE 6

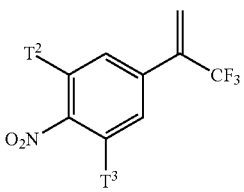

| | T² | T³ | m.p. ° C. |
|---|---|---|---|
| 6-1 | CH3 | CH3 | |
| 6-2 | CH3 | CH2CH3 | |
| 6-3 | CH2CH3 | CH2CH3 | |
| 6-4 | n-Pr | n-Pr | |
| 6-5 | iso-Pr | iso-Pr | |
| 6-6 | cyclo-Pr | cyclo-Pr | |
| 6-7 | n-Bu | n-Bu | |
| 6-8 | tert-Bu | tert-Bu | |
| 6-9 | n-Pen | n-Pen | |

TABLE 7

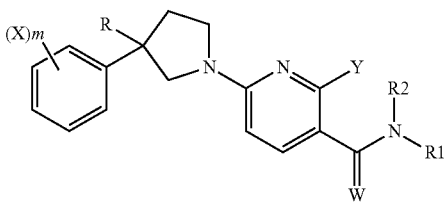

| | (X)m | R | Y | R1 | R2 | W | m.p. ° C.) |
|---|---|---|---|---|---|---|---|
| 7-1 | 3,5-diCl | CF3 | H | CF3CH2 | H | O | |
| 7-2 | 3,5-diCl | CF3 | H | 2-PyridylCH2 | H | O | |
| 7-3 | 3,5-diCl | CF3 | CH3 | CF3CH2 | H | O | |
| 7-4 | 3,5-diCl | CF3 | CH3 | 2-PyridylCH2 | H | O | |
| 7-5 | 3,5-diCl | CF3 | F | CF3CH2 | H | O | |
| 7-6 | 3,5-diCl | CF3 | F | 2-PyridylCH2 | H | O | |
| 7-7 | 3,5-diCl | CF3 | Cl | CF3CH2 | H | O | |
| 7-8 | 3,5-diCl | CF3 | Cl | 2-PyridylCH2 | H | O | |
| 7-9 | 3,5-diCl | CF3 | Br | CF3CH2 | H | O | |
| 7-10 | 3,5-diCl | CF3 | Br | 2-PyridylCH2 | H | O | |
| 7-11 | 3,5-diCl | CF3 | Br | cyclo-Pr | H | O | |
| 7-12 | 3,5-diCl | CF3 | Br | NCCH2CH2 | H | O | |
| 7-13 | 3,5-diCl | CF3 | I | CF3CH2 | H | O | |
| 7-14 | 3,5-diCl | CF3 | I | 2-PyridylCH2 | H | O | |
| 7-15 | 3,5-diCl | CF3 | NO2 | CF3CH2 | H | O | |
| 7-16 | 3,5-diCl | CF3 | NO2 | 2-PyridylCH2 | H | O | |
| 7-17 | 3-Cl | CF3 | NO2 | 2-PyridylCH2 | H | O | |
| 7-18 | 3-Cl | CF3 | NO2 | CF3CH2 | H | O | |
| 7-19 | 3-Br | CF3 | NO2 | 2-PyridylCH2 | H | O | |
| 7-20 | 3-CF3 | CF3 | NO2 | 2-PyridylCH2 | H | O | |
| 7-21 | 3-CF3 | CF3 | NO2 | CF3CH2 | H | O | |
| 7-22 | 3,5-diCF3 | CF3 | NO2 | 2-PyridylCH2 | H | O | |
| 7-23 | 3,5-diCF3 | CF3 | NO2 | CF3CH2 | H | O | |
| 7-24 | 3-NO2 | CF3 | NO2 | 2-PyridylCH2 | H | O | |
| 7-25 | 3,5-diCl | CF3 | CF3 | 2-PyridylCH2 | H | O | |
| 7-26 | 3,5-diCl | CF3 | CF3 | CF3CH2 | H | O | |
| 7-27 | 3,5-diCl | CF3 | CH3O | 2-PyridylCH2 | H | O | |
| 7-28 | 3,5-diCl | CF3 | CN | 2-PyridiylCH2 | H | O | |
| 7-29 | 3,5-diCl | CF3 | CF3O | 2-PyridylCH2 | H | O | |
| 7-30 | 3,5-diCl | CF3 | CH3S | 2-PyridylCH2 | H | O | |
| 7-31 | 3,5-diCl | CF3 | CH3S(O) | 2-PyridylCH2 | H | O | |
| 7-32 | 3,5-diCl | CF3 | CH3S(O)2 | 2-PyridylCH2 | H | O | |
| 7-33 | 3,5-diCl | CF3 | CF3S | 2-PyridylCH2 | H | O | |
| 7-34 | 3,5-diCl | CF3 | CF3S(O) | 2-PyridylCH2 | H | O | |
| 7-35 | 3,5-diCl | CF3 | CF3S(O)2 | 2-PyridylCH2 | H | O | |
| 7-36 | 3,5-diCl | CF3 | OH | 2-PyridylCH2 | H | O | |
| 7-37 | 3,5-diCl | CF3 | SH | 2-PyridylCH2 | H | O | |
| 7-38 | 3,5-diCl | CF3 | NH2 | 2-PyridylCH2 | H | O | |
| 7-39 | 3,5-diCl | CF3 | NHCOCH3 | 2-PyridylCH2 | H | O | |
| 7-40 | 3,5-diCl | CF3 | NHCOCF3 | 2-PyridylCH2 | H | O | |
| 7-41 | 3,5-diCl | CF3 | NHCO2CH3 | 2-PyridylCH2 | H | O | |
| 7-42 | 3,5-diCl | CF3 | NHCO2CH2CCl3 | 2-PyridylCH2 | H | O | |
| 7-43 | 3-CH3 | CF3 | H | 2-PyridylCH2 | H | O | |
| 7-44 | 3-CH3O | CF3 | H | 2-PyridylCH2 | H | O | |
| 7-45 | 3-CN | CF3 | H | 2-PyridylCH2 | H | O | |
| 7-46 | 3-CF3O | CF3 | H | 2-PyridylCH2 | H | O | |
| 7-47 | 3-CH3S | CF3 | H | 2-PyridylCH2 | H | O | |
| 7-48 | 3-CH3S(O) | CF3 | H | 2-PyridylCH2 | H | O | |
| 7-49 | 3-CH3S(O)2 | CF3 | H | 2-PyridylCH2 | H | O | |
| 7-50 | 3-CF3S | CF3 | H | 2-PyridylCH2 | H | O | |
| 7-51 | 3-CF3S(O) | CF3 | H | 2-PyridylCH2 | H | O | |
| 7-52 | 3-CF3S(O)2 | CF3 | H | 2-PyridylCH2 | H | O | |
| 7-53 | 3-OH | CF3 | H | 2-PyridylCH2 | H | O | |
| 7-54 | 3-SH | CF3 | H | 2-PyridylCH2 | H | O | |
| 7-55 | 3,4-diCl | CF3 | H | 2-PyridylCH2 | H | O | |
| 7-56 | 3,4-diCl | CF3 | H | CF3CH2 | H | O | |
| 7-57 | 3,4,5-triCl | CF3 | H | 2-PyridylCH2 | H | O | |
| 7-58 | 3,4,5-triCl | CF3 | H | CF3CH2 | H | O | |
| 7-59 | 3,5-diBr | CF3 | H | 2-PyridiCH2 | H | O | |
| 7-60 | 3,5-diBr | CF3 | H | CF3CH2 | H | O | |
| 7-61 | 3,5-diMe-4-NO2 | CF3 | H | 2-PyridylCH2 | H | O | |
| 7-62 | 3,5-diMe-4-NO2 | CF3 | H | CF3CH2 | H | O | |
| 7-63 | 3,5-diCl | CF3 | H | 2-PyridylCH2 | H | O | |
| 7-64 | 3,5-diCl | CF3 | NO2 | H | H | O | |
| 7-65 | 3,5-diCl | CF3 | NO2 | Me | H | O | |
| 7-66 | 3,5-diCl | CF3 | NO2 | iso-Pr | H | O | |
| 7-67 | 3,5-diCl | CF3 | NO2 | PhCH2 | H | O | |

TABLE 7-continued

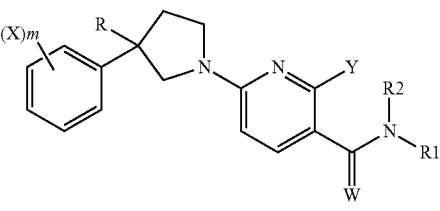

| | (X)m | R | Y | R1 | R2 | W | m.p. ° C.) |
|---|---|---|---|---|---|---|---|
| 7-68 | 3,5-diCl | CF3 | NO2 | CH2CO2CH3 | H | O | |
| 7-69 | 3,5-diCl | CF3 | NO2 | CH2CONMe | H | O | |
| 7-70 | 3,5-diCl | CF3 | NO2 | CH2(cyclo)Pr | H | O | |
| 7-71 | 3,5-diCl | CF3 | NO2 | SO2Me | H | O | |
| 7-72 | 3,5-diCl | CF3 | NO2 | SO2CF3 | H | O | |
| 7-73 | 3,5-diCl | CF3 | NO2 | CH2=CHCH2 | H | O | |
| 7-74 | 3,5-diCl | CF3 | NO2 | HCCCH2 | H | O | |
| 7-75 | 3,5-diCl | CF3 | NO2 | CH2CN | H | O | |
| 7-76 | 3,5-diCl | CF3 | NO2 | C(Me)2CH2SCH3 | H | O | |
| 7-77 | 3,5-diCl | CF3 | NO2 | 2-F—Ph | H | O | |
| 7-78 | 3,5-diCl | CH3 | H | 2-PyridylCH2 | H | O | |
| 7-79 | 3,5-diCl | CF3 | H | 2-PyridylCH2 | CH3 | O | |
| 7-80 | 3-NO2 | CF3 | NO2 | CF3CH2 | H | O | |
| 7-81 | 3,5-diCl | CF3 | Cl | 2-PyridylCH2 | H | S | |
| 7-82 | 2-diCl | CF3 | NO2 | 2-PyridylCH2 | H | O | |
| 7-83 | 2,3-diCl | CF3 | NO2 | 2-PyridylCH2 | H | O | |
| 7-84 | 3,5-diCl | CF3 | NO2 | 3-PyridylCH2 | H | O | |
| 7-85 | 3,5-diCl | CF3 | NO2 | 4-PyridylCH2 | H | O | |
| 7-86 | 3,5-diCl | CF3 | NO2 | 2-(6-Cl-pyridyl)CH2 | H | O | |
| 7-87 | 3,5-diCl | CF3 | NO2 | 3-(6-Cl-pyridyl)CH2 | H | O | |
| 7-88 | 3,5-diCl | CF3 | NO2 | 2-PyrinidinylCH2 | H | O | |
| 7-89 | 3,5-diCl | CF3 | NO2 | 1-(1-ethylpyrrolidin-2-yl)CH2 | H | O | |
| 7-90 | 3,5-diCl | CF3 | CF3 | CF3CH2 | H | O | |
| 7-91 | 3,5-diCl | CF3 | CF3 | 2-(6-Cl-pyridyl)CH2 | H | O | |
| 7-92 | 3,5-diCl | CF3 | NO2 | Me2NCH= | | O | |
| 7-93 | 3,5-diCl | CF3 | NO2 | EtON=CH | | O | |
| 7-94 | 3,5-diCl | CF3 | C=NOCH3 | 2-PyridylCH2 | H | O | |
| 7-95 | 4-Cl | CF3 | NO2 | 2-PyridylCH2 | H | O | |
| 7-96 | 4-Cl | CF3 | NO2 | CF3CH2 | H | O | |
| 7-97 | 3,5-diCl | CF3 | CN | CF3CH2 | H | O | |
| 7-98 | 3,5-diCl | CF3 | CF3 | H | H | O | |
| 7-99 | 3,5-diCF3 | CF3 | CF3 | 2-PyridylCH2 | H | O | |
| 7-100 | 3,5-diCF3 | CF3 | CF3 | CF3CH2 | H | O | |

TABLE 8

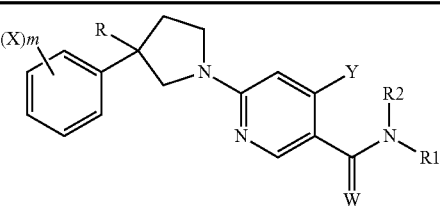

| | (X)m | R | Y | R1 | R2 | W | m.p. ° C.) |
|---|---|---|---|---|---|---|---|
| 8-1 | 3,5-diCl | CF3 | CH3 | CF3CH2 | H | O | |
| 8-2 | 3,5-diCl | CF3 | CH3 | 2-PyridylCH2 | H | O | |
| 8-3 | 3,5-diCl | CF3 | F | CF3CH2 | H | O | |
| 8-4 | 3,5-diCl | CF3 | F | 2-PyridylCH2 | H | O | |
| 8-5 | 3,5-diCl | CF3 | Cl | CF3CH2 | H | O | |
| 8-6 | 3,5-diCl | CF3 | Cl | 2-PyridylCH2 | H | O | |
| 8-7 | 3,5-diCl | CF3 | Br | CF3CH2 | H | O | |
| 8-8 | 3,5-diCl | CF3 | Br | 2-PyridylCH2 | H | O | |
| 8-9 | 3,5-diCl | CF3 | Br | cyclo-Pr | H | O | |
| 8-10 | 3,5-diCl | CF3 | Br | NCCH2CH2 | H | O | |
| 8-11 | 3,5-diCl | CF3 | I | CF3CH2 | H | O | |
| 8-12 | 3,5-diCl | CF3 | I | 2-PyridylCH2 | H | O | |
| 8-13 | 3,5-diCl | CF3 | NO2 | CF3CH2 | H | O | |
| 8-14 | 3,5-diCl | CF3 | NO2 | 2-PyridylCH2 | H | O | |
| 8-15 | 3-Cl | CF3 | NO2 | 2-PyridylCH2 | H | O | |
| 8-16 | 3-Cl | CF3 | NO2 | CF3CH2 | H | O | |

TABLE 8-continued

|      | (X)m         | R   | Y              | R1             | R2  | W | m.p. ° C. |
|------|--------------|-----|----------------|----------------|-----|---|-----------|
| 8-17 | 3-Br         | CF3 | NO2            | 2-PyridylCH2   | H   | O |           |
| 8-18 | 3-CF3        | CF3 | NO2            | 2-PyridylCH2   | H   | O |           |
| 8-19 | 3-CF3        | CF3 | NO2            | CF3CH2         | H   | O |           |
| 8-20 | 3,5-diCF3    | CF3 | NO2            | 2-PyridylCH2   | H   | O |           |
| 8-21 | 3,5-diCF3    | CF3 | NO2            | CF3CH2         | H   | O |           |
| 8-22 | 3-NO2        | CF3 | NO2            | 2-PyridylCH2   | H   | O |           |
| 8-23 | 3,5-diCl     | CF3 | CF3            | 2-PyridylCH2   | H   | O |           |
| 8-24 | 3,5-diCl     | CF3 | CF3            | CF3CH2         | H   | O |           |
| 8-25 | 3,5-diCl     | CF3 | CF3            | H              | H   | O |           |
| 8-26 | 3,5-diCl     | CF3 | CH3O           | 2-PyridylCH2   | H   | O |           |
| 8-27 | 3,5-diCl     | CF3 | CN             | 2-PyridylCH2   | H   | O |           |
| 8-28 | 3,5-diCl     | CF3 | CF3O           | 2-PyridylCH2   | H   | O |           |
| 8-29 | 3,5-diCl     | CF3 | CH3S           | 2-PyridylCH2   | H   | O |           |
| 8-30 | 3,5-diCl     | CF3 | CH3S(O)        | 2-PyridylCH2   | H   | O |           |
| 8-31 | 3,5-diCl     | CF3 | CH3S(O)2       | 2-PyridylCH2   | H   | O |           |
| 8-32 | 3,5-diCl     | CF3 | CF3S           | 2-PyridylCH2   | H   | O |           |
| 8-33 | 3,5-diCl     | CF3 | CF3S(O)        | 2-PyridylCH2   | H   | O |           |
| 8-34 | 3,5-diCl     | CF3 | CF3S(O)2       | 2-PyridylCH2   | H   | O |           |
| 8-35 | 3,5-diCl     | CF3 | OH             | 2-PyridylCH2   | H   | O |           |
| 8-36 | 3,5-diCl     | CF3 | SH             | 2-PyridylCH2   | H   | O |           |
| 8-37 | 3,5-diCl     | CF3 | NH2            | 2-PyridylCH2   | H   | O |           |
| 8-38 | 3,5-diCl     | CF3 | NHCOCH3        | 2-PyridylCH2   | H   | O |           |
| 8-39 | 3,5-diCl     | CF3 | NHCOCF3        | 2-PyridylCH2   | H   | O |           |
| 8-40 | 3,5-diCl     | CF3 | NHCO2CH3       | 2-PyridylCH2   | H   | O |           |
| 8-41 | 3,5-diCl     | CF3 | NHCO2CH2CCl3   | 2-PyridylCH2   | H   | O |           |
| 8-42 | 3-CH3        | CF3 | H              | 2-PyridylCH2   | H   | O |           |
| 8-43 | 3-CH3O       | CF3 | H              | 2-PyridylCH2   | H   | O |           |
| 8-44 | 3-CN         | CF3 | H              | 2-PyridylCH2   | H   | O |           |
| 8-45 | 3-CF3O       | CF3 | H              | 2-PyridylCH2   | H   | O |           |
| 8-46 | 3-CH3S       | CF3 | H              | 2-PyridylCH2   | H   | O |           |
| 8-47 | 3-CH3S(O)    | CF3 | H              | 2-PyridylCH2   | H   | O |           |
| 8-48 | 3-CH3S(O)2   | CF3 | H              | 2-PyridylCH2   | H   | O |           |
| 8-49 | 3-CF3S       | CF3 | H              | 2-PyridylCH2   | H   | O |           |
| 8-50 | 3-CF3S(O)    | CF3 | H              | 2-PyridylCH2   | H   | O |           |
| 8-51 | 3-CF3S(O)2   | CF3 | H              | 2-PyridylCH2   | H   | O |           |
| 8-52 | 3-OH         | CF3 | H              | 2-PyridylCH2   | H   | O |           |
| 8-53 | 3-SH         | CF3 | H              | 2-PyridylCH2   | H   | O |           |
| 8-54 | 3,4-diCl     | CF3 | H              | 2-PridylCH2    | H   | O |           |
| 8-55 | 3,4-diCl     | CF3 | H              | CF3CH2         | H   | O |           |
| 8-56 | 3,4,5-triCl  | CF3 | H              | 2-PyridylCH2   | H   | O |           |
| 8-57 | 3,4,5-triCl  | CF3 | H              | CF3CH2         | H   | O |           |
| 8-58 | 3,5-diBr     | CF3 | H              | 2-PyridylCH2   | H   | O |           |
| 8-59 | 3,5-diBr     | CF3 | H              | CF3CH2         | H   | O |           |
| 8-60 | 3,5-diMe-4-NO2 | CF3 | H            | 2-PyridylCH2   | H   | O |           |
| 8-61 | 3,5-diMe-4-NO2 | CF3 | H            | CF3CH2         | H   | O |           |
| 8-62 | 3,5-diCl     | CF3 | H              | 2-PyridylCH2   | H   | S |           |
| 8-63 | 3,5-diCl     | CF3 | NO2            | H              | H   | O |           |
| 8-64 | 3,5-diCl     | CF3 | NO2            | Me             | H   | O |           |
| 8-65 | 3,5-diCl     | CF3 | NO2            | iso-Pr         | H   | O |           |
| 8-66 | 3,5-diCl     | CF3 | NO2            | PhCH2          | H   | O |           |
| 8-67 | 3,5-diCl     | CF3 | NO2            | CH2CO2CH3      | H   | O |           |
| 8-68 | 3,5-diCl     | CF3 | NO2            | CH2CONMe       | H   | O |           |
| 8-69 | 3,5-diCl     | CF3 | NO2            | CH2(cyclo)Pr   | H   | O |           |
| 8-70 | 3,5-diCl     | CF3 | NO2            | SO2Me          | H   | O |           |
| 8-71 | 3,5-diCl     | CF3 | NO2            | SO2CF3         | H   | O |           |
| 8-72 | 3,5-diCl     | CF3 | NO2            | CH2=CHCH2      | H   | O |           |
| 8-73 | 3,5-diCl     | CF3 | NO2            | HCCCH2         | H   | O |           |
| 8-74 | 3,5-diCl     | CF3 | NO2            | CH2CN          | H   | O |           |
| 8-75 | 3,5-diCl     | CF3 | NO2            | C(Me)2CH2SCH3  | H   | O |           |
| 8-76 | 3,5-diCl     | CF3 | NO2            | 2-F—Ph         | H   | O |           |
| 8-77 | 3,5-diCl     | CH3 | H              | 2-PyridylCH2   | H   | O |           |
| 8-78 | 3,5-diCl     | CF3 | H              | 2-PyridylCH2   | CH3 | O |           |
| 8-79 | 3-NO2        | CF3 | NO2            | CF3CH2         | H   | O |           |
| 8-80 | 3,5-diCl     | CF3 | Cl             | 2-PyridylCH2   | H   | S |           |
| 8-81 | 2-diCl       | CF3 | NO2            | 2-PyridylCH2   | H   | O |           |
| 8-82 | 2,3-diCl     | CF3 | NO2            | 2-PyridylCH2   | H   | O |           |
| 8-83 | 3,5-diCl     | CF3 | NO2            | 3-PyridylCH2   | H   | O |           |

TABLE 8-continued

| | (X)m | R | Y | R1 | R2 | W | m.p. ° C.) |
|---|---|---|---|---|---|---|---|
| 8-84 | 3,5-diCl | CF3 | NO2 | 4-PyridylCH2 | H | O | |
| 8-85 | 3,5-diCl | CF3 | NO2 | 2-(6-Cl-pyridyl)CH2 | H | O | |
| 8-86 | 3,5-diCl | CF3 | NO2 | 3-(6-Cl-pyridyl)CH2 | H | O | |
| 8-87 | 3,5-diCl | CF3 | NO2 | 2-PyrinidinylCH2 | H | O | |
| 8-88 | 3,5-diCl | CF3 | NO2 | 1-(1-ethylpyrrolidin-2-yl)CH2 | H | O | |
| 8-89 | 3,5-diCl | CF3 | CF3 | CF3CH2 | H | O | |
| 8-90 | 3,5-diCl | CF3 | CF3 | 2-(6-Cl-pyridyl)CH2 | H | O | |
| 8-91 | 3,5-diCl | CF3 | NO2 | Me2NCH= | | O | |
| 8-92 | 3,5-diCl | CF3 | NO2 | EtON=CH | | O | |
| 8-93 | 3,5-diCl | CF3 | C=NOCH3 | 2-PyridylCH2 | H | O | |
| 8-94 | 4-Cl | CF3 | NO2 | 2-PyridylCH2 | H | O | |
| 8-95 | 4-Cl | CF3 | NO2 | CF3CH2 | H | O | |
| 8-96 | 3,5-diCl | CF3 | CN | CF3CH2 | H | O | |
| 8-97 | 3,5-diCl | CF3 | CF3 | H | H | O | |
| 8-98 | 3,5-diCF3 | CF3 | CF3 | 2-PyridylCH2 | H | O | |
| 8-99 | 3,5-diCF3 | CF3 | CF3 | CF3CH2 | H | O | |

TABLE 9

| | (X)m | R | Y | R2 | R3 | R4 | R5 | l | m.p. ° C.) |
|---|---|---|---|---|---|---|---|---|---|
| 9-1 | 3,5-diCl | CF3 | H | H | H | H | COCH3 | 1 | |
| 9-2 | 3,5-diCl | CF3 | H | H | H | H | COC2H5 | 1 | |
| 9-3 | 3,5-diCl | CF3 | Cl | H | H | H | COCH3 | 1 | |
| 9-4 | 3,5-diCl | CF3 | Br | H | H | H | COCH3 | 1 | |
| 9-5 | 3,5-diCl | CF3 | Br | H | H | H | COC2H5 | 1 | |
| 9-6 | 3,5-diCl | CF3 | Br | H | H | H | CO(i-Pr) | 1 | |
| 9-7 | 3,5-diCl | CF3 | Br | H | H | H | CO2-pyridyl | 1 | |
| 9-8 | 3,5-diCl | CF3 | F | H | H | H | COCH3 | 1 | |
| 9-9 | 3,5-diCl | CF3 | I | H | H | H | COCH3 | 1 | |
| 9-10 | 3,5-diCl | CF3 | NO2 | H | H | H | COCH3 | 1 | |
| 9-11 | 3,5-diCl | CF3 | CH3 | H | H | H | COCH3 | 1 | |
| 9-12 | 3,5-diCl | CF3 | MeS | H | H | H | COCH3 | 1 | |
| 9-13 | 3,5-diCl | CF3 | MeSO | H | H | H | COCH3 | 1 | |
| 9-14 | 3,5-diCl | CF3 | MeSO2 | H | H | H | COCH3 | 1 | |
| 9-15 | 3,5-diCl | CF3 | CF3S | H | H | H | COCH3 | 1 | |
| 9-16 | 3,5-diCl | CF3 | CF3S(O) | H | H | H | COCH3 | 1 | |
| 9-17 | 3,5-diCl | CF3 | CF3S(O)2 | H | H | H | COCH3 | 1 | |
| 9-18 | 3,5-diCl | CF3 | OCH3 | H | H | H | COCH3 | 1 | |
| 9-19 | 3,5-diCl | CF3 | OCF3 | H | H | H | COCH3 | 1 | |
| 9-20 | 3,5-diCl | CF3 | OH | H | H | H | COCH3 | 1 | |
| 9-21 | 3,5-diCl | CF3 | SH | H | H | H | COCH3 | 1 | |
| 9-22 | 3,5-diCl | CF3 | NH2 | H | H | H | COCH3 | 1 | |
| 9-23 | 3,5-diCl | CF3 | NHCOCH3 | H | H | H | COCH3 | 1 | |
| 9-24 | 3,5-diCl | CF3 | NHCO2CH3 | H | H | H | COCH3 | 1 | |
| 9-25 | 3,5-diCl | CF3 | NHCO2CH2CCl3 | H | H | H | COCH3 | 1 | |
| 9-26 | 3,5-diCl | CF3 | Cl | H | H | Me | CO2-pyridyl | 1 | |
| 9-27 | 3,5-diCl | CF3 | Cl | H | H | Me | COCH3 | 1 | |
| 9-28 | 3,5-diCl | CF3 | Cl | H | H | Et | COCH3 | 1 | |
| 9-29 | 3,5-diCl | CF3 | Cl | H | H | vinyl | COCH3 | 1 | |
| 9-30 | 3,5-diCl | CF3 | Cl | H | H | propargyl | COCH3 | 1 | |
| 9-31 | 3,5-diCl | CF3 | Cl | H | H | CH2Ph | COCH3 | 1 | |
| 9-32 | 3,5-diCl | CF3 | Cl | H | H | CN | COCH3 | 1 | |
| 9-33 | 3,5-diCl | CF3 | Cl | H | H | CH2CF3 | COCH3 | 1 | |

TABLE 9-continued

|  | (X)m | R | Y | R2 | R3 | R4 | R5 | l | m.p. ° C.) |
|---|---|---|---|---|---|---|---|---|---|
| 9-34 | 3,5-diCl | CF3 | Cl | H | H | cycloPr | COCH3 | 1 | |
| 9-35 | 3,5-diCl | CF3 | Cl | H | H | COCH3 | COCH3 | 1 | |
| 9-36 | 3,5-diCl | CF3 | Cl | H | H | H | COC2H5 | 1 | |
| 9-37 | 3,5-diCl | CF3 | Cl | H | H | H | COC2F5 | 1 | |
| 9-38 | 3,5-diCl | CF3 | Cl | H | H | H | COPh | 1 | |
| 9-39 | 3,5-diCl | CF3 | Cl | H | H | H | CO2-pyridyl | 1 | |
| 9-40 | 3,5-diCl | CF3 | Cl | H | H | H | CONMe2 | 1 | |
| 9-41 | 3,5-diCl | CF3 | Cl | H | H | H | CO2Me | 1 | |
| 9-42 | 3,5-diCl | CF3 | Cl | H | H | H | COSMe | 1 | |
| 9-43 | 3,5-diCl | CF3 | Cl | H | H | Me | COCH3 | 1 | |
| 9-44 | 3,5-diCl | CF3 | Cl | H | H | 2-pyridylCO | COCH3 | 1 | |
| 9-45 | 3,5-diBr | CF3 | Cl | H | H | H | COCH3 | 1 | |
| 9-46 | 3-Cl | CF3 | Cl | H | H | H | COCH3 | 1 | |
| 9-47 | 3-CF3 | CF3 | Cl | H | H | H | COCH3 | 1 | |
| 9-48 | 3,5-diCF3 | CF3 | Cl | H | H | H | COCH3 | 1 | |
| 9-49 | 3,4,5-triCl | CF3 | Cl | H | H | H | COCH3 | 1 | |
| 9-50 | 3,5-diMe-4-NO2 | CF3 | Cl | H | H | H | COCH3 | 1 | |
| 9-51 | 3-NO2 | CF3 | Cl | H | H | H | COCH3 | 1 | |
| 9-52 | 3-CH3 | CF3 | Cl | H | H | H | COCH3 | 1 | |
| 9-53 | 3-CH3O | CF3 | Cl | H | H | H | COCH3 | 1 | |
| 9-54 | 3-CN | CF3 | Cl | H | H | H | COCH3 | 1 | |
| 9-55 | 3-CF3O | CF3 | Cl | H | H | H | COCH3 | 1 | |
| 9-56 | 3-CH3S | CF3 | Cl | H | H | H | COCH3 | 1 | |
| 9-57 | 3-CH3S(O) | CF3 | Cl | H | H | H | COCH3 | 1 | |
| 9-58 | 3-CH3S(O)2 | CF3 | Cl | H | H | H | COCH3 | 1 | |
| 9-59 | 3-CF3S | CF3 | Cl | H | H | H | COCH3 | 1 | |
| 9-60 | 3-CF3S(O) | CF3 | Cl | H | H | H | COCH3 | 1 | |
| 9-61 | 3-CF3S(O)2 | CF3 | Cl | H | H | H | COCH3 | 1 | |
| 9-62 | 3-OH | CF3 | Cl | H | H | H | COCH3 | 1 | |
| 9-63 | 3-SH | CF3 | Cl | H | H | H | COCH3 | 1 | |
| 9-64 | 3,5-diCl | CF3 | Cl | CN | H | H | COCH3 | 1 | |
| 9-65 | 3,5-diCl | CF3 | Cl | Me | H | H | COCH3 | 1 | |
| 9-66 | 3,5-diCl | CF3 | Cl | Me | Me | H | COCH3 | 1 | |
| 9-67 | 3,5-diCl | CF3 | Cl | cyclo-Pr | H | H | COCH3 | 1 | |
| 9-68 | 3,5-diCl | CF3 | Cl | CF3 | H | H | COCH3 | 1 | |
| 9-69 | 3,5-diCl | CF3 | Cl | CO2Me | H | H | COCH3 | 1 | |
| 9-70 | 3,5-diCl | CF3 | Cl | CH=CH2 | H | H | COCH3 | 1 | |
| 9-71 | 3,5-diCl | CF3 | Cl | CH2CH2 | H | H | COCH3 | 1 | |
| 9-72 | 3,5-diCl | CF3 | Cl | CCH | H | H | COCH3 | 1 | |
| 9-73 | 3,5-diCl | CF3 | Br | H | H | H | COEt | 1 | |
| 9-74 | 3,5-diCl | CF3 | Br | H | H | H | COPr-n | 1 | |
| 9-75 | 3,5-diCl | CF3 | Br | H | H | H | COPr-iso | 1 | |
| 9-76 | 3,5-diCl | CF3 | Br | H | H | H | COBu-tert | 1 | |
| 9-77 | 3,5-diCl | CF3 | Br | H | H | H | COCF3 | 1 | |
| 9-78 | 3,5-diCl | CF3 | Br | H | H | H | COPh | 1 | |
| 9-79 | 3,5-diCl | CF3 | Br | H | H | H | COpyridyl-2 | 1 | |
| 9-80 | 3,5-diCl | CF3 | Br | H | H | H | COpyridyl-3 | 1 | |
| 9-81 | 3,5-diCl | CF3 | Br | H | H | H | COpyridylCO-4 | 1 | |
| 9-82 | 3,5-diCl | CF3 | Br | H | H | H | COPh—F-2 | 1 | |
| 9-83 | 3,5-diCl | CF3 | Br | H | H | H | COPh—F-3 | 1 | |
| 9-84 | 3,5-diCl | CF3 | Br | H | H | H | COPh—F-4 | 1 | |
| 9-85 | 3,5-diCl | CF3 | Br | H | H | H | COPh—Cl-2 | 1 | |
| 9-86 | 3,5-diCl | CF3 | Br | H | H | H | COPh—Cl-3 | 1 | |
| 9-87 | 3,5-diCl | CF3 | Br | H | H | H | COPh—Cl-4 | 1 | |
| 9-88 | 3,5-diCl | CF3 | Br | H | H | H | COPh—Br-2 | 1 | |
| 9-89 | 3,5-diCl | CF3 | Br | H | H | H | COPh—Me-2 | 1 | |
| 9-90 | 3,5-diCl | CF3 | Br | H | H | H | COvinyl | 1 | |
| 9-91 | 3,5-diCl | CF3 | Br | H | H | H | COpropargyl | 1 | |
| 9-92 | 3,5-diCl | CF3 | Br | H | H | H | MeSO2 | 1 | |
| 9-93 | 3,5-diCl | CF3 | Br | H | H | H | CF3SO2 | 1 | |
| 9-94 | 3,5-diCl | CF3 | Br | H | H | H | CONHMe | 1 | |
| 9-95 | 3,5-diCl | CF3 | Br | H | H | H | CONMe2 | 1 | |
| 9-96 | 3,5-diCl | CF3 | Br | H | H | H | CO2Me | 1 | |
| 9-97 | 3,5-diCl | CF3 | Br | H | H | H | C(O)SMe | 1 | |
| 9-98 | 3,5-diCl | CF3 | Br | H | H | H | CSMe | 1 | |
| 9-99 | 3,5-diCl | CF3 | Br | H | H | H | CON(Me)OMe | 1 | |
| 9-100 | 3,5-diCl | CH3 | Br | H | H | H | COCH3 | 1 | |
| 9-101 | 3,5-diCl | CH3 | CF3 | H | H | H | COCH3 | 1 | |

TABLE 9-continued

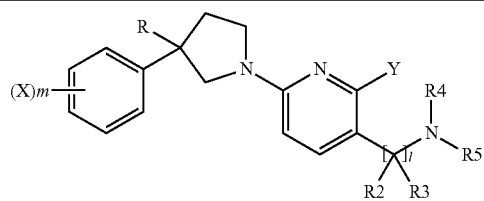

|  | (X)m | R | Y | R2 | R3 | R4 | R5 | l | m.p. ° C.) |
|---|---|---|---|---|---|---|---|---|---|
| 9-102 | 3,5-diCl | CH3 | CN | H | H | H | COCH3 | 1 | |
| 9-103 | 3,5-diCl | CH3 | NH2 | H | H | H | COCH3 | 1 | |
| 9-104 | 3,5-diCl | CH3 | NHCOCH3 | H | H | H | COCH3 | 1 | |
| 9-105 | 3,5-diCl | CH3 | NHCOCF3 | H | H | H | COCH3 | 1 | |
| 9-106 | 3,5-diCl | CH3 | NHCO2CH3 | H | H | H | COCH3 | 1 | |
| 9-107 | 3,5-diCl | CH3 | NHCO2CH2CCl3 | H | H | H | COCH3 | 1 | |
| 9-108 | 3,5-diCl | CH3 | NHSO2CH3 | H | H | H | COCH3 | 1 | |
| 9-109 | 3,5-diCl | CH3 | NHSO2CF3 | H | H | H | COCH3 | 1 | |
| 9-110 | 3,5-diCl | CH3 | C=NOCH3 | H | H | H | COCH3 | 1 | |
| 9-111 | 3,5-diCl | CF3 | Br | H | H | H | COCH3 | 2 | |
| 9-112 | 3,5-diCF3 | CF3 | CF3 | H | H | H | COCH3 | 1 | |
| 9-113 | 3,5-diCF3 | CF3 | CF3 | H | H | H | COC2H5 | 1 | |
| 9-114 | 3,5-diCF3 | CF3 | CF3 | H | H | H | COPr-cyclo | 1 | |
| 9-115 | 3,4,5-triCl | CF3 | CF3 | H | H | H | COCH3 | 1 | |
| 9-116 | 3,4,5-triCl | CF3 | CF3 | H | H | H | COC2H5 | 1 | |
| 9-117 | 3,4,5-triCl | CF3 | CF3 | H | H | H | COPr-cyclo | 1 | |
| 9-118 | 3,4-diCl, 5-CF3 | CF3 | CF3 | H | H | H | COCH3 | 1 | |

TABLE 10

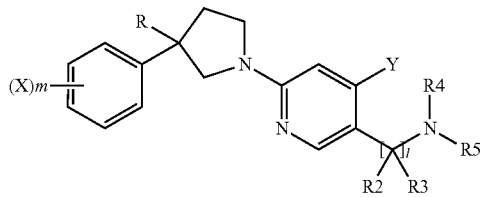

|  | (X)m | R | Y | R2 | R3 | R4 | R5 | l | m.p. ° C.) |
|---|---|---|---|---|---|---|---|---|---|
| 10-1 | 3,5-diCl | CF3 | Cl | H | H | H | COCH3 | 1 | |
| 10-2 | 3,5-diCl | CF3 | Br | H | H | H | COCH3 | 1 | |
| 10-3 | 3,5-diCl | CF3 | Br | H | H | H | COC2H5 | 1 | |
| 10-4 | 3,5-diCl | CF3 | Br | H | H | H | CO(i-Pr) | 1 | |
| 10-5 | 3,5-diCl | CF3 | Br | H | H | H | CO2-pyridyl | 1 | |
| 10-6 | 3,5-diCl | CF3 | F | H | H | H | COCH3 | 1 | |
| 10-7 | 3,5-diCl | CF3 | I | H | H | H | COCH3 | 1 | |
| 10-8 | 3,5-diCl | CF3 | NO2 | H | H | H | COCH3 | 1 | |
| 10-9 | 3,5-diCl | CF3 | CH3 | H | H | H | COCH3 | 1 | |
| 10-10 | 3,5-diCl | CF3 | MeS | H | H | H | COCH3 | 1 | |
| 10-11 | 3,5-diCl | CF3 | MeSO | H | H | H | COCH3 | 1 | |
| 10-12 | 3,5-diCl | CF3 | MeSO2 | H | H | H | COCH3 | 1 | |
| 10-13 | 3,5-diCl | CF3 | CF3S | H | H | H | COCH3 | 1 | |
| 10-14 | 3,5-diCl | CF3 | CF3S(O) | H | H | H | COCH3 | 1 | |
| 10-15 | 3,5-diCl | CF3 | CF3S(O)2 | H | H | Ii | COCH3 | 1 | |
| 10-16 | 3,5-diCl | CF3 | OCH3 | H | H | H | COCH3 | 1 | |
| 10-17 | 3,5-diCl | CF3 | OCF3 | H | H | H | COCH3 | 1 | |
| 10-18 | 3,5-diCl | CF3 | OH | H | H | H | COCH3 | 1 | |
| 10-19 | 3,5-diCl | CF3 | SH | H | H | H | COCH3 | 1 | |
| 10-20 | 3,5-diCl | CF3 | NH2 | H | H | H | COCH3 | 1 | |
| 10-21 | 3,5-diCl | CF3 | NHCOCH3 | H | H | H | COCH3 | 1 | |
| 10-22 | 3,5-diCl | CF3 | NHCO2CH3 | H | H | H | COCH3 | 1 | |
| 10-23 | 3,5-diCl | CF3 | NHCO2CH2CCl3 | H | H | H | COCH3 | 1 | |
| 10-24 | 3,5-diCl | CF3 | Cl | H | H | Me | CO2-pyridyl | 1 | |
| 10-25 | 3,5-diCl | CF3 | Cl | H | H | Me | COCH3 | 1 | |
| 10-26 | 3,5-diCl | CF3 | Cl | H | H | Et | COCH3 | 1 | |
| 10-27 | 3,5-diCl | CF3 | Cl | H | H | vinyl | COCH3 | 1 | |
| 10-28 | 3,5-diCl | CF3 | Cl | H | H | propargyl | COCH3 | 1 | |
| 10-29 | 3,5-diCl | CF3 | Cl | H | H | CH2Ph | COCH3 | 1 | |
| 10-30 | 3,5-diCl | CF3 | Cl | H | H | CN | COCH3 | 1 | |
| 10-31 | 3,5-diCl | CF3 | Cl | H | H | CH2CF3 | COCH3 | 1 | |
| 10-32 | 3,5-diCl | CF3 | Cl | H | H | cycloPr | COCH3 | 1 | |
| 10-33 | 3,5-diCl | CF3 | Cl | H | H | COCH3 | COCH3 | 1 | |

TABLE 10-continued

| | (X)m | R | Y | R2 | R3 | R4 | R5 | l | m.p. ° C.) |
|---|---|---|---|---|---|---|---|---|---|
| 10-34 | 3,5-diCl | CF3 | Cl | H | H | H | COC2H5 | 1 | |
| 10-35 | 3,5-diCl | CF3 | Cl | H | H | H | COC2F5 | 1 | |
| 10-36 | 3,5-diCl | CF3 | Cl | H | H | H | COPh | 1 | |
| 10-37 | 3,5-diCl | CF3 | Cl | H | H | H | CO2-Pyridyl | 1 | |
| 10-38 | 3,5-diCl | CF3 | Cl | H | H | H | CONMe2 | 1 | |
| 10-39 | 3,5-diCl | CF3 | Cl | H | H | H | CO2Me | 1 | |
| 10-40 | 3,5-diCl | CF3 | Cl | H | H | H | COSMe | 1 | |
| 10-41 | 3,5-diCl | CF3 | Cl | H | H | Me | COCH3 | 1 | |
| 10-42 | 3,5-diCl | CF3 | Cl | H | H | 2-pyridylCO | COCH3 | 1 | |
| 10-43 | 3,5-diBr | CF3 | Cl | H | H | H | COCH3 | 1 | |
| 10-44 | 3-Cl | CF3 | Cl | H | H | H | COCH3 | 1 | |
| 10-45 | 3-CF3 | CF3 | Cl | H | H | H | COCH3 | 1 | |
| 10-46 | 3,5-diCF3 | CF3 | Cl | H | H | H | COCH3 | 1 | |
| 10-47 | 3,4,5-triCl | CF3 | Cl | H | H | H | COCH3 | 1 | |
| 10-48 | 3,5-diMe-4-NO2 | CF3 | Cl | H | H | H | COCH3 | 1 | |
| 10-49 | 3-NO2 | CF3 | Cl | H | H | H | COCH3 | 1 | |
| 10-50 | 3-CH3 | CF3 | Cl | H | H | H | COCH3 | 1 | |
| 10-51 | 3-CH3O | CF3 | Cl | H | H | H | COCH3 | 1 | |
| 10-52 | 3-CN | CF3 | Cl | H | H | H | COCH3 | 1 | |
| 10-53 | 3-CF3O | CF3 | Cl | H | H | H | COCH3 | 1 | |
| 10-54 | 3-CH3S | CF3 | Cl | H | H | H | COCH3 | 1 | |
| 10-55 | 3-CH3S(O) | CF3 | Cl | H | H | H | COCH3 | 1 | |
| 10-56 | 3-CH3S(O)2 | CF3 | Cl | H | H | H | COCH3 | 1 | |
| 10-57 | 3-CF3S | CF3 | Cl | H | H | H | COCH3 | 1 | |
| 10-58 | 3-CF3S(O) | CF3 | Cl | H | H | H | COCH3 | 1 | |
| 10-58 | 3-CF3S(O)2 | CF3 | Cl | H | H | H | COCH3 | 1 | |
| 10-60 | 3-OH | CF3 | Cl | H | H | H | COCH3 | 1 | |
| 10-61 | 3-SH | CF3 | Cl | H | H | H | COCH3 | 1 | |
| 10-62 | 3,5-diCl | CF3 | Cl | CN | H | H | COCH3 | 1 | |
| 10-63 | 3,5-diCl | CF3 | Cl | Me | H | H | COCH3 | 1 | |
| 10-64 | 3,5-diCl | CF3 | Cl | Me | Me | H | COCH3 | 1 | |
| 10-65 | 3,5-diCl | CF3 | Cl | cyclo-Pr | H | H | COCH3 | 1 | |
| 10-66 | 3,5-diCl | CF3 | Cl | CF3 | H | H | COCH3 | 1 | |
| 10-67 | 3,5-diCl | CF3 | Cl | CO2Me | H | H | COCH3 | 1 | |
| 10-68 | 3,5-diCl | CF3 | Cl | CH=CH2 | H | H | COCH3 | 1 | |
| 10-69 | 3,5-diCl | CF3 | Cl | CH2CH2 | | H | COCH3 | 1 | |
| 10-70 | 3,5-diCl | CF3 | Cl | CCH | H | H | COCH3 | 1 | |
| 10-71 | 3,5-diCl | CF3 | Br | H | H | H | COEt | 1 | |
| 10-72 | 3,5-diCl | CF3 | Br | H | H | H | COPr-n | 1 | |
| 10-73 | 3,5-diCl | CF3 | Br | H | H | H | COPr-iso | 1 | |
| 10-74 | 3,5-diCl | CF3 | Br | H | H | H | COBu-tert | 1 | |
| 10-75 | 3,5-diCl | CF3 | Br | H | H | H | COCF3 | 1 | |
| 10-76 | 3,5-diCl | CF3 | Br | H | H | H | COPh | 1 | |
| 10-77 | 3,5-diCl | CF3 | Br | H | H | H | COpyridyl-2 | 1 | |
| 10-78 | 3,5-diCl | CF3 | Br | H | H | H | COpyridyl-3 | 1 | |
| 10-79 | 3,5-diCl | CF3 | Br | H | H | H | COpyridylCO-4 | 1 | |
| 10-80 | 3,5-diCl | CF3 | Br | H | H | H | COPh—F-2 | 1 | |
| 10-81 | 3,5-diCl | CF3 | Br | H | H | H | COPh—F-3 | 1 | |
| 10-82 | 3,5-diCl | CF3 | Br | H | H | H | COPh—F-4 | 1 | |
| 10-83 | 3,5-diCl | CF3 | Br | H | H | H | COPh—Cl-2 | 1 | |
| 10-84 | 3,5-diCl | CF3 | Br | H | H | H | COPh—Cl-3 | 1 | |
| 10-85 | 3,5-diCl | CF3 | Br | H | H | H | COPh—Cl-4 | 1 | |
| 10-86 | 3,5-diCl | CF3 | Br | H | H | H | COPh—Br-2 | 1 | |
| 10-87 | 3,5-diCl | CF3 | Br | H | H | H | COPh—Me-2 | 1 | |
| 10-88 | 3,5-diCl | CF3 | Br | H | H | H | Covinyl | 1 | |
| 10-89 | 3,5-diCl | CF3 | Br | H | H | H | COproparpyl | 1 | |
| 10-90 | 3,5-diCl | CF3 | Br | H | H | H | MeSO2 | 1 | |
| 10-91 | 3,5-diCl | CF3 | Br | H | H | H | CF3SO2 | 1 | |
| 10-92 | 3,5-diCl | CF3 | Br | H | H | H | CONHMe | 1 | |
| 10-93 | 3,5-diCl | CF3 | Br | H | H | H | CONMe2 | 1 | |
| 10-94 | 3,5-diCl | CF3 | Br | H | H | H | CO2Me | 1 | |
| 10-95 | 3,5-diCl | CF3 | Br | H | H | H | C(O)SMe | 1 | |
| 10-96 | 3,5-diCl | CF3 | Br | H | H | H | CSMe | 1 | |
| 10-97 | 3,5-diCl | CF3 | Br | H | H | H | CON(Me)OMe | 1 | |
| 10-98 | 3,5-diCl | CH3 | Br | H | H | H | COCH3 | 1 | |
| 10-99 | 3,5-diCl | CH3 | CF3 | H | H | H | COCH3 | 1 | |
| 10-100 | 3,5-diCl | CH3 | CN | H | H | H | COCH3 | 1 | |
| 10-101 | 3,5-diCl | CH3 | NH2 | H | H | H | COCH3 | 1 | |

TABLE 10-continued

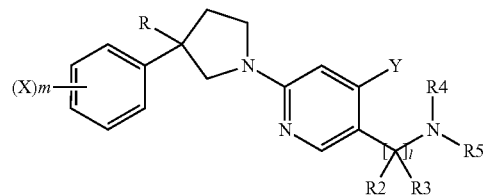

| | (X)m | R | Y | R2 | R3 | R4 | R5 | l | m.p. ° C.) |
|---|---|---|---|---|---|---|---|---|---|
| 10-102 | 3,5-diCl | CH3 | NHCOCH3 | H | H | H | COCH3 | 1 | |
| 10-103 | 3,5-diCl | CH3 | NHCOCF3 | H | H | H | COCH3 | 1 | |
| 10-104 | 3,5-diCl | CH3 | NHCO2CH3 | H | H | H | COCH3 | 1 | |
| 10-105 | 3,5-diCl | CH3 | NHCO2CH2CCl3 | H | H | H | COCH3 | 1 | |
| 10-106 | 3,5-diCl | CH3 | NHSO2CH3 | H | H | H | COCH3 | 1 | |
| 10-107 | 3,5-diCl | CH3 | NHSO2CF3 | H | H | H | COCH3 | 1 | |
| 10-108 | 3,5-diCl | CH3 | C=NOCH3 | H | H | H | COCH3 | 1 | |
| 10-109 | 3,5-diCl | CF3 | Br | H | H | H | COCH3 | 2 | |
| 10-110 | 3,5-diCF3 | CF3 | CF3 | H | H | H | COCH3 | 1 | |
| 10-111 | 3,5-diCF3 | CF3 | CF3 | H | H | H | COC2H5 | 1 | |
| 10-112 | 3,5-diCF3 | CF3 | CF3 | H | H | H | COPr-cyclo | 1 | |
| 10-113 | 3,4,5-triCl | CF3 | CF3 | H | H | H | COCH3 | 1 | |
| 10-114 | 3,4,5-triCl | CF3 | CF3 | H | H | H | COC2H5 | 1 | |
| 10-115 | 3,4,5-triCl | CF3 | CF3 | H | H | H | COPr-cyclo | 1 | |
| 10-116 | 3,4,-diCl, 5-CF3 | CF3 | CF3 | H | H | H | COCH3 | 1 | |

TABLE 11

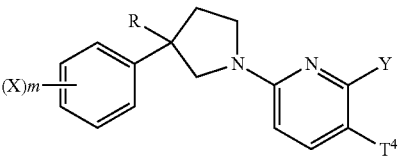

| | (X)m | R | Y | T⁴ | m.p. ° C.) |
|---|---|---|---|---|---|
| 11-1 | 3,5-diCl | CF3 | NO2 | CO2Me | |
| 11-2 | 3,5-diCl | CF3 | NO2 | CO2H | |
| 11-3 | 3,5-diCl | CF3 | NH2 | CO2Me | |
| 11-4 | 3,5-diCl | CF3 | F | CO2Me | |
| 11-5 | 3,5-diCl | CF3 | Cl | CO2Me | |
| 11-6 | 3,5-diCl | CF3 | Cl | CO2Bu-t | |
| 11-7 | 3,5-diCl | CF3 | Cl | CO2H | |
| 11-8 | 3,5-diCl | CF3 | Br | CO2Me | |
| 11-9 | 3,5-diCl | CF3 | I | CO2Me | |
| 11-10 | 3,5-diCl | CF3 | CH3 | CO2Me | |
| 11-11 | 3,5-diCl | CF3 | Cl | CH3 | |
| 11-12 | 3,5-diCl | CF3 | CN | F | |
| 11-13 | 3,5-diCl | CF3 | CH3 | NO2 | |
| 11-14 | 3,5-diCl | CF3 | CH3 | NH2 | |
| 11-13 | 3,5-diCl | CF3 | Br | NO2 | |
| 11-16 | 3,5-diCl | CF3 | Br | NH2 | |
| 11-17 | 3-CF3 | CF3 | NO2 | CO2Me | |
| 11-18 | 3-CF3 | CF3 | NO2 | CO2H | |
| 11-19 | 3,5-diCF3 | CF3 | NO2 | CO2Me | |
| 11-20 | 3,5-diCF3 | CF3 | NO2 | CO2H | |
| 11-21 | 3,4-diCl | CF3 | NO2 | CO2Me | |
| 11-22 | 3,4-diCl | CF3 | NO2 | CO2H | |
| 11-23 | 3-Cl | CF3 | NO2 | CO2Me | |
| 11-24 | 3-Cl | CF3 | NO2 | CO2H | |
| 11-25 | 2,5-diBr | CF3 | NO2 | CO2Me | |
| 11-26 | 3,4,5-triCl | CF3 | NO2 | CO2Me | |
| 11-27 | 3,5-diMe-4-NO2 | CF3 | NO2 | CO2Me | |
| 11-28 | 3-NO2 | CF3 | NO2 | CO2Me | |
| 11-29 | 3-CH3 | CF3 | NO2 | CO2Me | |
| 11-30 | 3-CH3O | CF3 | NO2 | CO2Me | |
| 11-31 | 3-CN | CF3 | NO2 | CO2Me | |
| 11-32 | 3-CF3O | CF3 | NO2 | CO2Me | |
| 11-33 | 3-CH3S | CF3 | NO2 | CO2Me | |
| 11-34 | 3-CH3S(O) | CF3 | NO2 | CO2Me | |
| 11-35 | 3-CH3S(O)2 | CF3 | NO2 | CO2Me | |
| 11-36 | 3-CF3S | CF3 | NO2 | CO2Me | |
| 11-37 | 3-CF3S(O) | CF3 | NO2 | CO2Me | |

TABLE 11-continued

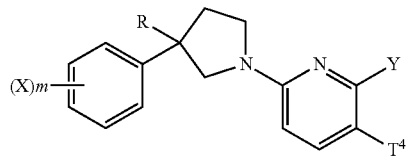

| | (X)m | R | Y | T⁴ | m.p. ° C.) |
|---|---|---|---|---|---|
| 11-38 | 3-CF3S(O)2 | CF3 | NO2 | CO2Me | |
| 11-39 | 3-OH | CF3 | NO2 | CO2Me | |
| 11-40 | 3-SH | CF3 | NO2 | CO2Me | |
| 11-41 | 3-NO2 | CF3 | NO2 | CO2H | |
| 11-42 | 3,4,5-triCl | CF3 | NO2 | CO2H | |
| 11-43 | 2-Cl | CF3 | NO2 | CO2Me | |
| 11-44 | 2-Cl | CF3 | NO2 | CO2H | |
| 11-45 | 4-Cl | CF3 | NO2 | CO2Me | |
| 11-46 | 4-Cl | CF3 | NO2 | CO2H | |
| 11-47 | 3,5-diCl | CF3 | CF3 | CO2Et | |
| 11-48 | 3,5-diCl | CF3 | CF3 | CO2H | |
| 11-49 | 3,5-diMe-4-NO2 | CF3 | NO2 | CO2H | |
| 11-50 | 3,4,5-triCl | CF3 | NO2 | CO2Me | |
| 11-51 | 3,5-diCl | CF3 | CN | CO2H | |
| 11-52 | 3,5-diCl | CF3 | CN | CO2Me | |
| 11-53 | 3,5-diCF3 | CF3 | CF3 | CO2Et | |
| 11-54 | 3,5-diCl | CF3 | CF3 | F | |
| 11-55 | 3,5-diCl | CF3 | CF3 | NO2 | |
| 11-56 | 3,5-diCl | CF3 | CF3 | NH2 | |
| 11-57 | 3,5-diCl | CF3 | F | CO2Et | |
| 11-58 | 3,4,5-triCl | CF3 | CF3 | CO2Et | |
| 11-59 | 3,4,5-triCl | CF3 | CF3 | CO2H | |

TABLE 12

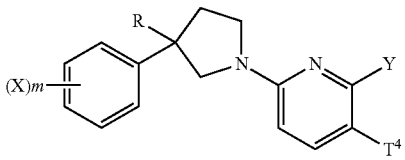

| | (X)m | R | Y | T⁴ | m.p. ° C. |
|---|---|---|---|---|---|
| 12-1 | 3,5-diCl | CF3 | H | NO2 | |
| 12-2 | 3,5-diCl | CF3 | H | CN | |
| 12-3 | 3,5-diCl | CF3 | H | NH2 | |
| 12-4 | 3,5-diCl | CF3 | H | CO2Me | |
| 12-5 | 3,5-diCl | CF3 | H | CO2H | |
| 12-6 | 3,5-diCl | CF3 | NO2 | CO2Me | |
| 12-7 | 3,5-diCl | CF3 | NO2 | CO2H | |
| 12-8 | 3,5-diCl | CF3 | NH2 | CO2Me | |
| 12-9 | 3,5-diCl | CF3 | F | CO2Me | |
| 12-10 | 3,5-diCl | CF3 | Cl | CO2Me | |
| 12-11 | 3,5-diCl | CF3 | Cl | CO2Bu-t | |
| 12-12 | 3,5-diCl | CF3 | Cl | CO2H | |
| 12-13 | 3,5-diCl | CF3 | Br | CO2Me | |
| 12-14 | 3,5-diCl | CF3 | I | CO2Me | |
| 12-15 | 3,5-diCl | CF3 | CH3 | CO2Me | |
| 12-16 | 3,5-diCl | CF3 | Cl | CH3 | |
| 12-17 | 3,5-diCl | CF3 | CN | F | |
| 12-18 | 3,5-diCl | CF3 | CH3 | NO2 | |
| 12-19 | 3,5-diCl | CF3 | CH3 | NH2 | |
| 12-20 | 3,5-diCl | CF3 | Br | NO2 | |
| 12-21 | 3,5-diCl | CF3 | Br | NH2 | |
| 12-22 | 3-CF3 | CF3 | NO2 | CO2Me | |
| 12-23 | 3-CF3 | CF3 | NO2 | CO2H | |
| 12-24 | 3,5-diCF3 | CF3 | NO2 | CO2Me | |
| 12-25 | 3,5-diCF3 | CF3 | NO2 | CO2H | |
| 12-26 | 3,4-diCl | CF3 | NO2 | CO2Me | |
| 12-27 | 3,4-diCl | CF3 | NO2 | CO2H | |
| 12-28 | 3-Cl | CF3 | NO2 | CO2Me | |
| 12-29 | 3-Cl | CF3 | NO2 | CO2H | |
| 12-30 | 3,5-diBr | CF3 | NO2 | CO2Me | |
| 12-31 | 3,4,5-triCl | CF3 | NO2 | CO2Me | |
| 12-32 | 3,5-diMe-4-NO2 | CF3 | NO2 | CO2Me | |
| 12-33 | 3-NO2 | CF3 | NO2 | CO2Me | |
| 12-34 | 3-CH3 | CF3 | NO2 | CO2Me | |
| 12-35 | 3-CH3O | CF3 | NO2 | CO2Me | |
| 12-36 | 3-CN | CF3 | NO2 | CO2Me | |
| 12-37 | 3-CF3O | CF3 | NO2 | CO2Me | |
| 12-38 | 3-CH3S | CF3 | NO2 | CO2Me | |
| 12-39 | 3-CH3S(O) | CF3 | NO2 | CO2Me | |
| 12-40 | 3-CH3S(O)2 | CF3 | NO2 | CO2Me | |
| 12-41 | 3-CF3S | CF3 | NO2 | CO2Me | |
| 12-42 | 3-CF3S(O) | CF3 | NO2 | CO2Me | |
| 12-43 | 3-CF3S(O)2 | CF3 | NO2 | CO2Me | |
| 12-44 | 3-OH | CF3 | NO2 | CO2Me | |
| 12-45 | 3-SH | CF3 | NO2 | CO2Me | |
| 12-46 | 3-NO2 | CF3 | NO2 | CO2H | |
| 12-47 | 3,4,5-triCl | CF3 | NO2 | CO2H | |
| 12-48 | 2-Cl | CF3 | NO2 | CO2Me | |
| 12-49 | 2-Cl | CF3 | NO2 | CO2H | |
| 12-50 | 4-Cl | CF3 | NO2 | CO2Me | |
| 12-51 | 4-Cl | CF3 | NO2 | CO2H | |
| 12-52 | 3,5-diCl | CF3 | CF3 | CO2Et | |
| 12-53 | 3,5-diCl | CF3 | CF3 | CO2H | |
| 12-54 | 3,5-diMe-4-NO2 | CF3 | NO2 | CO2H | |
| 12-55 | 3,4,5-triCl | CF3 | NO2 | CO2Me | |
| 12-56 | 3,5-diCl | CF3 | CN | CO2H | |
| 12-57 | 3,5-diCl | CF3 | CN | CO2Me | |
| 12-58 | 3,5-diCF3 | CF3 | CF3 | CO2Et | |
| 12-59 | 3,5-diCl | CF3 | CF3 | F | |
| 12-60 | 3,5-diCl | CF3 | CF3 | NO2 | |
| 12-61 | 3,5-diCl | CF3 | CF3 | NH2 | |
| 12-62 | 3,5-diCl | CF3 | F | CO2Et | |
| 12-63 | 3,4,5-triCl | CF3 | CF3 | CO2Et | |
| 12-64 | 3,4,5-triCl | CF3 | CF3 | CO2H | |

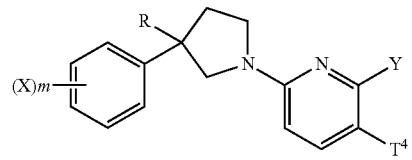

TABLE 13

| | 1H-NMR |
|---|---|
| 1-2 | 1H-NMR (CDCl3) δ: 2.50-2.60 (1H, m), 2.83-2.91 (1H, m), 3.49-3.65 (2H, m), 3.82 (1H, d), 4.12 (1H, d), 4.75 (2H, d), 6.61 (2H, d), 7.21 (1H, dd), 7.29 (2H, d), 7.33-7.40 (3H, m), 7.68 (1H, td), |
| 1-3 | 1H-NMR (CDCl3) δ: 2.51-2.56 (4H, m), 2.83-2.87 (1H, m), 3.50-3.56 (2H, m), 3.78 (1H, d), 4.00-4.15 (3H, m), 6.03 (1H, br s), 6.38-6.41 (2H, m), 7.26-7.39 (4H, m). |
| 1-4 | 1H-NMR (CDCl3) δ: 2.49-2.55 (4H, m), 2.80-2.88 (1H, m), 3.50-3.56 (2H, m), 3.78 (1H, d), 4.08 (1H, d), 4.71 (2H, d), 6.39-6.41 (2H, m), 7.10-7.18 (2H, m), 7.32-7.43 (4H, m), 7.65-7.68 (1H, m), |
| 1-6 | 1H-NMR (CDCl3) δ: 2.50-2.63 (1H, m), 2.86-2.90 (1H, m), 3.53-3.58 (2H, m), 3.78-3.81 (1H, m), 4.10-4.14 (1H, m), 4.78 (2H, d), 6.23-6.28 (1H, m), 6.43-6.46 (1H, m), 7.17-7.40 (5H, m), 7.67- |
| 1-7 | 1H-NMR (CDCl3) δ: 2.55-2.57 (1H, m), 2.87-2.88 (1H, m), 3.51-3.61 (2H, m), 3.80 (1H, d), 4.08-4.19 (3H, m), 6.53-6.56 (2H, m), 6.87-6.91 (1H, m), 7.26-7.27 (1H, m), 7.39-7.42 (1H, m), 7.85- |
| 1-8 | 1H-NMR (CDCl3) δ: 2.53-2.60 (1H, m), 2.86-2.90 (1H, m), 3.53-3.56 (2H, m), 3.79 (1H, d), 4.09 (1H, d), 4.80 (2H, d), 6.52-6.56 (2H, m), 7.20-7.27 (2H, m), 7.38-7.39 (2H, m), 7.70-7.73 (2H, m), |
| 1-9 | 1H-NMR (CDCl3) δ: 2.56-2.58 (1H, m), 2.85-2.93 (1H, m), 3.51-3.58 (2H, m), 3.76 (1H, d), 4.10-4.14 (3H, m), 6.56-6.61 (2H, m), 6.75-6.76 (1H, m), 7.26-7.29 (1H, m), 7.40-7.40 (1H, m), 7.69 |
| 1-10 | 1H-NMR (CDCl3) δ: 2.53-2.60 (1H, m), 2.85-2.90 (1H, m), 3.46-3.59 (2H, m), 3.78 (1H, d), 4.08 (1H, d), 4.77 (2H, d) 6.55-6.56 (1H, m), 6.75-6.78 (1H, m), 7.18-7.44 (5H, m), 7.65-7.70 (2H, m), |
| 1-11 | 1H-NMR (CDCl3) δ: 0.62-0.65 (2H, m), 0.83-0.89 (2H, m), 2.54-2.61 (1H, m), 2.86-2.90 (2H, m), 3.47-3.57 (2H, m), 3.76 (1H, d), 4.06 (1H, d), 6.34 (1H, br s), 6.52-6.55 (1H, m), 6.71 (1H, d), |
| 1-12 | 1H-NMR (CDCl3) δ: 2:55-2.60 (1H, m), 2.74 (2H, t, J = 6.3 Hz), 2.86-2.90 (1H, m), 3.50-3.57 (2H, m), 3.67-3.79 (3H, m), 4.08 (1H, d), 8.53-6.56 (1H, m), 6.74-6.81 (2H, m), 7.27-7.27 (1H, m), |
| 1-15 | 1H-NMR (CDCl3) δ: 2.56-2.66 (1H, m), 2.90-2.98 (1H, m), 3.52-3.68 (2H, m), 3.83 (1H, d), 4.04-4.16 (3H, m), 6.09 (1H, t), 6.75 (1H, dd), 7.10 (1H, d), 7.28 (2H, d), 7.40-7.43 (2H, m). |
| 1-16 | 1H-NMR (CDCl3) δ: 2.54-2.65 (1H, m), 2.89-2.97 (1H, m), 3.51-3.67 (2H, m), 3.83 (1H, d), 4.13 (1H, d), 4.74 (2H, d), 6.75 (1H, dd), 7.08 (1H, d), 7.15-7.23 (2H, m), 7.28 (2H, br s), 7.37 (1H, d), |
| 1-17 | 1H-NMR (CDCl3) δ: 2.57-2.67 (1H, m), 2.88-2.97 (1H, m), 3.49-3.67 (2H, m), 3.87 (1H, d), 4.15 (1H, d), 4.75 (2H, d), 6.74 (1H, dd), 7.08 (1H, d), 7.14 (1H, t), 7.21 (1H, dd), 7.26-7.38 (5H, m), |
| 1-18 | 1H-NMR (CDCl3) δ: 2.58-2.68 (1H, m), 2.91-3.00 (1H, m), 3.50-3.68 (2H, m), 3.87 (1H, d), 4.04-4.17 (3H, m), 6.06 (1H, t), 6.75 (1H, d), 7.10 (1H, s), 7.26-7.42 (5H, m). |
| 1-21 | 1H-NMR (CDCl3) δ: 2.61-2.72 (1H, m). 2.98-3.06 (1H, m), 3.53-3.70 (2H, m), 3.90 (1H, d), 4.09 (2H, dt), 4.22 (1H, d), 6.08 (1H, t), 6.76 (1H, dd), 7.11 (1H, d), 7.42 (1H, d), 7.57-7.69 (4H, m). |

TABLE 13-continued

| | 1H-NMR |
|---|---|

1-22 1H-NMR (CDCl3) δ: 2.62-2.73 (1H, m), 3.03-3.11 (1H, m), 3.57-3.73 (2H, m), 3.89 (1H, d), 4.27 (1H, d), 4.75 (2H, d), 6.79 (1H, dd), 7.12 (1H, d), 7.16-7.24 (2H, m), 7.37 (1H, d), 7.51 (1H, d), 7.70 (1H, td), 7.84 (2H, br s), 7.95 (1H, br s), 8.52 (1H, d).

1-23 1H-NMR (CDCl3) δ: 2.63-2.73 (1H, m), 3.04-3.13 (1H, m), 3.58-3.74 (2H, m), 3.89 (1H, d), 4.10 (2H, td), 4.28 (1H, d), 6.07 (1H, t), 6.80 (1H, dd), 7.15 (1H, d), 7.43 (1H, d),7.83 (2H, br s), 7.95

1-25 1H-NMR (CDCl3) δ: 2.54-2.61 (1H, m), 2.86-2.94 (1H, m), 3.52-3.64 (2H, m), 3.81 (1H, d), 4.11 (1H, d), 4.72 (2H, d), 6.69-6.72 (1H, m), 6.82-6.83 (1H, m), 7.15-7.40 (5H, m), 7.50-7.53 (1H, m), 1-27 1H-NMR (CDCl3) δ: 2.55-2.63 (1H, m), 2.90-2.94 (1H, m), 3.55-3.62 (2H, m), 3.81-3.87 (1H, m), 4.11-4.14 (1H, m), 4.78 (2H, d), 6.76-6.79 (1H, m), 6.87-6.88 (1H, m), 7.26-7.35 (5H, m), 7.57-7.60 (1H, m), 7.68-7.70 (1H, m), 7.79-7.82 (1H, m) 8.55-8-57 (1H, 1-31 1H-NMR (CDCl3) δ: 2.53-2.63 (1H, m), 2.88-2.96 (1H, m), 3.45 (3H, s), 3.56-3.68 (2H, m), 3.82-3.86 (1H, m), 4.14-4.17 (1H, m), 4.74 (2H, d, J = 5.1 Hz), 6.72-6.75 (1H, m), 7.18-7.21 (1H, m), 7.28-7.29 (4H, m), 7.38-7.41 (2H, m), 7.53-7.55 (1H, m), 7.67-7.

1-38 1H-NMR (CDCl3) δ: 2.46-2.56 (1H, m), 2.78-2.87 (1H, m), 3.49-3.57 (2H, m), 3.77 (1H, d), 4.06 (1H, d), 4.70 (2H, d), 5.79 (1H, d), 5.97-6.00 (1H, m), 7.18-7.41 (7H, m), 7.65-7.68 (1H, m), 8.56

1-39 1H-NMR (CDCl3) δ: 2.53-2.61 (1H, m), 2.84-2.92 (1H, m), 3.55-3.67 (2H, m), 3.83 (1H, d), 4.15 (1H, d), 4.72 (2H, d), 6.36-6.39 (1H, m), 7.25-7.36 (4H, m), 7.64-7.70 (2H, m), 7.92-7.95 (2H, m), 1-54 1H-NMR (CDCl3) δ: 2.55-2.64 (1H, m), 2.89-2.94 (1H, m), 3.49-3.66 (2H, m), 3.84 (1H, d), 4.13 (1H, d), 4.74 (2H, d), 6.74 (1H, dd), 7.07 (1H, d), 7.16-7.27 (3H, m), 7.38 (1H, d), 7.47-7.52 (3H, 1-56 1H-NMR (CDCl3) δ: 2.55-2.62 (1H, m), 2.88-2.96 (1H, m), 3.52-3.67 (2H, m), 3.82 (1H, d), 4.12 (1H, d), 4.74 (2H, d), 6.75(1H, dd), 7.08 (1H, d), 7.21 (2H, t), 7.36 (1H, d), 7.42 (2H, s), 7.49 (1H, 1-57 1H-NMR (CDCl3) δ: 2.54-2.66 (1H, m), 2.89-2.97 (1H, m), 3.53-3.69 (2H, m), 3.82 (1H, d), 4.03-4.15 (3H, m), 6.08 (1H, br s), 6.75 (1H, dd), 7.10 (1H, s), 7.40-7.42 (3H, m).

1-60 1H-NMR (CDCl3) δ: 2.36 (6H, s), 2.56-2.66 (1H, m), 2.91-2.99 (1H, m), 3.51-3.67 (2H, m), 3.85 (1H, d), 4.15 (1H, d), 4.74 (2H, d, J = 4.9 Hz), 6.75 (1H, dd), 7.09 (1H, d), 7.15-7.23 (4H, m), 7.37

1-61 1H-NMR (CDCl3) δ: 2.37 (6H, s), 2.57-2.68 (1H, m), 2.92-3.00 (1H, m), 3.52-3.68 (2H, m), 3.86 (1H, d), 4.03-4.18 (3H, m), 6.09 (1H, t,), 6.75 (1H, dd), 7.11 (1H, d), 7.15 (2H, s), 7.41 (1H, d).

1-63 1H-NMR (acetone-d6) δ: 2.72-2.85 (1H, m), 3.03-3.07 (1H, m), 3.63-3.71 (2H, m), 4.04 (1H), 4.38 (1H, d), 6.58 (1H, br s), 6.85-6.88 (1H, m), 7.02 (1H, d), 7.23 (1H, br s), 7.53-7.59 (4H, m).

1-73 1H-NMR (CDCl3) δ: 2.09 (1H, s), 2.58-2.62 (1H, m), 2.90-2.94 (1H, m), 3.57-3.61 (2H, m), 3.83 (1H, d), 4.13 (1H), 4.22 (2H, q), 6.04 (1H, br s), 6.73-6.75 (1H, m), 7.07 (1H, d), 7.27-7.28 (2H, 1-74 1H-NMR (acetone-d6) δ: 2.77-2.85 (1H, m), 3.08-3.10 (1H, m), 3.66-3.68 (2H, m), 4.09 (1H, d), 4.33-4.46 (3H, m), 6.94-6.97 (1H, m), 7.14 (1H, d), 7.55-7.63 (3H, m), 8.20-8.23 (1H, m).

1-75 1H-NMR (CDCl3) δ: 1.50 (6H, s), 2.17 (3H, s), 2.57-2.62 (1H, m), 2.90-2.94 (1H, m), 3.02 (2H, s), 3.56-3.59 (2H, m), 3.82 (1H, d), 4.11 (1H, d), 5.82 (1H, br s), 6.71-6.73 (1H, m), 7.05 (1H, d), 1-78 1H-NMR (CDCl3) δ: 2.54-2.64 (1H, m), 2.87-2.95 (1H, m), 3.53-3.69 (2H, m), 3.85 (1H, d), 4.15 (1H, d), 4.79 (2H, d), 6.95 (1H, dd), 7.17-7.21 (1H, m), 7.28 (2H, s), 7.35 (1H, d), 7.41 (1H, t), 7.65 (1H, td), 7.96 (1H, d), 8.10 (1H, d), 8.66-8.58 (2H, m).

1-80 1H-NMR (CDCl3) δ: 2.64-2.75 (1H, m), 3.02-3.10 (1H, m), 3.54-3.73 (2H, m), 3.93 (1H, d), 4.04-4.15 (2H, m), 4.25 (1H, d), 6.04 (1H, t), 6.78 (1H, dd), 7.13 (1H, d), 7.43 (1H, d), 7.65 (1H, t), 7.76

1-81 1H-NMR (CDCl3) δ: 2.51-2.61 (1H, m), 2.84-2.92 (1H, m), 3.45-3.61 (2H, m), 3.79 (1H, d), 4.08 (1H, d), 5.08 (2H, d), 6.49-6.54 (2H, m), 7.22-7.28 (3H, m), 7.36 (1H, d), 7.40 (1H, t), 7.72 (1H 1-82 1H-NMR (CDCl3) δ: 2.65-2.77 (1H, m), 3.18-3.26 (1H, m), 3.59 (2H, d), 3.99 (1H, d), 4.48 (1H, d), 4.75 (2H, d), 6.76 (1H, dd), 7.08-7.51 (9H, m), 7.70 (1H, td), 8.53 (1H, d).

1-83 1H-NMR (CDCl3) δ: 2.65-2.76 (1H, m), 3.18-3.25 (1H, m), 3.59 (2H, d), 3.99 (1H, d), 4.49 (1H, d), 4.74 (2H, d), 6.76 (1H, dd), 7.07-7.38 (6H, m), 7.53 (2H, dt), 7.70 (1H, td), 8.52 (1H, d).

1-84 1H-NMR (CDCl3) δ: 2.61-2.64 (1H, m), 2.89-2.93 (1H, m), 3.57-3.60 (2H, m), 3.82 (1H, d), 4.12 (1H, d), 4.62 (2H, d), 6.42 (1H, br s), 6.71-6.74 (1H, m), 7.06 (1H, d), 7.27-7.42 (5H, m), 7.79 (1H, 1-85 1H-NMR (CDCl3) δ: 2.57-2.63 (1H, m), 2.88-2.94 (1H, m), 3.54-3.63 (2H, m), 3.82 (1H, d), 4.13 (1H, d), 4.59 (2H, d), 6.64-6.74 (2H, m), 7.05 (1H, d), 7.28 (4H, d), 7.41-7.43 (2H, m), 8.51-8.53

1-86 1H-NMR (CDCL3) δ: 2.55-2.65 (1H, m), 2.89-2.97 (1H, m), 3.56-3.68 (2H, m), 3.83 (1H, d), 4.14 (1H, d), 4.72 (2H, d), 6.74-6.79 (2H, m), 7.09-7.10 (1H, m), 7.25-7.50 (5H, m) 7.68 (1H, t).

1-87 1H-NMR (CDCl3) δ: 2.57-2.65 (1H, m), 2.90-2.95 (1H, m), 3.50-3.62 (2H, m), 3.82 (1H, d), 4.12 (1H, d), 4.53 (2H, d), 6.66-6.70 (2H, m), 7.02 (1H, d), 7.25-7.41 (5H, m), 7.72-7.74 (1H, m), 8.26

1-88 1H-NMR (CDCl3) δ: 2.58-2.63 (1H, m), 2.91-2.95 (1H, m), 3.53-3.68 (2H, m), 3.84 (1H, d), 4.14 (1H, d), 4.88 (2H, d), 6.75-6.78 (1H, m), 7.08 (1H, d), 7.20-7.29 (4H, m), 7.41-7.41 (1H, m), 7.55

1-90 1H-NMR (CDCl3) δ: 2.56-2.61 (1H, m), 2.87-2.95 (1H, m), 3.53-3.65 (2H, m), 3.81 (1H, d), 3.99-4.13 (3H, m), 6.20-6.22 (1H, m), 6.68-6.71 (1H, m), 6.81 (1H, d), 7.27-7.28 (2H, m), 7.40-7.41

1-91 1H-NMR (CDCl3) δ: 2.55-2.60 (1H, m), 2.88-2.92 (1H, m), 3.52-3.65 (2H, m), 3.81 (1H, d), 4.11 (1H, d) 4.67 (2H, d) 6.74-6.82 (3H, m), 7.23-7.28 (4H, m) 7.38-7.39 (1H, m), 7.50 (1H, d), 7.64

1-92 1H-NMR (CDCl3) δ: 2.55-2.62 (1H, m), 2.86-2.94 (1H, m), 3.12 (6H, d), 3.53-3.63 (2H, m), 3.82 (1H, m), 4.13 (1H, d), 6.62-6.67 (2H, m), 7.25-7.28 (1H, m), 7.40 (1H, d), 8.04 (1H, d), 8.54 (1H, 1-93 1H-NMR (CDCl3) δ: 1.28 (3H, t), 2.59-2.64 (1H, m), 2.93-2.97 (1H, m), 3.58-3.67 (2H, m), 3.85 (1H, d), 4.10-4.18 (3H, m), 6.75-6.78 (1H, m), 7.09-7.50 (4H, m), 7.70-7.72 (1H, m), 8.47-8.50

1-95 1H-NMR (CDCl3) δ: 2.55-2.65 (1H, m), 2.88-2.97 (1H, m), 3.47-3.65 (2H, m), 3.86 (1H, d), 4.14 (1H, d), 4.73 (2H, d), 6.73 (1H, dd), 7.06 (1H, d), 7.23-7.15 (2H, m), 7.31-7.41 (5H, m), 7.48 (1H, 1-96 1H-NMR (CDCl3) δ: 2.56-2.67 (1H, m), 2.90-2.99 (1H, m), 3.48-3.67 (2H, m), 3.86 (1H, d), 4.03-4.16 (3H, m), 6.06 (1H, br s), 6.73 (1H, dd), 7.09 (1H, d), 7.33 (2H, d), 7.38-7.42 (3H, m).

1-97 1H-NMR (CDCl3) δ: 2.58-2.63 (1H, m), 2.91-2.96 (1H, m), 3.55-3.67 (2H, m), 3.81-3.84 (1H, m), 4.07-4.18 (3H, m) 6.70-6.80 (3H, m), 7.27-7.42 (3H, m), 7.75-7.78 (1H, m)

1-98 1H-NMR (CDCl3) δ: 2.53-2.63 (1H, m), 2.89-2.92 (1H, m), 3.21-3.35 (1H, m), 3.59-3.78 (3H, m), 4.10-4.13 (1H, m), 5.94-5.97 (2H, m), 6.73-6.85 (2H, m), 7.23-7.56 (4H, m)

1-99 1H-NMR (CDCl3) δ: 2.63-2.68 (1H, m), 3.02-3.07 (1H, m), 3.55-3.71 (2H, m), 3.86-3.90 (1H, m), 4.23-4.26 (1H, m), 4.74 (2H, d), 6.74-6.77 (1H, m), 6.86-6.86 (1H, m), 7.07-7.10 (1H, m), 7.20-7.22 (1H, m), 7.31-7.34 (1H, m), 7.53-7.56 (1H, m), 7.68-7.70 (1H, 1-100 1H-NMR (CDCl3) δ: 2.65-2.67 (1H, m), 3.02-3.10 (1H, m), 3.59-3.66 (2H, m), 3.86-3.90 (1H, m), 4.11-4.20 (3H, m), 5.99-6.02 (1H, m), 6.78-6.85 (2H, m), 7.50-7.53 (1H, m), 7.84-7.95 (3H, m).

TABLE 13-continued

| | 1H-NMR |
|---|---|
| 1-101 | 1H-NMR (CDCl3) δ: 2.54-2.64 (1H, m), 2.89-2.97 (1H, m), 3.54-3.70 (2H, m), 3.85 (1H, d), 4.04-4.18 (3H, m), 6.94 (1H, dd), 7.29 (2H, s), 7.41 (H, t), 7.92 (1H, d), 8.14-8.06 (2H, m). |
| 1-102 | 1H-NMR (CDCl3) δ: 2.46-2.61 (1H, m), 2.83-2.91 (1H, m), 3.50-3.60 (2H, m), 3.77-3.81 (1H, m), 4.07-4.10 (1H, m), 4.70 (2H, d, J = 4.9 Hz), 6.67-6.70 (1H, m), 6.80-6.81 (1H, m), 7.15-7.17 (2H, m), 7.30-7.32 (1H, m), 7.40-7.43 (2H, m), 7.48-7.51 (1H, m), 7. |
| 2-8 | 1H-NMR (CDCl3) δ: 2.54-2.65 (1H, m). 2.88-2.96 (1H, m), 3.50-3.68 (2H, m), 3.84 (1H, d), 4.13 (1H, d), 6.71 (2H, d) 7.30 (2H, d) 7.41 (1H, t), 7.54 (2H, d), 8.85 (1H, s). |
| 2-29 | 1H-NMR (CDCl3) δ: 2.14 (3H, s), 2.54-2.64 (1H, m), 2.87-2.95 (1H, m), 3.49-3.65 (2H, m), 3.83 (1H, d), 4.12(1H, d), 6.51-6.54 (2H, m), 7.17 (1H, d), 7.30 (2H, d), 7.41 (1H, t), 8.68 (1H, s). |
| 2-31 | 1H-NMR (CDCl3) δ: 2.59-2.69 (1H, m), 2.92-3.01 (1H, m), 3.57-3.73 (2H, m), 3.88 (1H, d). 4.18 (1H, d), 6.83 (1H, dd), 6.94 (1H, d), 7.44-7.30 (2H, m), 8.73 (1H, s). |
| 2-40 | 1H-NMR (DMSO-d6) δ: 2.62-2.73 (1H, m), 2.95-3.03 (1H, m), 3.49-3.55 (2H, m), 3.90 (1H, d), 4.31 (1H, d), 7.09 (1H, d), 7.29 (1H, d), 7.61 (1H, d), 7.68 (2H, d), 7.71 (1H, t), 8.26 (1H, s), 8.98 |
| 3-3 | 1H-NMR (CDCl3) δ: 1.99 (3H, s), 2.50-2.58 (1H, m), 2.82-2.87 (1H, m), 3.45-3.51 (2H, m), 3.74 (1H, d), 4.02 (1H, d), 4.41(2H, d), 6.43-6.46 (1H, m), 6.58 (1H, d) 7.26-7.38 (4H, m). |
| 3-4 | 1H-NMR (CDCl3) δ: 1.98-2.02 (3H, m), 2.53-2.61 (1H, m), 2.81-2.89 (1H, m), 3.46-3.52 (2H, m), 3.74 (1H, d), 4.02 (1H), 4.42-4.44 (2H, m), 5.78-5.81 (1H, m), 6.49-6.51 (1H, m), 6.77 (1H, d), |
| 3-11 | 1H-NMR (CDCl3) δ: 2.13-2.18 (3H, m), 2.51-2.53 (1H, m), 2.81-2.83 (1H, m) 3.45-3.56 (2H, m), 3.75-3.78 (1H, m), 4.01-4.04 (1H, m), 4.25 (1H, s), 4.57 (1H, d), 6.40-6.44 (2H, m), 6.93-6.96 (1H, m), |
| 3-102 | 1H-NMR (CDCl3) δ: 2.03 (3H, s), 2.53-2.60 (1H, m), 2.83-2.91 (1H, m), 3.51-3.59 (2H, m), 3.78-3.82 (1H, m), 4.07-4.13 (1H, m), 4.50-4.55 (2H, m), 5.72-5.76 (1H, m), 6.70-6.78 (2H, m), 7.27- |
| 3-113 | 1H-NMR (CDCl3) δ: 1.99 (3H, s), 2.58-2.68 (1H, m), 2.99-3.03 (1H, m), 3.51-3.67 (2H, m), 3.83-3.86 (1H, m), 4.18-4.21 (1H, m), 4.50 (2H, d), 5.73-5.76 (1H, m), 6.74-6.81 (2H, m), 7.47-7.50 |
| 4-1 | 1H-NMR (CDCl3) δ: 2.56-2.64 (1H, m), 2.89-2.98 (1H, m), 3.63-3.67 (2H, m), 3.87 (1H, d), 4.19 (1H, d), 6.57 (2H, d), 7.27 (2H, br s), 7.42 (1H, t), 8.18 (2H, d). |
| 4-2 | 1H-NMR (CDCl3) δ: 2.51-2.62 (1H, m), 2.86-2.94 (1H, m), 3.56-3.61 (2H, m), 3.80 (1H, d), 4.12 (1H, d), 6.59 (2H, d), 7.26 (2H, br s), 7.41(1H, t), 7.52 (2H, d). |
| 4-3 | 1H-NMR (CDCl3) δ: 2.45-2.54 (1H, m), 2.74-2.82 (1H, m). 3.34-3.47 (4H, m), 3.73 (1H, d), 3.93 (1H, d), 6.49-6.51 (2H, m), 6.67-6.71 (2H, m), 7.30 (2H, br s), 7.36 (1H, t). |
| 4-5 | 1H-NMR (DMSO-d6) δ: 2.58-2.72 (1H, m), 2.88-3.01 (1H, m), 3.41-3.53 (2H, m), 3.85 (1H, d), 4.26 (1H, d), 6.71 (2H, d), 7.65-7.72 (3H, m), 7.78-(2H, m), 12.25 (1H, br s) |
| 4-6 | 1H-NMR (CDCl3) δ: 2.53-2.67 (1H, m), 2.89-2.97 (1H, m), 3.50-3.71 (2H, m), 3.83 (1H, d), 3.85 (3H, s), 4.15 (1H, d), 6.69 (1H, dd), 6.75 (1H, d), 7.26 (3H, s) 7.42 (1H, t), 7.61 (1H, d). |
| 4-7 | 1H-NMR (DMSO-d6) δ: 2.58-2.72 (1H, m), 2.91-3.04 (1H, m), 3.47-3.57 (2H, m), 3.87 (1H, d), 4.32 (1H, d), 6.86 (1H, dd), 7.04 (1H, d), 7.65 (2H, d), 7.71 (1H, t), 7.78 (1H, d). |
| 4-8 | 1H-NMR (CDCl3) δ: 2.46-2.56 (1H, m), 2.79-2.85 (1H, m), 3.52-3.57 (2H, m), 3.76-3.86 (4H, m), 4.01-4.12 (1H, m), 5.68-5.76 (2H, m), 5.87-5.99 (1H, m), 6.26-6.32 (2H, m), 7.38-7.41 (1H, m), |
| 4-10 | 1H-NMR (CDCl3) δ: 2.53-2.58 (1H, m), 2.86-2.92 (1H, m), 3.52-3.62 (2H, m), 3.80 (1H, d), 3.87 (3H, s), 4.11 (1H, d), 6.45-6.48 (1H, m), 6.61 (1H, d), 7.26-7.27 (2H, m), 7.40-7.41 (1H, m), 7.88 |
| 4-11 | 1H-NMR (CDCl3) δ: 1.59 (9H, s), 2.54-2.56 (1H, m), 2.84-2.92 (1H, m), 3.53-3.56 (2H, m), 3.79 (1H, d), 4.09 (1H, d), 6.43-6.46 (1H, m), 6.58 (1H, d), 7.24-7.26 (2H, m), 7.40-7.40 (1H, m), 7.80 |
| 4-12 | 1H-NMR (acetone-d6) δ: 2.74-2.84 (1H, m), 3.05-3.10 (1H, m), 3.64-3.69 (2H, m), 4.04 (1H, d), 4.40 (1H, d). 6.70-6.77 (2H, m), 7.55-7.65 (3H, m ), 7.91 (1H, d). |
| 4-13 | 1H-NMR (CDCl3) δ: 2.53-2.60 (1H, m), 2.84-2.93 (1H, m), 3.52-3.62 (2H, m), 3.80-3.87 (4H, m), 4.11 (1H, d), 6.49-6.52 (1H, m), 6.84 (1H, d), 7.26-7.27 (2H, m), 7.40-7.41 (1H, m), 7.87 (1H, d). |
| 4-14 | 1H-NMR (CDCl3) δ: 2.51-2.56 (1H, m), 2.85-2.86 (1H, m), 3.51-3.57 (2H, m), 3.74-3.87 (4H, m), 4.09 (1H, d), 6.54-6.56 (1H, m), 7.17-7.18 (1H, m), 7.27-7.31 (2H, m), 7.38-7.39 (1H, m), 7.85 |
| 4-15 | 1H-NMR (CDCl3) δ: 2.53-2.60 (4H, m), 2.84-2.85 (1H, m), 3.52-3.62 (2H, m), 3.79-3.84 (4H, m), 4.11 (1H, d), 6.39-6.44 (2H, m), 7.26-7.29 (2H, m), 7.39-7.39 (1H, m), 7.91-7.94 (1H, m). |
| 4-16 | 1H-NMR (CDCl3) δ: 2.27 (3H, s), 2.49-2.54 (1H, m), 2.78-2.87 (1H, m), 3.38-3.54 (2H, m), 3.74 (1H, d, J = 10.4 Hz), 3.99 (1H, d, J = 10.4 Hz), 6.40-6.43 (1H, m), 6.60-6.62 (1H, m), 7.05-7.08 |
| 4-18 | 1H-NMR (CDCl3) δ: 2.51-2.64 (1H, m), 2.67 (3H, s), 2.87-2.95 (1H, m), 3.51-3.71 (2H, m), 3.84 (1H, d), 4.17 (1H, d), 6.37 (1H, d), 6.45 (1H, dd), 7.28 (2H, br s), 7.41 (1H, t), 8.14 (1H, d). |
| 4-19 | 1H-NMR (CDCl3) δ: 2.19 (3H, s), 2.41-2.58 (1H, m), 2.73-2.81 (1H, m), 3.15-3.51 (4H, m), 3.73 (1H, d), 3.92 (1H, d), 6.34-6.44 (2H, m), 6.66 (1H, d), 7.31-7.41 (3H, m). |
| 4-20 | 1H-NMR (CDCl3) δ: 2.53-2.66 (1H, m), 2.89-2.97 (1H, m), 3.51-3.71 (2H, m), 3.83 (1H, d), 4.16 (1H, d), 6.53 (1H, dd), 6.84 (1H, d), 7.27 (2H, br s), 7.42 (1H, t), 8.07 (1H, d). |
| 4-21 | 1H-NMR (CDCl3) δ: 2.44-2.54 (1H, m), 2.75-2.83 (1H, m), 3.32-3.50 (2H, m), 3.56-3.76 (3H, m), 3.92 (1H, d), 6.46 (1H, dd), 6.70-6.78 (2H, m), 7.29 (2H, br s), 7.37 (1H, t). |
| 4-23 | 1H-NMR (DMSO-d6) δ: 2.63-2.75 (1H, m), 2.96-3.12 (1H, m), 3.49-3.59 (2H, m), 3.91 (1H, d), 4.41 (1H, d), 6.88 (1H, dd), 7.06 (1H, d), 7.67-7.90 (5H, m), 13.00 (1H, br s). |
| 4-24 | 1H-NMR (CDCl3) δ: 2.61-2.73 (1H, m), 3.03-3.13 (1H, m), 3.58-3.75 (2H, m), 3.85 (3H, s), 3.89 (1H, d), 4.29 (1H, d), 6.73 (1H, dd), 6.79 (1H, d), 7.80-7.85 (3H, m), 7.95 (1H, br s). |
| 4-25 | 1H-NMR (DMSO-d6) δ: 2.66-2.80 (1H, m), 3.11-3.22 (1H, m), 3.51-3.61 (2H, m), 3.93 (1H, d), 4.51 (1H, d), 6.90 (1H, d), 7.06 (1H, br s), 7.81 (1H, t), 8.22 (3H, br s), 13.03 (1H, br s). |
| 4-26 | 1H-NMR (CDCl3) δ: 2.54-2.64 (1H, m), 2.89-2.97 (1H, m), 3.50-3.69 (2H, m), 3.84(1H, d), 3.85(3H, s), 4.15 (1H, d), 6.68 (1H, dd), 6.74 (1H, d), 7.22 (1H, dd), 7.47-7.52 (2H, m), 7.81 (1H, |
| 4-47 | 1H-NMR (DMSO-d6) δ: 2.59-2.74 (1H, m), 2.90-3.00 (1H, m), 3.49-3.57 (2H, m), 3.90 (1H, d), 4.30 (1H, d), 6.86 (1H, dd), 7.03 (1H, d), 7.55 (1H, d), 7.73-7.86 (3H, m), 12.98 (1H, br s). |
| 4-29 | 1H-NMR (DMSO-d6) δ: 2.59-2.71 (1H, m), 2.90-3.01 (1H, m), 3.49-3.57 (2H, m), 3.89 (1H, d), 4.31 (1H, d), 6.87 (1H, dd), 7.05 (1H, d), 7.50 (3H, br s), 7.64 (1H, br s), 7.78 (1H, d), 13.00 (1H, |
| 4-32 | 1H-NMR (CDCl3) δ: 2.36 (6H, s), 2.56-2.66 (1H, m), 2.92-3.00 (1H, m), 3.52-3.69 (2H, m), 3.93-3.84 (4H, m), 4.17 (1H, d), 6.69 (1H, dd), 6.75(1H, d), 7.14 (2H, s), 7.81 (1H, d). |
| 4-33 | 1H-NMR (CDCl3) δ: 2.63-2.73 (1H, m), 3.01-3.09 (1H, m), 3.55-3.73 (2H, m), 3.85 (3H, s), 3.92 (1H, d), 4.26 (1H, d), 6.71(1H, dd), 6.77 (1H, d), 7.62-7.83 (3H, m), 8.27-8.31 (2H, m). |
| 4-47 | 1H-NMR (DMSO-d6) δ: 2.66-2.77 (1H, m), 3.01-3.10 (1H, m), 3.50-3.62 (2H, m), 3.95 (1H, d), 4.43(1H, d), 6.89 (1H, d), 7.08 (1H, s), 7.75-7.81 (2H, m), 8.03 (1H, d), 8.28-8.35 (2H, m), 13.02 |

TABLE 13-continued

| | 1H-NMR |
|---|---|
| 4-48 | 1H-NMR (DMSO-d6) δ: 2.60-2.72 (1H, m), 2.94-3.05 (1H, m), 3.50-3.57 (2H, m), 3.90 (1H, d), 4.32 (1H, d), 6.87 (1H, d) 7.03 (1H, s) 7.79 (1H, d, J = 9.0 Hz), 7.88 (2H, s), 13.03 (1H, s), 3.98 |
| 4-49 | 1H-NMR (CDCl3) δ: 2.64-2.75 (1H, m), 3.18-3.25 (1H, m), 3.55-3.63 (2H, m), 3.84 (3H, s), 3.98 (1H, d), 4.50 (1H, d), 6.67-6.74 (2H, m), 7.32-7.48 (4H, m), 7.82 (1H, d). |
| 4-50 | 1H-NMR (DMSO-d6) δ: 2.67-2.78 (1H, m), 3.23-3.37 (1H, m), 3.46-3.64 (2H, m), 3.91 (1H, d), 4.57 (1H, d), 6.86 (1H, dd), 7.04 (1H, d), 7.43-7.56 (3H, m), 7.64-7.68 (1H, m), 7.80 (1H, d) 13.01 |
| 4-51 | 1H-NMR (CDCl3) δ: 2.55-2.65 (1H, m), 2.89-2.98 (1H, m), 3.49-3.67 (2H, m), 3.84 (3H, s), 3.86 (1H, d), 4.14 (1H, t), 6.66 (1H, dd), 6.73 (1H, d), 7.32 (2H, d), 7.40 (2H, d), 7.80 (1H, d). |
| 4-52 | 1H-NMR (DMSO-d6) δ: 2.58-2.68 (1H, m), 2.88-2.96 (1H, m), 3.45-3.60 (2H, m), 3.90 (1H, d), 4.28 (1H, d), 6.85 (1H, dd), 7.03 (1H, d), 7.52 (2H, d), 7.57 (2H, d), 7.78 (1H, d), 13.02 (1H, br s). |
| 4-53 | 1H-NMR (CDCl3) δ: 1.37 (3H, t), 2.56-2.61 (1H, m), 2.89-2.94 (1H, m), 3.58-3.66 (2H, m), 3.82-3.85 (1H, m), 4.12-4.16 (1H, m), 4.35(2H, q), 6.67-6.70 (1H, m), 6.88-6.89 (1H, m), 7.25-7.28 |
| 4-56 | 1H-NMR (CDCl3) δ: 2.53-2.63 (1H, m), 2.88-2.97 (1H, m), 3.53-3.69 (2H, m), 3.82 (2H, d), 3.85 (3H, s), 4.14 (1H, d), 6.69 (1H, dd), 6.75 (1H, d), 7.41 (2H, d), 7.81 (1H, d). |
| 4-57 | 1H-NMR (DMSO-d6) δ: 2.64-2.67 (1H, m), 2.93-3.00 (1H, m), 3.49-3.52 (2H, m), 3.88-3.90 (1H, m), 4.31-4.35 (1H, m), 6.92-6.95 (1H, m), 7.18-7.21 (1H, m), 7.67-7.69 (3H, m), 7.89-7.92 (1H, m) |
| 4-58 | 1H-NMR (CDCl3) δ: 2.57-2.63 (1H, m), 2.91-2.96 (1H, m), 3.52-3.69 (2H, m), 3.82-3.86 (1H, m), 3.94 (3H, s), 4.11-4.18 (1H, m), 6.73-6.76 (1H, m), 6.89-6.90 (1H, m), 7.27-7.42 (3H, m), 8.01- |
| 4-59 | 1H-NMR (CDCl3) δ: 1.63 (9H, s), 2.53-2.63 (1H, m), 2.87-2.95 (1H, m), 3.53-3.69 (2H, m), 3.84 (1H, d), 4.13 (1H, d), 6.86(1H, dd), 7.28 (2H, d), 7.41 (1H, t), 7.95 (1H, d), 8.10 (1H, d). |
| 4-60 | 1H-NMR (CDCl3) δ: 2.58-2.69 (1H, m), 2.93-3.02 (1H, m), 3.63-3.73 (2H, m), 3.93 (1H, d), 4.27 (1H, d), 7.18 (1H, d), 7.26 (1H, s), 7.30 (2H, d), 7.41 (1H, s), 8.13 (1H, d), 8.20 (1H, s), 9.92 (1H, |
| 4-61 | 1H-NMR (CDCl3) δ: 1.37 (3H, t), 2.60-2.71 (1H, m), 3.01-3.09 (1H, m), 3.60-3.71 (1H, m), 3.88-3.90 (1H, m), 4.28-4.36 (3H, m), 6.71-6.74 (1H, m), 6.91-6.91 (1H, m), 7.84-7.97 (4H, m) |
| 4-62 | 1H-NMR (CDCl3) δ: 2.51-2.61 (1H, m), 2.83-2.91 (1H, m), 3.43-3.58 (2H, m), 3.77 (1H, d), 4.03 (1H, d), 6.71-6.66 (2H, m), 7.10 (1H, t), 7.29 (2H, s), 7.39(1H, s). |
| 4-63 | 1H-NMR (CDCl3) δ: 2.57-2.68 (1H, m), 2.93-3.01 (1H, m), 3.75-3.59 (2H, m), 3.87 (1H, d), 4.20 (1H, d), 6.70 (1H, dd), 6.88 (1H, d), 7.28 (2H, d), 7.43 (1H, t), 8.08 (1H, d). |
| 4-65 | 1H-NMR (CDCl3) δ: 1.37 (3H, t), 2.53-2.58 (1H, m), 2.85-2.93 (1H, m), 3.53-3.62 (2H, m), 3.78-3.81 (1H, m), 4.08-4.16 (1H, m), 4.34 (2H, q), 6.25-6.36 (2H, m), 7.28-7.33 (3H, m), 7.84-7.87 |
| 4-66 | 1H-NMR (CDCl3) δ: 1.36 (3H, t), 2.55-2.62 (1H, m), 2.88-2.94 (1H, m), 3.57-3.63 (2H, m), 3.80-3.84 (1H, m), 4.12-4.15 (1H, m), 4.33 (2H, q), 6.67-6.70 (1H, m), 6.87-6.88 (1H, m), 7.41-7.45 |
| 5-1 | 1H-NMR (CDCl3) δ: 2.50-2.68 (2H, m), 2.74-2.82 (1H, m), 2.90-2.98 (1H, m), 3.16-3.20 (1H, m), 3.61-3.75 (3H, m), 7.20-7.41 (9H, m). |
| 5-2 | 1H-NMR (CDCl3) δ: 2.45-2.55 (1H, m), 2.76-2.85 (1H, m), 3.00-3.09 (1H, m), 3.22-3.35 (2H, m), 4.10 (1H, d), 7.23-7.44 (4H, m). |
| 5-3 | 1H-NMR (CDCl3) δ: 2.33-2.42 (1H, m), 2.55-2.63 (1H, m), 2.74-2.78 (2H, m), 3.09 (1H, d), 3.18 (1H, d), 3.67 (2H, s), 7.26-7.38 (9H, m). |
| 5-4 | 1H-NMR (CDCl3) δ: 2.28-2.38 (1H, m), 2.49-2.59 (1H, m), 2.97-3.06 (1H, m), 3.19-3.30 (2H, m), 3.75 (1H, d), 7.28-7.33 (4H, m). |
| 5-5 | 1H-NMR (CDCl3) δ: 2.31-2.41 (1H, m), 2.55-2.63 (1H, m), 2.70-2.61 (2H, m), 3.08 (1H, d), 3.18 (1H, d), 3.66 (2H, s), 7.24-7.33 (9H, m). |
| 5-6 | 1H-NMR (CDCl3) δ: 2.27-2.36 (1H, m), 2.49-2.59 (1H, m), 2.96-3.05 (1H, m), 3.20-3.29 (2H, m), 3.76 (1H, d), 7.28-7.36 (4H, m). |
| 5-7 | 1H-NMR (CDCl3) δ: 2.50-2.66 (2H, m), 2.76-2.84 (1H, m), 2.91-2.99 (1H, m), 3.16 (1H, dd), 3.61-3.75 (3H, m), 7.17 (1H, t), 7.25-7.35 (6H, m), 7.46 (1H, dd). |
| 5-8 | 1H-NMR (CDCl3) δ: 2.41-2.53 (1H, m), 2.78-2.87 (1H, m), 3.00-3.09 (1H, m), 3.23-3.32 (2H, m), 4.11 (1H, d), 7.18-7.30 (2H, m), 7.48 (1H, dd). |
| 5-9 | 1H-NMR (CDCl3) δ: 2.28-2.37 (1H, m), 2.54-2.62 (1H, m), 2.70-2.82 (2H, m), 3.06 (1H, d), 3.13 (1H, d), 3.66 (2H, s), 7.21-7.33 (6H, m), 7.41 (1H, d), 7.49 (1H, d). |
| 5-10 | 1H-NMR (CDCl3) δ: 2.25-2.34 (1H, m), 2.50-2.59 (1H, m), 2.97-3.06 (1H, m), 3.20-3.28 (2H, m), 3.75 (1H, d), 7.20 (1H, d), 7.44 (2H, d). |
| 5-11 | 1H-NMR (CDCl3) δ: 2.27-2.36 (1H, m), 2.53-2.62 (1H, m), 2.69-2.83 (2H, m), 3.08 (2H, dd) 3.67 |
| 5-12 | 1H-NMR (CDCl3) δ: 2.24-2.33 (1H, m), 2.51-2.56 (1H, m), 2.97-3.07 (1H, m), 3.19-3.26 (2H, m), 3.74 (1H, d), 7.25 (2H, d), 7.35 (1H, t). |
| 5-14 | 1H-NMR (CDCl3) δ: 2.24-2.34 (1H, m), 2.53-2.61 (1H, m), 2.67-2.87 (2H, m), 3.06 (2H, dd) 3.67 (2H, dd), 7.24-7.43 (7H, m). |
| 5-15 | 1H-NMR (CDCl3) δ: 2.22-2.32 (1H, m), 2.49-2.58 (1H, m), 2.98-3.08 (1H, m), 3.20-3.29 (2H, m), |
| 5-16 | 1H-NMR (CDCl3) δ: 2.35-2.44 (1H, m), 2.60-2.68 (1H, m), 2.72-2.85 (2H, m), 3.16 (2H, dd), 3.68 (2H, dd), 7.28-7.34 (5H, m), 7.46 (1H, t), 7.55-7.60 (2H, m), 7.66 (1H, s). |
| 5-17 | 1H-NMR (CDCl3) δ: 2.32-2.41 (1H, m), 2.55-2.65 (1H, m), 2.98-3.07 (1H, m), 3.21-3.33 (2H, m), 3.82 (1H, d), 7.47-7.62 (4H, m). |
| 5-18 | 1H-NMR (CDCl3) δ: 2.29-2.40 (1H, m), 2.63-2.77 (2H, m), 2.88-2.96 (1H, m), 3.09 (1H, d), 3.16 (1H, d), 3.62 (1H, d), 3.76 (1H, d, J = 13.0 Hz), 7.28-7.34 (5H, m), 7.83 (1H, s), 7.89 (2H, s). |
| 5-19 | 1H-NMR (CDCl3) δ: 2.30-2.39 (1H, m), 2.61-2.70 (1H, m), 3.02-3.10 (1H, m), 3.24-3.33 (2H, m), 3.86 (1H, d), 7.81 (2H, s) 7.87 (1H, s). |
| 5-24 | 1H-NMR (CDCl3) δ: 2.35-2.44 (1H, m), 2.63-2.90 (3H, m), 3.17 (2H, s), 3.69 (2H, dd), 7.26-7.34 (5H, m), 7.53 (1H, t), 7.74 (1H, d), 8.18 (1H, dq), 8.34 (1H, s). |
| 5-25 | 1H-NMR (CDCl3) δ: 2.34-2.43 (1H, m), 2.59-2.69 (1H, m), 3.01-3.10 (1H, m), 3.24-3.35 (2H, m), 3.85 (1H, d), 7.57 (1H, t), 7.72 (1H, d), 8.20-8.27 (2H, m). |
| 5-26 | 1H-NMR (CDCl3) δ: 2.31-2.42 (7H, m), 2.55-2.63 (1H, m), 2.75-2.80 (2H, m), 3.11 (2H, dd), 3.67 |
| 5-27 | 1H-NMR (CDCl3) δ: 2.29-2.38 (7H, m). 2.51-2.60 (1H, m), 2.97-3.07 (1H, m), 3.21-3.31 (2H, m), |
| 6-1 | 1H-NMR (CDCl3) δ: 2.34 (6H, s), 5.78-5.80 (1H, m), 6.03-6.04 (1H, m), 7.20 (2H, s). |
| 7-1 | 1H-NMR (CDCl3) δ: 2.52-2.63 (1H, m), 2.88-2.96 (1H, m), 3.60-3.77 (2H, m), 4.00 (1H, d), 4.18-4.07 (2H, m). 4.48 (1H, d); 6.16 (1H, t), 6.43 (1H, d), 7.30 (2H, d), 7.39 (1H, t), 7.95 (1H, dd), 8.62 |
| 7-2 | 1H-NMR (CDCl3) δ: 2.52-2.62 (1H, m), 2.87-2.96 (1H, m), 3.59-3.75 (2H, m), 4.01 (1H, d), 4.48 (1H, d), 4.75 (2H, d), 6.43 (1H, d), 7.25-7.20 (1H, m), 7.31 (2H, d), 7.39 (1H, t), 7.47 (1H, s), 7.69 |

TABLE 13-continued

| | 1H-NMR |
|---|---|
| 7-3 | 1H-NMR (CDCl3) δ: 2.49-2.57 (1H, m), 2.60 (3H, s), 2.84-2.92 (1H, m), 3.59-3.70 (2H, m), 3.95-4.15 (3H, m), 4.45(1H, d), 5.94 (1H, br s), 6.23 (1H, d), 7.26-7.39 (4H, m), 7.58 (1H, d) |
| 7-7 | 1H-NMR (CDCl3) δ: 2.54-2.61 (1H, m), 2.89-2.94 (1H, m), 3.65-3.68 (2H, m), 3.94-3.98 (1H, m), 4.10-4.16 (2H, m), 4.45-4.48 (1H, m), 6.37-6.40 (1H, m), 7.23-7.38 (4H, m), 8.12-8.15 (1H, m) |
| 7-25 | 1H-NMR (CDCl3) δ: 2.54-2.61 (1H, m), 2.88-2.92 (1H, m), 3.64-3.70 (2H, m), 3.98 (1H, d), 4.44 (1H, d), 4.73 (2H, d), 6.54 (1H, d), 7.14-7.40 (6H, m), 7.69-7.74 (2H, m), 8.52 (1H, d) |
| 7-26 | 1H-NMR (CDCl3) δ: 2.53-2.63 (1H, m), 2.88-2.96 (1H, m), 3.68-3.71 (2H, m), 4.05-4.16 (3H, m), 4.45 (1H, d), 6.03 (1H, br s), 6.55 (1H, d), 7.24-7.37 (4H, m), 7.72 (1H, d) |
| 8-23 | 1H-NMR (CDCl3) δ: 2.55-2.65 (1H, m), 2.92-2.97 (1H, m), 3.69-3.77 (2H, m), 3.97-4.01 (1H, m), 4.47-4.51 (1H, m), 4.75 (2H, d), 6.62 (1H, s) 7.24-7.36 (6H, m) 7.68-7.70 (1H, m) 8.51-8.52 (2H, |
| 8-24 | 1H-NMR (CDCl3) δ: 2.58-2.63 (1H, m), 2.93-2.97 (1H, m), 3.71-3.74 (2H, m), 3.96-4.09 (3H, m), 4.47-4.51 (1H, m), 6.42-6.44 (1H, m), 6.61 (1H, s), 7.30 (2H, s), 7.40 (1H, s), 8.41 (1H, s) |
| 8-25 | 1H-NMR (CDCl3) δ: 2.55-2.65 (1H, m), 2.91-2.97 (1H, m), 3.68-3.73 (2H, m), 3.97-4.01 (1H. m), 4.48-4.52 (1H, m), 5.74-5.77 (2H, m), 6.62 (1H, s), 7.20-7.37 (3H, m), 8.52 (1H, s) |
| 11-47 | 1H-NMR (CDCl3) δ: 1.37 (3H, t, J = 7.1 Hz), 2.55-2.66 (1H, m), 2.91-2.99 (1H, m), 3.73-3.75 (2H, m), 4.00-4.04 (1H, m), 4.36 (2H, q, J = 7.1 Hz), 4.49-4.54 (1H, m), 6.65 (1H, s), 7.30 (2H, s), 7.40 |
| 12-4 | 1H-NMR (CDCl3) δ: 2.52-2.62 (1H, m), 2.87-2.95 (1H, m), 3.61-3.75 (2H, m), 3.88 (3H, s), 4.01 (1H, d), 4.50 (1H, d), 6.39 (1H, d), 7.31 (2H, s), 7.39 (1H, s), 8.06 (1H, dd), 8.84 (1H, d). |
| 12-5 | 1H-NMR (DMSO-d6) δ: 2.61-2.72 (1H, m), 2.90-3.01 (1H, m), 3.57-3.66 (2H, m), 3.96 (1H, d), 4.49 (1H, d), 6.67 (1H, d), 7.65 (2H, s), 7.70 (1H, t), 7.97 (1H, dd), 8.66 (1H, d), 12.46 (1H, br s). |
| 12-10 | 1H-NMR (CDCl3) δ: 2.54-2.59 (1H, m), 2.87-2.95 (1H, m), 3.66-3.68 (2H, m), 3.88-3.97 (4H, m), 4.45-4.48 (1H, m), 6.30 (1H, d), 7.28-7.30 (2H, m), 7.39 (1H, s), 8.05-8.08 (1H, m) |

Biological Test Example 1

Test for Larvae of *Spodoptera litura*

Solvent: 3 parts by weight of dimethylformamide, Emulsifier: 1 part by weight of polyoxyethylene alkyl phenyl ether To prepare a suitable active compound, 1 part by weight of the active compound is mixed with the above amount of the solvent containing the above amount of the emulsifier, and the mixture is diluted with water, to the prescribed concentration.

Leaves of batata are immersed in the sample solution diluted with water to a prescribed concentration and, after the solution depositing on leaves is air-dried, the resultant leaves are put in a laboratory dish of 9 cm in diameter, into which 10 of third stage larvae of *Spodoptera litura* are then released, and the dish is then put in a temperature controlled room at 25° C., followed by addition of leaves of batata to the dish on the second day and fourth day and investigation of the number of dead insects after 7 days to calculate the insecticidal ratio.

The results are the averages of two laboratory dishes per group in this test.

Compounds Nos. 1-3, 1-4, 1-7, 1-8, 1-9, 1-10, 1-11, 1-12, 1-14, 1-15, 1-16, 1-22, 1-23, 1-25, 1-54, 1-55, 1-56, 1-57, 1-63, 1-73, 1-75, 1-81, 1-83, 1-85, 1-86, 1-87, 1-88, 1-90, 1-91, 1-93, 2-8, 2-23, 2-29, 2-40, 2-41, 3-3 and 3-4 showed 100% of death rate at a concentration of 100 ppm of the active compound.

Biological Test Example 2

Test for *Tetranychus urticae* (Spraying Test)

To prepare an appropriate formulation of an active compound, 1 part by weight of the active compound is mixed with the aforementioned amount of the solvent containing the aforementioned amount of the emulsifier, and the mixture is diluted to a prescribed concentration with water.

50 to 100 adult mites of *Tetranychus urticae* are inoculated to leaves of kidney bean at two-leaf stage planted in a pot of 6 cm in diameter. One day after, an ample amount of the diluted aqueous solution of the prescribed concentration of an active compound is sprayed with a spray gun. After the spraying, the pot is kept in a greenhouse for 7 days, and the acaricidal rate is calculated using the following evaluation citeriae:

| Acaricidal rate | |
|---|---|
| 100 | all mites inoculated are dead |
| 98 | 1 to 4 mites survived/propagated |
| 90 | 5 to 20 mites survived/propagated |
| 60 | Many mites survived/propagated, but less than the untreated control, some dead bodies are observed |
| 0 | No difference from the untreated control was observed |

Compounds Nos. 1-3, 1-4, 1-7, 1-8, 1-9, 1-10, 1-12, 1-14, 1-15, 1-16, 1-17, 1-20, 1-22, 1-23, 1-25, 1-54, 1-55, 1-56, 1-57, 1-75, 1-81, 1-84, 1-86, 1-87, 1-90, 2-29, 3-3 and 3-4 showed an acaricidal rate of more than 98% at a concentration of 500 ppm of active compound.

Biological Test Example 3

Test for *Aulacophora femoralis* (Spraying Test)

Solvent: Dimethylformamide 3 parts by weight
Emulsifier: Polyoxyethylene alkyl phenyl ether 1 part by weight To prepare an appropriate formulation of an active compound, 1 part by weight of the active compound is mixed with the aforementioned amount of the solvent containing the aforementioned amount of the emulsifier, and the mixture is diluted to a prescribed concentration with water.

Leaves of cucumbers are soaked in a diluted aqueous solution of the prescribed concentration of an active compound prepared in the same manner as in the aforementioned tests, air-dried, and placed a plastic cup containing sterilized black soil. Into this cup, 5 larvae of *Aulacophora femoralis* at second instar are then released. After 7 days, the number of dead larvae is counted to calculate the death rate.

Compounds Nos. 1-3, 1-4, 1-7, 1-8, 1-9, 1-10, 1-11, 1-12, 1-14, 1-15, 1-16, 1-17, 1-18, 1-20, 1-21, 1-22, 1-23, 1-24, 1-25, 1-54, 1-55, 1-56, 1-57, 1-60, 1-61, 1-80, 1-81, 1-85, 1-87, 1-88, 1-90, 1-91, 2-29, 3-3 and 3-4 showed 100% of death rate at a concentration of 100 ppm of the active compound.

Biological Test Example 4

Test Against Organic Phosphorus Agent- and Carbamate Agent-Resistant *Myzus persicas*

Solvent: Dimethylformamide 3 parts by weight
Emulsifier: Polyoxyethylene alkyl phenyl ether 1 part by weight To prepare an appropriate formulation of an active compound, 1 part by weight of the active compound is mixed with the aforementioned amount of the solvent containing the aforementioned amount of the emulsifier, and the mixture is diluted to a prescribed concentration with water.

About 30 to 50 adults of organic phosphorus agent- and carbamate agent-resistant *Myzus persicae* per seedling are inoculated to leaves of eggplants at two leaf stage cultured in a pot of 6 cm in diameter. One day after the inoculation, an ample amount of the diluted aqueous solution of the prescribed concentration of an active compound prepared in the same manner as in the aforementioned tests is sprayed with a spray gun. After the spraying, the pot is kept in a greenhouse at 28° C. for 7 days, the death rate is calculated. The test is duplicated.

Compounds Nos. 1-7, 1-10, 1-14 and 1-16 showed 98% of death rate at a concentration of 500 ppm of the active compound.

Biological Test Example 5

Test for *Ctenocephalides felis*

Solvent: Dimethylformamide
In order to prepare an appropriate formulation of an active compound, 10 mg of the active compound is dissolved in 0.5 mL of the aforementioned solvent, and the mixture is diluted to a prescribed concentration with blood from domestic animals.

About 10 to 15 adults of *Ctenocephalides felis* were kept in a flea-specific container. Another container containing the blood solution containing the compound prepared as described above is covered with a laboratory film (PARAFILM (Trademark)). The blood containing container is turned upside down and placed on the flea-specific container. This system enables *Ctenocephalides felis* to suck the blood in the container. The blood solution is kept at 37° C. and the flea-specific container is kept at room temperature. After a certain period of time, the death rate of *Ctenocephalides felis* is calculated. For this test, the death rate of 100% means death of all *Ctenocephalides felis*, while the death rate of 0% means that all the fleas survived.

In this biological test, the compound 1-16 showed more than 80% of death rate at a concentration of 100 ppm of the active ingredient.

Biological Test Example 6

Test for *Boophilus microplus*

Solvent: Dimethylformamide
In order to prepare an appropriate formulation of an active compound, 10 mg of the active compound is dissolved in 0.5 mL of the aforementioned solvent, and the mixture is diluted to a prescribed concentration with water.

A solution of a compound formulated as above is injected into 5 fully fed adult female *Boophilus microplus* in their abdomen. These *Boophilus microplus* are transferred to a replica dish and kept in an incubating cabinet for a certain period of time.

After a certain period of time, the death rate of *Boophilus microplus* is calculated. In this test, the death rate of 100% means death of all *Boophilus microplus*, while the death rate of 0% means that all the mites survive.

In the above biological test, the compound 1-16 showed more than 80% of death rate at a dose of 20 µg/animal of the active ingredient.

Biological Test Example 7

Test for *Lucillia cuprina*

Solvent: Dimethylformamide
In order to prepare an appropriate formulation of an active compound, 10 mg of the active compound is dissolved in 0.5 mL of the aforementioned solvent, and the mixture is diluted to a prescribed concentration with water.

About 20 to 30 larvae of *Lucillia cuprina* are placed into a test tube containing 1 cm3 of minced horsemeat and 0.5 mL of an aqueous solution of a compound prepared as above.

After a certain period of time, the death rate of *Lucillia cuprina* is calculated. For this test, the death rate of 100% means death of all *Lucillia cuprina*, while the death rate of 0% means that all the flies survived.

In this biological test, the compound 1-16 showed more than 80% of death rate at a concentration of 100 ppm of the active ingredient.

Formulation Example 1

Granules

To a mixture containing 10 parts of a compound according to the invention, namely compound No. 1-3, 30 parts of bentonite (montmorillonite), 58 parts of talc and 2 parts of ligninsulfonic acid salt is added 25 parts of water, and the mixture is well kneaded and granulated with 10 to 40 meshes by an extruding granulator and dried at 40 to 50° C. to obtain granules.

Formulation Example 2

Granules 95 parts of clay mineral granules having particle diameter distribution within the range of 0.2 to 2 mm, which is put into a rotary mixer, are wetted evenly by spraying of 5 parts of the compound according to the invention, namely compound No. 1-3 together with a liquid diluent under rotating condition and dried at 40 to 50° C. to obtain granules.

Formulation Example 3

Emulsions 30 parts of the compound according to the invention, namely compound No. 1-3, 55 parts of xylene, 8 parts of polyoxyethylene alkylphenyl ether and 7 parts of calcium alkylbenzenesulfonate are mixed together to obtain the emulsion.

Formulation Example 4

Wettable Agent 15 parts of the compound according to the invention, namely compound No. 1-3, 80 parts of a mixture of white carbon (hydrated amorphous silicon oxide fine powder) and powdered clay (1:5), 2 parts of sodium alkylbenzenesulfonate and 3 parts of sodium alkylnaphthalenesulfonate-formalin condensate are mixed together and the mixture is crushed to obtain water dispersible powder.

Formulation Example 5

Wettable Granules 20 parts of the active compound according to the invention, namely compound No. 1-3, 30 parts of sodium ligninsulfonate, 15 parts of bentonite and 35 parts of calcined diatomaceous earth powder are well mixed, and after addition of water, which is then extruded with a screen of 0.3 mm and dried to obtain water-dispersible granules.

INDUSTRIAL AVAILABILITY

Novel aryl pyrrolidines of the invention have an excellent insecticidal action as insecticides as shown in above examples.

The invention claimed is:
1. A method for the preparation of a compound of formula (I)

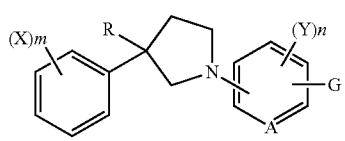

wherein
X which may be same or different, represents halogen, $C_{1-12}$ haloalkyl, nitro, $C_{1-12}$ alkyl, $C_{1-12}$ alkoxy, cyano, $C_{1-12}$ haloalkoxy, $C_{1-12}$ alkylthio, $C_{1-12}$ alkylsulfinyl, $C_{1-12}$ alkylsulfonyl, $C_{1-12}$ haloalkylthio, $C_{1-12}$ haloalkylsulfinyl, $C_{1-12}$ haloalkylsulfonyl, hydroxyl, mercapto, amino, $C_{1-12}$ alkylcarbonylamino, $C_{1-12}$ haloalkylcarbonylamino, benzoylamino, $C_{1-12}$ alkoxy-carbonylamino, $C_{1-12}$ haloalkoxy-carbonylamino, $C_{1-12}$ alkylsulfonylamino or $C_{1-12}$ haloalkylsulfonylamino;
Y which may be same or different, represents halogen, $C_{1-12}$ haloalkyl, nitro, $C_{1-12}$ alkyl, $C_{1-12}$ alkoxy, cyano, $C_{1-12}$ haloalkoxy, $C_{1-12}$ alkylthio, $C_{1-12}$ alkylsulfinyl, $C_{1-12}$ alkylsulfonyl, $C_{1-12}$ haloalkylthio, $C_{1-12}$ haloalkylsulfinyl, $C_{1-12}$ haloalkylsulfonyl, hydroxyl, mercapto, amino, $C_{1-12}$ alkylcarbonylamino, $C_{1-12}$ haloalkylcarbonylamino, benzoylamino, $C_{1-12}$ alkoxy-carbonylamino, $C_{1-12}$ haloalkoxy-carbonylamino, $C_{1-12}$ alkylsulfonylamino or $C_{1-12}$ haloalkylsulfonylamino;
R represents $C_{1-12}$ alkyl or $C_{1-12}$ haloalkyl;
m represents 0, 1, 2, 3, 4 or 5;
n represents 0, 1, 2, or 3;
G is selected from the group consisting of

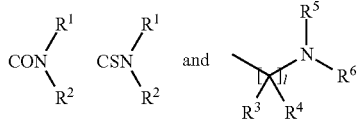

or a group selected from G1 to G9:

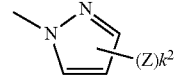

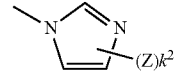

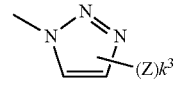

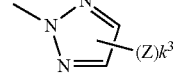

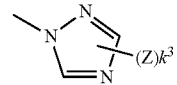

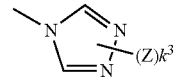

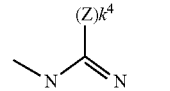

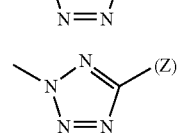

wherein
$R^1$ and $R^2$ each independently represent hydrogen; optionally substituted $C_{1-12}$ alkyl, $C_{2-12}$ alkenyl, $C_{2-12}$ alkynyl, $C_{3-7}$ cycloalkyl; $C_{1-12}$ alkylsulfonyl, $C_{1-12}$ haloalkylsulfonyl or $CH_2$—$R^7$; or when taken together represent $C_{2-6}$ alkylene;
$R^3$ and $R^4$ each independently represent hydrogen, cyano; optionally substituted $C_{1-12}$ alkyl, $C_{2-12}$ alkenyl, $C_{2-12}$ alkynyl, $C_{3-7}$ cycloalkyl; or $C_{1-12}$ alkoxycarbonyl; or when taken together represent $C_{2-6}$ alkylene;
l represents 1 or 2 or 3;
$R^5$ represents hydrogen; $C_{1-12}$ alkyl; optionally substituted $C_{3-7}$ cycloalkyl; $C_{1-6}$ haloalkyl; cyano; $C_{2-12}$ alkenyl; $C_{2-12}$ alkynyl; $C_{1-12}$ alkylcarbonyl; or $CH_2$—$R^7$;
$R^6$ represents formyl, cyano, $C_{1-6}$ alkylcarbonyl, $C_{1-12}$ alkylthiocarbonyl, $C_{1-12}$ haloalkyl-carbonyl, $C_{1-12}$ haloalkylthiocarbonyl, $C_{1-12}$ alkylaminocarbonyl, $C_{1-12}$ alkylaminothio-carbonyl, dialkylamino-carbonyl having from 2 to 8 carbon atoms, dialkylaminothio-carbonyl having from 2 to 8 carbon atoms, $C_{1-12}$ alkoxyaminocarbonyl, $C_{1-12}$ alkoxyaminothiocarbonyl, $C_{1-12}$ alkoxycarbonyl, $C_{1-12}$ alkoxythiocarbonyl, $C_{1-12}$ thioalkoxycarbonyl, $C_{1-12}$ thioalkoxythiocarbonyl, CO—$R^7$, CS—$R^7$, $C_{1-12}$ alkylsulfonyl or $C_{1-12}$ haloalkylsulfonyl; or
$R^5$ and $R^6$ when taken together with the nitrogen to which they are attached to form a 3-6 membered ring which contains at least one N atom and, optionally at least another heteroatom selected from S and O, wherein the ring is optionally substituted with keto or thioketo;
Z which may be same or different, represents halogen, $C_{1-12}$ haloalkyl, nitro, $C_{1-12}$ alkyl, $C_{1-12}$ alkoxy, cyano, $C_{1-12}$ haloalkoxy, $C_{1-12}$ alkylsulfonyl, $C_{1-12}$ haloalkylsulfonyl, hydroxyl or mercapto;

$k^1$ represents 0, 1, 2, 3 or 4;

$k^2$ represents 0, 1, 2 or 3;

$k^3$ represents 0 or 1;

$k^4$ represents 0 or 1;

$R^7$ represents phenyl or a heterocyclic ring, which are optionally substituted with at least one substituent selected from fluorine, chlorine, bromine, iodine and $C_{1-12}$ alkyl; and A represents C or N;

comprising reacting a compound of formula (II)

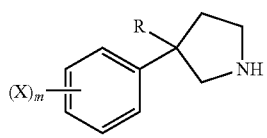
(II)

wherein

X, R and m are as defined above, with a compound of formula (III) or formula (III-a)

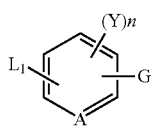
(III)

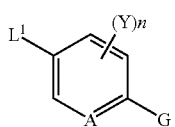
(III-a)

wherein

Y, A, G and n are as defined above, and $L^1$ is halogen or a $C_1$-$C_4$ haloalkylsulfonyloxy group.

2. The method according to claim 1, wherein the compound of formula (II) and the compound of formula (III) or formula (III-a) are reacted in the presence of a base or in the presence of at least one metal catalyst.

3. The method according to claim 2, wherein the metal catalyst is a transition metal catalyst selected from $Pd_2$(dibenzylidene acetone)$_3$, $Pd_2$(dibenzylidene acetone)$_3$CHCl$_3$, Pd(OAc)$_2$, CuI, and Cu$_2$O.

4. The method according to claim 3, wherein the reaction is performed in the presence of a phosphine ligand selected from 2,2'-bis(diphenylphosphino)-1,11'-binaphthaliene (BINAP), 4,5-bis(diphenylphosphino)-9,9-dimethylxanthene (Xantphos), and tributylphosphine, or in the presence of an amine ligand selected from 8-quinolinol, proline, and N,N-dimethylglycine.

5. The method according to claim 4, wherein 1 mole of the compound of formula (II) is reacted with 1 to 3 moles of the compound of formula (III) or formula (III-a) in the presence of 1 to 3 moles of the base and a catalytic amount of $Pd_2$(dibenzylidene acetone)$_3$CHCl$_3$ and Xantphos in toluene.

6. The method according to claim 5, wherein the compound of formula (II) is 3-(3,5-dichlorophenyl)-3-(trifluoromethyl)pyrrolidine and the compound of formula (IIIa) is N-(4-bromo-2-methylbenzyl)acetamide.

7. A method for the preparation of a compound of formula (I)

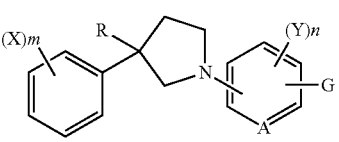
(I)

wherein

X which may be same or different, represents halogen, $C_{1-12}$ haloalkyl, nitro, $C_{1-12}$ alkyl, $C_{1-12}$ alkoxy, cyano, $C_{1-12}$ haloalkoxy, $C_{1-12}$ alkylthio, $C_{1-12}$ alkylsulfinyl, $C_{1-12}$ alkylsulfonyl, $C_{1-12}$ haloalkylthio, $C_{1-12}$ haloalkylsulfinyl, $C_{1-12}$ haloalkylsulfonyl, hydroxyl, mercapto, amino, $C_{1-12}$ alkylcarbonylamino, $C_{1-12}$ haloalkylcarbonylamino, benzoylamino, $C_{1-12}$ alkoxy-carbonylamino, $C_{1-12}$ haloalkoxy-carbonylamino, $C_{1-12}$ alkylsulfonylamino or $C_{1-12}$ haloalkylsulfonylamino;

Y which may be same or different, represents halogen, $C_{1-12}$ haloalkyl, nitro, $C_{1-12}$ alkyl, $C_{1-12}$ alkoxy, cyano, $C_{1-12}$ haloalkoxy, $C_{1-12}$ alkylthio, $C_{1-12}$ alkylsulfinyl, $C_{1-12}$ alkylsulfonyl, $C_{1-12}$ haloalkylthio, $C_{1-12}$ haloalkylsulfinyl, $C_{1-12}$ haloalkylsulfonyl, hydroxyl, mercapto, amino, $C_{1-12}$ alkylcarbonylamino, $C_{1-12}$ haloalkylcarbonylamino, benzoylamino, $C_{1-12}$ alkoxy-carbonylamino, $C_{1-12}$ haloalkoxy-carbonylamino, $C_{1-12}$ alkylsulfonylamino or $C_{1-12}$ haloalkylsulfonylamino;

A represents C or N;

R represents $C_{1-12}$ alkyl or $C_{1-12}$ haloalkyl;

m represents 0, 1, 2, 3, 4 or 5;

n represents 0, 1, 2, or 3;

G represents

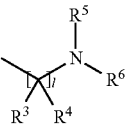

wherein $R^3$ and $R^4$ each independently represent hydrogen, cyano; optionally substituted $C_{1-12}$ alkyl, $C_{2-12}$ alkenyl, $C_{2-12}$ alkynyl, $C_{3-7}$ cycloalkyl; or $C_{1-12}$ alkoxycarbonyl; or when taken together represent $C_{2-6}$ alkylene;

l represents 1 or 2 or 3;

$R^5$ represents hydrogen; $C_{1-12}$ alkyl; optionally substituted $C_{3-7}$ cycloalkyl; $C_{1-6}$ haloalkyl; cyano; $C_{2-12}$ alkenyl; $C_{2-12}$ alkynyl; $C_{1-12}$ alkylcarbonyl; or $CH_2$—$R^7$;

$R^6$ represents formyl, cyano, $C_{1-6}$ alkylcarbonyl, $C_{1-12}$ alkylthiocarbonyl, $C_{1-12}$ haloalkyl-carbonyl, $C_{1-12}$ haloalkylthiocarbonyl, $C_{1-12}$ alkylaminocarbonyl, $C_{1-12}$ alkylaminothio-carbonyl, dialkylamino-carbonyl having from 2 to 8 carbon atoms, dialkylaminothio-carbonyl having from 2 to 8 carbon atoms, $C_{1-12}$ alkoxyaminocarbonyl, $C_{1-12}$ alkoxyaminothiocarbonyl, $C_{1-12}$ alkoxycarbonyl, $C_{1-12}$ alkoxythiocarbonyl, $C_{1-12}$ thioalkoxycarbonyl, $C_{1-12}$ thioalkoxythiocarbonyl, CO—$R^7$, CS—$R^7$, $C_{1-12}$ alkylsulfonyl or $C_{1-12}$ haloalkylsulfonyl; or $R^5$ and $R^6$ when taken together with the nitrogen to which they are attached to form a 3-6 membered ring which contains at least one N atom and, optionally at least another heteroatom selected from S and O, wherein the ring is optionally substituted with keto or thioketo;

$R^7$ represents phenyl or a heterocyclic ring, which are optionally substituted with at least one substituent selected from fluorine, chlorine, bromine, iodine and $C_{1-12}$ alkyl;

comprising reacting a compound of formula (VIII) or formula (VIII-b):

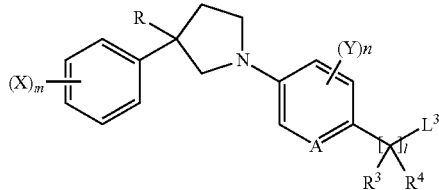
(VIII-b)

wherein
X, Y, R, $R^3$, $R^4$, A, l, m, and n are as defined above, and
$L^3$ represents chlorine, bromine, iodine, $C_{1-4}$ alkylsulfonyloxy, $C_{1-4}$ haloalkylsulfonyloxy, arylsulfonyloxy or azolyl,
with a compound of formula (IX):

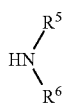
(IX)

wherein
$R^5$ and $R^6$ are as defined above, optionally in the presence of a base.

8. A method for the preparation of a compound of formula (I)

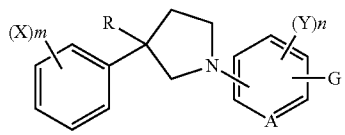
(I)

wherein
X which may be same or different, represents halogen, $C_{1-12}$ haloalkyl, nitro, $C_{1-12}$ alkyl, $C_{1-12}$ alkoxy, cyano, $C_{1-12}$ haloalkoxy, $C_{1-12}$ alkylthio, $C_{1-12}$ alkylsulfinyl, $C_{1-12}$ alkylsulfonyl, $C_{1-12}$ haloalkylthio, $C_{1-12}$ haloalkylsulfinyl, $C_{1-12}$ haloalkylsulfonyl, hydroxyl, mercapto, amino, $C_{1-12}$ alkylcarbonylamino, $C_{1-12}$ haloalkylcarbonylamino, benzoylamino, $C_{1-12}$ alkoxy-carbonylamino, $C_{1-12}$ haloalkoxy-carbonylamino, $C_{1-12}$ alkylsulfonylamino or $C_{1-12}$ haloalkylsulfonylamino;
Y which may be same or different, represents halogen, $C_{1-12}$ haloalkyl, nitro, $C_{1-12}$ alkyl, $C_{1-12}$ alkoxy, cyano, $C_{1-12}$ haloalkoxy, $C_{1-12}$ alkylthio, $C_{1-12}$ alkylsulfinyl, $C_{1-12}$ alkylsulfonyl, $C_{1-12}$ haloalkylthio, $C_{1-12}$ haloalkylsulfinyl, $C_{1-12}$ haloalkylsulfonyl, hydroxyl, mercapto, amino, $C_{1-12}$ alkylcarbonylamino, $C_{1-12}$ haloalkylcarbonylamino, benzoylamino, $C_{1-12}$ alkoxy-carbonyl amino, $C_{1-12}$ haloalkoxy-carbonylamino, $C_{1-12}$ alkylsulfonylamino or $C_{1-12}$ haloalkylsulfonylamino;
A represents C or N;
R represents $C_{1-12}$ alkyl or $C_{1-12}$ haloalkyl;
m represents 0, 1, 2, 3, 4 or 5;
n represents 0, 1, 2, or 3;

G is

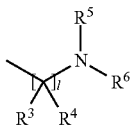

wherein
$R^3$ and $R^4$ each independently represent hydrogen, cyano; optionally substituted $C_{1-12}$ alkyl, $C_{2-12}$ alkenyl, $C_{2-12}$ alkynyl, $C_{3-7}$ cycloalkyl; or $C_{1-12}$ alkoxycarbonyl; or when taken together represent $C_{2-6}$ alkylene;
l represents 1 or 2 or 3;
$R^5$ represents hydrogen; $C_{1-12}$ alkyl; optionally substituted $C_{3-7}$ cycloalkyl; $C_{1-6}$ haloalkyl; cyano; $C_{2-12}$ alkenyl; $C_{2-12}$ alkynyl; $C_{1-12}$ alkylcarbonyl; or $CH_2$—$R^7$;
$R^6$ represents formyl, cyano, $C_{1-6}$ alkylcarbonyl, $C_{1-12}$ alkylthiocarbonyl, $C_{1-12}$ haloalkyl-carbonyl, $C_{1-12}$ haloalkylthiocarbonyl, $C_{1-12}$ alkylaminocarbonyl, $C_{1-12}$ alkylaminothio-carbonyl, dialkylamino-carbonyl having from 2 to 8 carbon atoms, dialkylaminothio-carbonyl having from 2 to 8 carbon atoms, $C_{1-12}$ alkoxyaminocarbonyl, $C_{1-12}$ alkoxyaminothiocarbonyl, $C_{1-12}$ alkoxycarbonyl, $C_{1-12}$ alkoxythiocarbonyl, $C_{1-12}$ thioalkoxycarbonyl, $C_{1-12}$ thioalkox hiocarbonyl, CO—$R^7$, CS—$R^7$, $C_{1-12}$ alkylsulfonyl or $C_{1-12}$ haloalkylsulfonyl; or
$R^5$ and $R^6$ when taken together with the nitrogen to which they are attached to form a 3-6 membered ring which contains at least one N atom and, optionally at least another heteroatom selected from S and O, wherein the ring is optionally substituted with keto or thioketo; and
$R^7$ represents phenyl or a heterocyclic ring, which are optionally substituted with at least one substituent selected from fluorine, chlorine, bromine, iodine and $C_{1-12}$ alkyl;

comprising reacting a compound of formula (X) or formula (X-a):

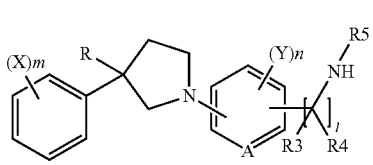
(X)

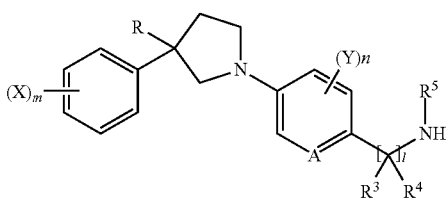
(X-a)

wherein
X, Y, R, $R^3$, $R^4$, $R^5$, A, l, m and n are as defined above, with a compound of formula (XI):

$R^6$-$L^4$ (XI)

wherein
$R^6$ is as defined above, and
$L^4$ represents fluorine, chlorine, bromine, $C_{1-4}$ alkyl-carbonyloxy, $C_{1-4}$ alkoxycarbonyloxy, azolyl, $C_{1-4}$ alkylsulfonyloxy, $C_{1-4}$ haloalkylsulfonyloxy, or arylsulfonyloxy, optionally in the presence of a base.

* * * * *